US009587253B2

(12) United States Patent
Sawai et al.

(10) Patent No.: US 9,587,253 B2
(45) Date of Patent: Mar. 7, 2017

(54) METHOD OF PRODUCING CHEMICAL PRODUCT WITH CONTINUOUS FERMENTATION AND FILTERING

(75) Inventors: Hideki Sawai, Kanagawa (JP); Katsushige Yamada, Kanagawa (JP); Takashi Mimitsuka, Kanagawa (JP); Kenji Sawai, Kanagawa (JP); Tetsu Yonehara, Kanagawa (JP); Yohito Ito, Kanagawa (JP); Masahiro Henmi, Shiga (JP)

(73) Assignee: Toray Industries, Inc. (JP)

( * ) Notice: Subject to any disclaimer, the term of this patent is extended or adjusted under 35 U.S.C. 154(b) by 303 days.

(21) Appl. No.: 12/280,197

(22) PCT Filed: Feb. 16, 2007

(86) PCT No.: PCT/JP2007/052853
§ 371 (c)(1),
(2), (4) Date: Aug. 21, 2008

(87) PCT Pub. No.: WO2007/097260
PCT Pub. Date: Aug. 30, 2007

(65) Prior Publication Data
US 2009/0269812 A1    Oct. 29, 2009

(30) Foreign Application Priority Data

Feb. 24, 2006  (JP) .................................. 2006-048181
Jul. 26, 2006  (JP) .................................. 2006-203072

(51) Int. Cl.
| | | |
|---|---|---|
| C12P 13/04 | (2006.01) | |
| C12P 7/06 | (2006.01) | |
| C12M 1/00 | (2006.01) | |
| C12M 1/34 | (2006.01) | |
| C12P 7/18 | (2006.01) | |
| C12P 7/46 | (2006.01) | |
| C12P 7/50 | (2006.01) | |
| C12P 7/56 | (2006.01) | |
| C12P 13/00 | (2006.01) | |
| C12P 13/08 | (2006.01) | |
| C12P 19/30 | (2006.01) | |

(52) U.S. Cl.
CPC ............... *C12P 7/06* (2013.01); *C12M 29/04* (2013.01); *C12M 29/18* (2013.01); *C12M 41/40* (2013.01); *C12M 47/10* (2013.01); *C12P 7/18* (2013.01); *C12P 7/46* (2013.01); *C12P 7/50* (2013.01); *C12P 7/56* (2013.01); *C12P 13/001* (2013.01); *C12P 13/005* (2013.01); *C12P 13/04* (2013.01); *C12P 13/08* (2013.01); *C12P 19/30* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 5,503,750 A | * | 4/1996 | Russo et al. ................... | 210/641 |
| 2003/0150808 A1 | * | 8/2003 | Morikawa et al. ........... | 210/650 |

FOREIGN PATENT DOCUMENTS

| | | | | |
|---|---|---|---|---|
| JP | 62-138184 | A | 6/1987 | |
| JP | 63-248396 | A | 10/1988 | |
| JP | 01-98473 | A | 4/1989 | |
| JP | 5-95778 | A | 4/1993 | |
| JP | 10-174594 | A * | 6/1998 | ............... C12P 7/42 |
| JP | 10-323543 | A | 12/1998 | |
| JP | 11-113587 | A | 4/1999 | |
| JP | 2003-053164 | A | 2/2003 | |
| JP | 2005-028339 | A | 2/2005 | |
| JP | 2005-111326 | A | 4/2005 | |
| JP | 2005-333886 | A | 12/2005 | |
| JP | 2008-043329 | A | 2/2008 | |
| WO | WO 02/064240 | A1 | 8/2002 | |
| WO | 2005/095578 | | 10/2005 | |

OTHER PUBLICATIONS

Hoek et al, 2003. Effect of membrane surface roughness on colloid-membrane DLVO interactions. Langmuir, vol. 19:4836-4847.*
Hasegawa et al, 1991. Application of ceramic membrane CEFILT®—MF, UF. Key Engineering Materials, vol. 61&62:607-609).*
Toshihiko Hiroo et al., "L-Lysine production in continuous culture of an L-lysine hyperproducing mutant of *Corynebacterium glutamicum*," Applied Microbiology and Biotechnology, 1989, vol. 32, pp. 269-273.
Kanji Matsumoto et al., "Special Feature: Application of Living Organisms Functions and Bioseparation Fermentation of Miso Associated Lactate Using Hollow Fiber Membrane" *Chemical Engineering*, 1991, vol. 36, No. 6, pp. 69-72.
Ohleyer, E. et al., "Continuous Production of Lactic Acid from Glucose and Lactose in a Cell-Recycle Reactor," *Applied Biochemistry and Biotechnology*, 1985, vol. 11, pp. 457-463.
Ishizaki, A. et al., "Cell-Recycled Fermentation of Glutamate Using a Novel Cross-Flow Filtration System with Constant Air Supply," *Journal of Fermentation and Bioengineering*, 1993, vol. 73, No. 4, pp. 316-320.
Seisakusho, I., "Ceramic Sterile Continuous Filtration Device," *Nippon Nogei Kagaku Kaishi, Journal of the Agricultural Chemical*
(Continued)

*Primary Examiner* — Blaine Lankford
(74) *Attorney, Agent, or Firm* — DLA Piper LLP (US)

(57) ABSTRACT

The invention provides a method of producing a chemical product through continuous fermentation which includes filtering a culture of a microorganism or cultured cells with a separation membrane to recover a product from a filtrate and simultaneously retaining a nonfiltered fluid in, or refluxing it to, the culture, and adding fermentation materials to the culture, wherein a porous membrane having an average pore size of 0.01 μm or more to less than 1 μm is used as the separation membrane and the filtration is conducted with a transmembrane pressure difference in the range of 0.1 to 20 kPa. According to this method, the fermentation productivity of the chemical product can be largely elevated at high stability and a low cost.

18 Claims, 3 Drawing Sheets

(56) References Cited

OTHER PUBLICATIONS

Society of Japan, Technical Report, 1986, vol. 60, No. 7, black matter, 3,3 pages in the Japanses language and 2 pages of English translation.
Nakao, S. et al., *New Development of Water Treatment Technology Using Membrane*, CMC Publishing Co. Ltd. (Tokyo), May 2010, pp. 92, 93 and 284 in the Japanese language and 3 pages of English translation.
Patel, P.N. et al., "Cross-Flow Membrane Filtration of Yeast Suspensions," *Journal of Biotechnology*, 1987, No. 5, pp. 1-16.
Camfil Farr, List of Microorganisms, printed from www.camfilfarr.com, pp. 1-3, undated.

\* cited by examiner

//www.w3.org/1999/xhtml">

SEQUENCE LISTING

```
<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcgagatgg caactctaaa ggatca                                         26

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcggccgctt aaaattgcag ctcctttt                                       28

<210> SEQ ID NO 3
<211> LENGTH: 999
<212> TYPE: DNA
<213> ORGANISM: Homo sapiens

<400> SEQUENCE: 3
atggcaactc taaggatca gctgatttat aatcttctaa aggaagaaca gaccccccag     60
aataagatta cagttgttgg ggttggtgct gttggcatgg cctgtgccat cagtatctta   120
```

```
atgaaggact tggcagatga acttgctctt gttgatgtca tcgaagacaa attgaaggga    180
gagatgatgg atctccaaca tggcagcctt ttccttagaa caccaaagat tgtctctggc    240
aaagactata atgtaactgc aaactccaag ctggtcatta tcacggctgg ggcacgtcag    300
caagagggag aaagccgtct taatttggtc cagcgtaacg tgaacatatt taaattcatc    360
attcctaatg ttgtaaaata cagcccgaac tgcaagttgc ttattgtttc aaatccagtg    420
gatatcttga cctacgtggc ttggaagata agtggttttc ccaaaaaccg tgttattgga    480
agtggttgca atctggattc agcccgattc cgttacctga tgggggaaag gctgggagtt    540
cacccattaa gctgtcatgg gtgggtcctt ggggaacatg gagattccag tgtgcctgta    600
tggagtggaa tgaatgttgc tggtgtctct ctgaagactc tgcacccaga tttagggact    660
gataaagata aggaacagtg gaaagaggtt cacaagcagg tggttgagag tgcttatgag    720
gtgatcaaac tcaaaggcta cacatcctgg gctattggac tctctgtagc agatttggca    780
gagagtataa tgaagaatct taggcgggtg cacccagttt ccaccatgat taagggtctt    840
tacggaataa aggatgatgt cttccttagt gttccttgca ttttgggaca gaatggaatc    900
tcagaccttg tgaaggtgac tctgacttct gaggaagagg cccgtttgaa gaagagtgca    960
gatacacttt gggggatcca aaaggagctg caattttaa                           999
```

```
<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctcaattat tattttctac tcataacctc acgcaaaata acacagtcaa atcaatcaaa    60
atggcaactc taaaggatca                                                80

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggcgtatca cgaggccctt                                                20

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattaattc ttgaagacga aagggcctcg tgatacgcct agattgtact gagagtgcac    60

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 7

```
tattttcgt tacataaaaa tgcttataaa actttaacta ataattagag attaaatcgc      60
ctgtgcggta tttcacaccg                                                 80
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
caaatatcgt ttgaatattt ttccg                                           25
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
aatccagatt gcaaccactt                                                 20
```

<210> SEQ ID NO 10
<211> LENGTH: 1011
<212> TYPE: DNA
<213> ORGANISM: Bacillus laevolacticus

<400> SEQUENCE: 10

```
atgaaattct tgatgtatgg agtacaagat catgagagag caacgatcga gaattgggca      60
aatcaacatc aggtggagat cgcaacaacc tcagatttcc tctcagaaga tacagtcgct     120
caatcgaaag gctttgacgg tatctgcatt caacagccga ttgcactcgg aggcccgaat     180
ttatacactc aattaaaaaa caacggtatc aaacagattg ctacacgaac agccggttac     240
gacatgattg atttgaacga agccgagaaa acagtttgt tggtgaccaa tgttccagca      300
tactcccctt acgcagtcgc cgagctcgcg gtcactcagg cgatgcagct cgtccgccat     360
attcctgaat caataaaacg tgttgcaggc aaagattttc gctggtcagg ccttatttcc     420
agagaaatcc gatcattaac ggtcggcata gtcggcaccg ccgcatcgg tgcaacggcc      480 gcacagctct tcaaaggact aggggcaaaa atcattggtt ttgatcaata tcccaacgat     540
cggctaaacg gtatccttga ctatcggcct tcacttgaag acgtgcttaa ggaagctgat     600
atcatttctc ttcacacgcc gcttttgat tcgactcggc acatgatcaa taaaagcaca      660
ttaaaactga tgaaaaatag tgcctatcta atcaatgttg ccagaggcgg cttaattaaa     720
actgaagatc tgattgaagc acttgaaaac ggcgaaattg ccggtgcagc gttagatacc     780
tttgaaaatg aactcatgat taataaagat ctgagtaagc agccgctcaa tgatccgctt     840
ctttcgaaac ttctcgatat ggaacaagtg ctgctcacac cgcatgtcgg cttctttact     900
gagaccgcca ttcaaaacat tgttgaaggt gccttagaca gtgttgtcga ggttttgaag     960
acaggaacaa gcaaaaatct tgttcaagca caaccgctat cggcaaaata a             1011
```

<210> SEQ ID NO 11
<211> LENGTH: 30
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 11
ctcgagatga aattcttgat gtatggagta                                       30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcggccgctt attttgccga tagcggttgt                                       30
```

METHOD OF PRODUCING CHEMICAL PRODUCT WITH CONTINUOUS FERMENTATION AND FILTERING

TECHNICAL FIELD

The present invention relates to a method of producing a chemical product and a continuous fermentation apparatus.

BACKGROUND ART

The fermentation method that is a method of producing a substance, which involves culturing a microorganism or cultured cells, can be roughly classified into (1) a batch fermentation method or a fed-batch fermentation method and (2) a continuous fermentation method.

The batch or fed-batch fermentation method has advantages such as simple facilities and less damage by contaminating bacteria because it is short term cultivation. However, the concentration of a product in a culture is increased with time to reduce productivity and yield due to the influence of osmotic pressure or inhibition by the product. Accordingly, it is difficult to maintain high yield and high productivity stably for a long time.

The continuous fermentation method is characterized in that high yield and high productivity can be maintained for a long time by preventing accumulation of an objective substance at high concentration in a fermenter. Continuous fermentation methods for fermentation of L-glutamic acid and L-lysine have been disclosed (Non-Patent Document 1). In these examples, however, raw materials are continuously fed to a culture while a culture containing microorganisms and cells is withdrawn, so that the microorganisms and cells in the culture are diluted, and therefore the improvement in production efficiency is limited.

In the continuous fermentation method, it has been proposed that microorganisms and cultured cells are filtered with a separation membrane to recover a product from a filtrate, while the filtered microorganisms and cultured cells are retained in, or refluxed to, a culture thereby maintaining a high density of the microorganisms and cultured cells in the culture.

For example, techniques of continuous fermentation in a continuous fermentation apparatus using a ceramics membrane have been disclosed (Patent Documents 1, 2 and 3). However, the disclosed techniques has a problem in the reduction in filtration flow rate and filtration efficiency caused by clogging of the ceramics membrane, and for prevention of this clogging, reverse washing or the like conducted.

A process for producing succinic acid by using a separation membrane has been disclosed (Patent Document 4). In this technique, a high filtration pressure (about 200 kPa) is used in membrane separation. This high filtration pressure not only has disadvantage in costs but also causes physical damage to microorganisms and cells by pressure in filtration treatment and is thus not suitable for continuous fermentation wherein microorganisms and cells are continuously returned to a culture.

Conventional continuous culture is a culture method wherein a fresh medium is fed at a constant rate to a fermenter, and a culture in the same amount as the medium is discharged from the fermenter, thereby keeping the fluid volume in the fermenter always constant. In batch culture, culture is finished when an initial substrate is consumed, whereas in continuous culture, culture can be theoretically continued infinitely. That is, infinite fermentation is theoretically feasible.

In the conventional continuous culture, on the other hand, microorganisms together with a culture are discharged from a fermenter so that the density of microorganisms in the fermenter is hardly kept high. If fermenting microorganisms can be kept at high density in fermentation production, the efficiency of fermentation production per fermentation volume can be improved. For this purpose, microorganisms should be retained in, or refluxed to, a fermenter. The method wherein microorganisms are retained in, or refluxed to, a fermenter includes a method that involves solid-liquid separation of a discharged culture by gravity, for example centrifugation, and returning precipitated microorganisms to a fermenter, and a method that involves filtration to separate microorganisms as solids and discharging a culture supernatant only from a fermenter. However, the method using centrifugation is not practical because of high power cost. The method using filtration requires high pressure for filtration as described above and has been examined mainly at the laboratory level.

As described above, the conventional continuous fermentation methods suffer from various problems and are hardly industrially applicable.

That is, it is still difficult in the continuous fermentation method to achieve high substance productivity by filtering microorganisms and cells with a separation membrane thereby recovering a product from a filtrate and simultaneously refluxing the filtered microorganisms and cells to a culture to improve the density of the microorganisms and cells in the culture and to keep their density high. Hence, there have been demands for innovations in techniques.

Patent Document 1: Japanese Patent Application Laid-open (JP-A) No. 5-95778
Patent Document 2: JP-A No. 62-138184
Patent Document 3: JP-A No. 10-174594
Patent Document 4: JP-A No. 2005-333886
Non-Patent Document 1: Toshihiko Hirao et. al., Appl. Microbiol. Biotechnol., 32, 269-273 (1989)

DISCLOSURE OF THE INVENTION

The present invention relates to a method of producing a chemical product through continuous-fermentation which includes filtering a culture of a microorganism or cultured cells with a separation membrane to recover a product from a filtrate and simultaneously retaining a nonfiltered fluid in, or refluxing it to, the culture, and adding fermentation materials to the culture, wherein a porous membrane having an average pore size of 0.01 μm or more to less than 1 μm is used as the separation membrane and the filtration is conducted with a transmembrane pressure difference in the range of 0.1 to 20 kPa.

The present invention relates to the method of producing a chemical product, wherein the purified-water permeability coefficient of the porous membrane is preferably $2 \times 10^{-9}$ m$^3$/m$^2$/s/pa or more to $6 \times 10^{-7}$ m$^3$/m$^2$/s/pa or less.

The present invention relates to the method of producing a chemical product, wherein the average pore size of the porous membrane is preferably 0.01 μm or more to less than 0.2 μm, and the standard deviation of the pore size of the porous membrane is preferably 0.1 μm or less.

The present invention relates to the method of producing a chemical product, wherein the porous membrane is preferably a porous membrane having a surface roughness of 0.1 μm or less.

The present invention relates to the method of producing a chemical product, wherein the porous membrane is preferably a porous membrane containing a porous resin layer.

One continuous fermentation apparatus of the present invention is an apparatus for producing a chemical product through continuous fermentation which includes filtering a fermentation culture of a microorganism or cultured cells with a separation membrane to recover a product from a filtrate and simultaneously retaining a nonfiltered fluid in, or refluxing it to, the fermentation culture, and adding fermentation materials to the fermentation culture, including a fermentation reaction tank for fermentation culture of a microorganism or cultured cells; a membrane separation tank for filtration of the fermentation culture, which is connected via fermentation culture circulating means to the fermentation reaction tank and provided therein with a separation membrane; and means for regulating the transmembrane pressure difference of the separation membrane in the range of 0.1 to 20 kPa, wherein the separation membrane is a porous membrane having an average pore size of 0.01 μm or more to less than 1 μm.

Another continuous fermentation apparatus of the present invention is an apparatus for producing a chemical product through continuous fermentation which includes filtering a fermentation culture of a microorganism or cultured cells with a separation membrane to recover a product from a filtrate and simultaneously retaining a nonfiltered fluid in, or refluxing it to, the fermentation culture, and adding fermentation materials to the fermentation culture, including a fermentation reaction tank for fermentation culture of a microorganism or cultured cells; a separation membrane element for filtration of the fermentation culture, which is arranged in the inside of the fermentation reaction tank and provided therein with a separation membrane; means for discharging a filtered fermentation product, which is connected to the separation membrane element; and means for regulating the transmembrane pressure difference of the separation membrane in the range of 0.1 to 20 kPa, wherein the separation membrane is a porous membrane having an average pore size of 0.01 μm or more to less than 1 μm.

DESCRIPTION OF THE REFERENCE NUMERALS

Figure 1:
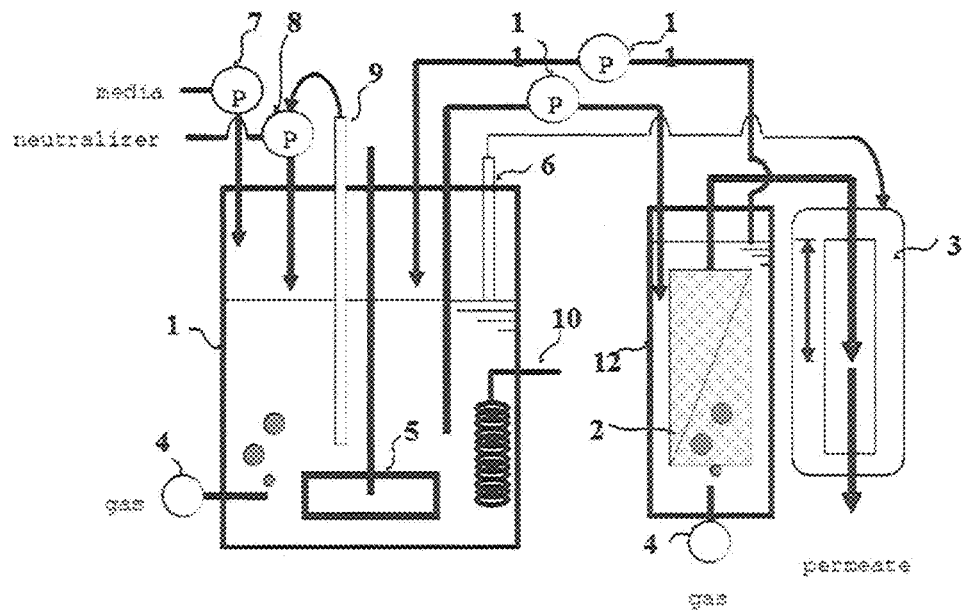
FIG. 1 is a schematic side view for showing one example of the membrane separation-type continuous fermentation apparatus used in the present invention.

1 Fermentation reaction tank
2 Separation membrane element
3 Water head difference regulating apparatus
4 Gas feeding apparatus
5 Agitator
6 Level sensor
7 Medium feeding pump
8 pH regulating solution feeding pump
9 pH sensor/regulator
10 Temperature regulator
11 Fermentation liquor circulating pump
12 Membrane separation tank
13 Support plate
14 Passage material
15 Separation membrane
16 Concave part
17 Water collecting pipe
18 Separation membrane bundle
19 Upper resin sealing layer
20 Lower resin sealing layer
21 Support frame
22 Water collecting pipe.

BEST MODE FOR CARRYING OUT THE INVENTION

The present invention relates to a method of producing a chemical product through continuous fermentation which includes filtering a culture of a microorganism or cultured cells with a separation membrane to recover a product from a filtrate and simultaneously retaining a nonfiltered fluid in, or refluxing it to, the culture, and adding fermentation materials to the culture, wherein a porous membrane having an average pore size of 0.01 μm or more to less than 1 μm is used as the separation membrane and the filtration is conducted with a transmembrane pressure difference in the range of 0.1 to 20 kPa.

The porous membrane used as a separation membrane in the present invention is described.

The constitution of the porous membrane used as a separation membrane in the present invention is described. The porous membrane in the present invention preferably has separation performance and water permeation performance depending on the intended use and the water quality of water to be treated.

The porous membrane is preferably a porous membrane containing a porous resin layer from the viewpoint of prevention performance, water permeation performance and separation performance, for example contamination resistance.

Preferably, the porous membrane containing a porous resin layer has a porous resin layer playing a role in a separation functional layer on the surface of a porous base material. The porous base material supports the porous resin layer to give strength to the separation membrane.

The porous membrane used in the present invention has a porous resin layer preferably on the surface of a porous base material, the porous resin layer may or may not penetrate into the porous base material, depending on use.

The average thickness of the porous base material is preferably 50 or more to 3000 μm or less.

The material of the porous base material is made of an organic material and/or an inorganic material, and organic fibers are desirably used. The porous base material is preferably a woven or nonwoven fabric prepared from organic fibers such as cellulose fibers, cellulose triacetate fibers, polyester fibers, polypropylene fibers and polyethylene fibers. More preferably, an easily manufactured and inexpensive nonwoven fabric of relatively easily regulated density is used.

As the porous resin layer, an organic polymer membrane can be preferably used. The material of the organic polymer membrane includes, for example, a polyethylene resin, polypropylene resin, polyvinyl chloride resin, polyvinylidene fluoride resin, polysulfone resin, polyether sulfone resin, polyacrylonitrile resin, cellulose resin and cellulose triacetate resin. The organic polymer membrane may be a resin mixture containing these resins as the major component. The major component used herein refers to a component that is contained in an amount of 50% by weight or more, preferably 60% by weight or more. The material of the organic polymer membrane is preferably a resin which is excellent in physical durability and chemical resistance and whose solution can be easily formed into a membrane, such as a polyvinyl chloride resin, polyvinylidene fluoride resin, polysulfone resin, poly-ether sulfone resin or polyacrylonitrile resin, and a polyvinylidene resin or a resin containing the same as the major component is most preferably used.

As the polyvinylidene fluoride resin, a homopolymer of vinylidene fluoride is preferably used. As the polyvinylidene fluoride resin, a copolymer of vinylidene flucride and a vinyl monomer copolymerizable therewith can also be preferably used. The vinyl monomer copolymerizable with vinylidene fluoride can be exemplified by tetrafluoroethylene, hexafluoropropylene and ethylene chloride trichloride.

It is important that the porous membrane used in the present invention is 0.01 μm or more to less than 1 μm in average pore size. When the average pore size of the porous membrane is 0.01 μm or more to less than 1 μm, the porous membrane hardly undergoes clogging with microorganisms used in fermentation and has filtration performance lasting stably for a long time. Further when the average pore size of the porous membrane is 0.01 μm or more to less than 1 μm, a high exclusion rate at microorganisms or cultured cells are prevented from being leaked, and high water permeability, can be simultaneously satisfied, and thus water permeability can be maintained for a long time with high accuracy and reproducibility.

The average pore size of the porous membrane is less than 1 μm, because when the pore size is near to the size of a microorganism or cultured cell, the pore may be directly clogged with the microorganism or cultured cell. The average pore size of the porous membrane is preferably not too large as compared with the size of a microorganism or cultured cell, to prevent leakage of the microorganism or cultured cell, that is, to prevent a disadvantage of reduction in exclusion rate. When the microorganism or cultured cell is a bacterium having a small cell, the average pore size is preferably 0.4 μm or less, particularly less than 0.2 μm for more preferable operation.

A microorganism or cultured cells may produce substances other than an objective chemical product, for example easily aggregated substances such as proteins and polysaccharides, and a part of the microorganisms or cultured cells in a culture may perish to form disrupted cells. For preventing clogging of the porous membrane with such substances, the average pore size is preferably 0.1 μm or less.

Generally, the average pore size of the porous membrane is preferably 0.4 μm or less, more preferably less than 0.2 μm, or 0.1 μg/m or less.

When the average pore size is too small, the water permeation performance of the porous membrane may be reduced, thus making efficient operation infeasible even if the membrane is not soiled. Therefore, the average pore size of the porous membrane in the present invention is 0.01 μm or more, more preferably 0.02 μm or more, even more preferably 0.04 μm or more.

The average pore size can be determined by measuring the diameters of all pores observable in an area of 9.2 μm×10.4 μm under observation with a scanning electron microscope at a magnification of ×10,000 and then averaging the measured diameters. Alternatively, the average pore size can be determined by taking a picture of the surface of the membrane with a scanning electronmicroscope at a magnification of ×10,000, then selecting 10 or more (preferably 20 or more) pores at random, measuring the diameters of the selected pores, and number-averaging the measured diameters. When the pore is not circular, the average pore size can be determined by a method of determining a circle having area equivalent to that of the pore with an image processor or the like, and assuming that the diameter of the equivalent circle is the diameter of the pore, the average pore size is determined.

The standard derivation a of the average pore size of the porous membrane used in the present invention is preferably 0.1 μm or less. The standard deviation of the average pore size is desirably lower. The standard deviation a of the average pore size can be calculated using the following equation (1):

[Equation 1]

$$\sigma = \sqrt{\frac{\sum_{k=1}^{N} (X_k - X(ave))^2}{N}} \qquad (1)$$

wherein N is the number of pores observable in the above-mentioned area of 9.2 μm×10.4 μm, Xk is the diameter of each of measured pores, and X (ave) is the average pore size.

For the porous membrane used in the present invention, its permeability to a culture is one important performance. As an indicator of the permeability of the porous membrane, the purified-water permeability coefficient of the porous membrane before use can be used. In the present invention, the purified-water permeability coefficient of the porous membrane, as calculated by measuring, at 1 m water head pressure, the amount of penetrated water at 25° C. previously purified with a reverse osmosis membrane, is preferably not less than $2\times10^{-9}$ $m^3/m^2/s/Pa$. When the purified-water permeability coefficient is in the range of $2\times10^{-9}$ $m^3/m^2/s/Pa$ or more to $6\times10^{-7}$ $m^3/m^2/s/Pa$ or less, a practically sufficient amount of penetrated water can be attained.

In the porous membrane used in the present invention, the surface roughness is the average height in a direction perpendicular to the surface. The surface roughness of the membrane is one of factors by which microorganisms or cultured cells adhering to the surface of the separation membrane are made easily removable by a membrane surface washing effect resulting from a liquid flow under stirring or with a circulating pump. The surface roughness of the porous membrane is preferably 0.1 μm or less. When the surface roughness is 0.1 μm or less, microorganisms or cultured cells adhering to the membrane are easily removable.

It was found that a porous membrane having a surface roughness of 0.1 μm or less, an average pore size of 0.01 μm or more to less than 1 μm, and a purified-water permeability coefficient of not less than $2\times10^{-9}$ $m^3/m^2/s/Pa$ can be more preferably used to carry out the operation more easily without requiring excessive power necessary for washing the surface of the membrane. When the surface roughness of the porous membrane is 0.1 μm or less, the shear strength generated on the surface of the membrane upon filtration of microorganisms or cultured cells can be reduced, and thus the microorganisms can be prevented from being broken, and the porous membrane can also be prevented from being clogged, thereby more easily enabling stable filtration for a long time. The surface roughness of the porous membrane is preferably 0.1 μm or less so that the membrane enables continuous fermentation with a lower transmembrane pressure difference, and even upon clogging, is excellent in recovery by washing as compared with the case of operation with a high transmembrane pressure difference. Because stable continuous fermentation is made feasible by preventing clogging, the surface roughness of the porous membrane is preferably lower.

The surface roughness of the membrane was measured with the following atomic force microscope (AFM) under the following conditions:
Unit: Atomic force microscope (Nanoscope IIIa manufactured by Digital Instruments)
Conditions
Probe: SiN cantilever (manufactured by Digital Instruments)
  Scanning mode: contact mode (measurement in air)
  Underwater tapping mode (measurement in water)
Scanning range: 10 μm, 25 μm on a side (measurement in air)
  5 μm, 10 μm on a side (measurement in air)
Scanning resolution: 512×512
Preparation of a sample: A membrane sample was dipped in ethanol at ordinary temperatures for 15 minutes, then dipped in RO water for 24 hours, washed and air-dried before measurement.

From the height in the direction of the Z-axis at each point, the surface roughness drough of the membrane was calculated with the atomic force microscope (AFM) using the following equation (2):

[Equation 2]

$$d_{rough} = \sum_{n=1}^{N} \frac{|Z_n - \bar{Z}|}{N} \qquad (2)$$

$d_{rough}$: Average surface roughness
$Z_n$: Height in the Z-axis
$\bar{Z}$: Average height in scanning range The porous membrane used in the present invention is preferably a flat sheet membrane. When the porous membrane is a flat sheet membrane, the average thickness thereof is selected depending on the intended use. When the porous membrane is a flat sheet membrane, the average thickness thereof is preferably 20 or more to 5000 μm or less, more preferably 50 or more to 2000 μm or less.

The porous membrane used in the present invention is preferably a hollow fiber membrane. When the porous membrane is a hollow fiber membrane, the inner diameter of the hollow fiber is preferably 200 to 5000 μm, and the thickness of the membrane is preferably 20 to 2000 μm. A fabric or textile made of cylindrical organic or inorganic fibers may be contained in the inside of the hollow fiber.

A method of forming the porous membrane used in the present invention is described by reference to an outline of the method.

Now, the method of forming a flat sheet membrane of the porous membrane is briefly described.

A coating of a stock solution containing a resin and solvent is formed on the surface of a porous base material, and simultaneously the porous base material is impregnated with the stock solution. Thereafter, only the surface, at the side of the coating, of the porous base material is contacted with a coagulation bath containing a non-solvent thereby coagulating the resin and simultaneously forming a porous resin layer on the surface of the porous base material.

The stock solution is prepared as dissolving a resin in a solvent. From the viewpoint of membrane-making property, it is usually preferable that the temperature of the stock solution is selected in the range of 5 to 120° C. The solvent dissolves a resin and acts on the resin to promote formation of a porous resin layer of the resin. The solvent that can be used herein includes N-methylpyrrolidinone (NMP), N,N-dimethylacetamide (DMAc), N,N-dimethylformamide (DMF), dimethylsulfoxide (DMSO), N-methyl-2-pyrrolidone, methyl ethyl ketone, tetrahydrofuran, tetramethyl urea, trimethyl phosphate, cyclohexanone, isophorone, γ-butyrolactone, methyl isoamyl ketone, dimethyl phthalate, propylene glycol methyl ether, propylene carbonate, diacetone alcohol, glycerol triacetate, acetone, and methyl ethyl ketone. Among these solvents, N-methylpyrrolidinone (NMP), N,N-dimethylacetamide (DMAc), N,N-dimethylformamide (DMF) and dimethylsulfoxide (DMSO), which can highly dissolve the resin, can be preferably used. These solvents may be used alone or as a mixture of two or more thereof.

For example, components other than the solvent, for example polyethylene glycol, polyvinyl alcohol, polyvinyl pyrrolidone, and glycerin may be added to the solvent. A non-solvent may also be added to the solvent. The non-solvent is a liquid that does not dissolve the resin. The non-solvent acts as a regulator of pore size by regulating the rate of coagulation of the resin. As the non-solvent, water and alcohols such as methanol and ethanol can be used. Particularly, the non-solvent is preferably water or methanol from the viewpoint of price. The component other than the solvent, and the non-solvent, may also be a mixture.

A pore-forming agent may also be added to the stock solution. The pore-forming agent has such role that upon immersion in a coagulation bath, it is extracted from a resin layer to make the resin layer porous. By adding the pore-forming agent, the average pore size of the porous membrane can be regulated. Preferably, the pore-forming agent is highly soluble in the coagulation bath. Examples of the usable pore-forming agents include inorganic salts such as calcium chloride and calcium carbonate. Alternatively, as the pore-forming agents, polyoxyalkylenes, e.g., polyethylene glycol and polypropylene glycol; water-soluble polymers, e.g., polyvinyl alcohol, polyvinyl butyral, and polyacrylic acids; and glycerin may be used.

Then, the method of forming a hollow fiber membrane as the porous membrane is briefly described.

The hollow fiber membrane can be prepared by discharging a stock solution made of a resin and solvent through an outer pipe of a double-pipe base and simultaneously discharging a hollow-forming fluid through an inner pipe of the double-pipe base and solidifying them by cooling in a cooling bath.

The stock solution can be prepared by dissolving the resin described above in the method of preparing a flat sheet membrane, at a concentration of 20% or more to 60% or less by weight, in the solvent described above in the method of preparing a flat sheet membrane. The hollow-forming fluid may be usually a gas or liquid. The outer surface of the resulting hollow fiber membrane can also be coated (laminated) with a new porous resin layer. Lamination can be conducted to change the properties (for example, hydrophilicity/hydrophobicity, pore size, etc.) of the hollow fiber membrane into desired properties. The new porous resin layer to be laminated thereon can be prepared by bringing the stock solution having a resin dissolved in a solvent into contact with a non-solvent-containing coagulation bath to coagulate the resin. As a material of the resin, the same material as in the organic polymer membrane for example can be preferably used. The lamination method is not particularly limited, and the hollow fiber membrane may be immersed in the stock solution or may be coated thereon with the stock solution, and after lamination, a part of the adhering stock solution can be scraped off or blown off with an air knife to regulate the amount of the laminate.

The porous membrane used in the present invention can be formed into a separation membrane element by bonding/sealing of a hollow of the hollow fiber membrane with a member such as a resin and then disposing the membrane on a support.

The porous membrane used in the present invention can be combined with a support to form a separation membrane element. The separation membrane element having a support plate as a support in which the porous membrane used in the present invention is disposed on at least one side of the support plate, is one preferable mode of the separation membrane element having the porous membrane used in the present invention. A separation membrane element having the porous membrane on both sides of a support plate to increase the amount of penetrating water is also a preferable mode of the separation membrane element.

The method of producing a chemical product according to the present invention includes filtration with a transmembrane pressure difference in the range of 0.1 to 20 kPa. When a fermentation culture is filtered with a transmembrane pressure difference of higher than 26 kPa, electric power is necessary for applying pressure, thus reducing economic effectiveness in producing a chemical product. Given a transmembrane pressure difference of higher than 20 kPa, a microorganism or cultured cells may be disrupted to reduce the ability to produce a chemical product. In the method of producing a chemical product according to the present invention, the transmembrane pressure difference, that is, filtration pressure is in the range of 0.1 to 20 kPa that can be attained by a water head difference, and thus it is not necessary that the inside of the fermenter be particularly kept under pressure, so that the ability to produce a chemical product is not reduced. Because it is not necessary that the inside of the fermenter be particularly kept under pressure, the porous membrane can be arranged inside of the fermenter, which can result in another advantage to downsizing of the fermentation apparatus. The method of producing a chemical product according to the present invention includes filtration with a transmembrane pressure difference preferably in the range of 0.1 to 2 kPa.

In the method of procuring a chemical product according to the present invention, fermentation materials are used. The fermentation materials used in the present invention may be any materials which promote growth of a culturing microorganism to allow the microorganism to satisfactorily produce an objective fermentation product as the chemical product.

The fermentation materials used in the present invention are preferably in the form of an ordinary liquid medium containing a carbon source, a nitrogen source and inorganic salts and appropriately containing organic micronutrients such as amino acids and vitamins as necessary. The carbon source that can be used herein include sugars such as glucose, sucrose, fructose, galactose and lactose, starch sugars containing these sugars, sweet potato molasses, sugar beet molasses, and high-test molasses, organic acids such as acetic acid, alcohols such as ethanol, and glycerin. The nitrogen source that can be used herein include ammonia gas, ammonia water, ammonium salts, urea, nitrates, and other secondarily used organic nitrogen sources, for example oil cakes, soybean hydrolysates, casein digest, other amino acids, vitamins, corn steep liquor, yeasts or yeast extract, meat extract, peptides such as peptone, and various fermentation microorganisms and their hydrolysates. The inorganic salts that can be appropriately added include phosphates, magnesium salts, calcium salts, iron salts and manganese salts.

When the microorganisms used in the present invention require a specific nutrient for their growth, the nutrient is added as a preparation or as a natural product containing the same. An antifoaming agent is used if necessary. The culture in the present invention refers to a liquid obtained as a result of growth of a microorganism or cultured cells with the fermentation materials. The composition of fermentation materials to be added may be appropriately changed from the composition of the fermentation materials used at the start of culturing.

In the present invention, the concentration of sugars in the culture is kept preferably at 5 g/l or less. The reason that the concentration of sugars in the culture is kept preferably at 5 g/l or less is that the outflow of sugars upon withdrawal of the culture can be minimized at that concentration.

The microorganism is cultured usually at pH 4 to 8 at a temperature in the range of 20 to 40° C. The pH of the culture is adjusted to a predetermined value usually in the range of pH 4 to 8 with an inorganic or organic acid, an alkaline substance, urea, calcium carbonate, ammonia gas, or the like. When it is necessary to increase the supply rate of oxygen, it is possible to employ means for adding oxygen to air to maintain an oxygen concentration not lower than 21% or means for pressurizing the culture or increasing the stirring rate, or enhancing aeration.

In the method of producing a chemical product according to the present invention, batch culture or fed-batch culture may be conducted at an initial stage of culture to increase the density of microorganisms, followed by continuous culture (withdrawal). In the method of producing a chemical product according to the present invention, the density of microorganisms may be increased followed by seeding a high density of microorganisms, thereby initiating culture and simultaneously carrying out continuous culture. In the method of producing a chemical product according to the present invention, supply of the starting culture and withdrawal of the culture may be initiated at a suitable stage. The time of initiating supply of the starting culture and the time of initiating withdrawal of the culture may not always be the same. Supply of the starting culture and withdrawal of the culture may be conducted continuously or intermittently.

Nutrients necessary for growth of the microorganism may be added to the starting culture so that the microorganism grows continuously. For attaining efficient productivity, the density of microorganisms or cultured cells in the culture is preferably kept high in a range that the environment of the culture is not made unsuitable for growth of the microorganisms or cultured cells to cause a high death rate. By way of example, the microorganisms or cultured cells in the culture kept at a density of not lower than 5 g/L in dry weight thereby has made possible excellent production efficiency.

In the method of producing a chemical product according to the present invention, the microorganisms or cultured cells can be withdrawn as necessary from the fermenter. Because the separation membrane is easily clogged for example when the density of the microorganisms or cultured cells in the fermenter becomes too high, such clogging can be prevented by withdrawal. The performance of production of a chemical product may vary depending on the density of the microorganisms or cultured cells in the fermenter, and the productive performance can be maintained by withdrawing the microorganisms or cultured cells with the productive performance as an indicator.

In the method of producing a chemical product according to the present invention, the number of fermenters is not limited as long as the operation of continuous culture during which fresh microorganisms capable of fermentation production are grown is carried out by a continuous culture method wherein the microorganisms are grown and simultaneously a product is formed. In the method of producing a chemical product according to the present invention, it is preferable for control of culture that the operation of continuous culture is usually carried out in a single fermenter. However, a plurality of fermenters may be used for reasons such as a small capacity of the fermenter. In this case, a plurality of fermenters can be connected in parallel, or in series, in continuous fermentation to achieve high productivity of the fermentation product.

Now, the microorganisms or cultured cells that can be used in the method of producing a chemical product according to the present invention are described. The microorganisms or cultured cells that can be used in the method of producing a chemical product according to the present invention are not limited. The microorganisms or cultured cells used in the present invention include, for example, yeasts such as baker's yeast (*Saccharomyces cerevisiae*) used frequently in fermentation industry, bacteria such as *Escherichia coli* or *coryneform* bacteria, filamentous bacteria, mycobacteria, animal cells and insect cells. The microorganisms or cells used may be those isolated from the natural environment or may be those having properties modified partially by mutation or genetic recombination.

The chemical product produced by the method of producing a chemical product according to the present invention is not limited as long as it is a substance produced in a culture by the microorganisms or cells described above. The chemical product produced by the method of producing a chemical product according to the present invention includes substances such as alcohols, organic acids, amino acids and nucleic acid that are produced in large amounts in fermentation industry. Examples of such chemical products include alcohols such as ethanol, 1,3-propanediol, 1,4-butanediol and glycerol, organic acids such as acetic acid, lactic acid, pyruvic acid, succinic acid, malic acid, itaconic acid and citric acid, nucleic acids, for example nucleosides such as inosine and guanosine and nucleotides such as inosinic acid and guanylic acid, and diamine compounds such as cadaverine. The present invention can also be applied to production of substances such as enzymes, antibiotics, and recombinant proteins.

Now, the microorganisms or cultured cells that can be used in the method of producing a chemical product according to the present invention are described by reference to specific chemical products.

In the method of producing a chemical product according to the present invention, the microorganisms or cultured cells that can be used in production of L-lactic acid are not particularly limited as long as they are microorganisms capable of producing L-lactic acid. In the method of producing a chemical product according to the present invention, the microorganisms or cultured cells that can be used in production of L-lactic acid are preferably lactic acid bacteria. The lactic acid bacteria as used herein can be defined as prokaryotic microorganisms producing 50% or more lactic acid as yield to sugar (consumed glucose). Preferable examples of lactic acid bacteria include lactic acid bacteria belonging to the genus *Lactobacillus*, genus *Pediococcus*, genus *Tetragenococcus*, genus *Carnobacterium*, genus *Vagococcus*, genus *Leuconostoc*, genus *Oenococcus*, genus *Atopobium*, genus *Streptococcus*, genus *Enterococcus*, genus *Lactococcus*, and genus *Bacillus*. Among them, lactic acid bacteria having a high yield of lactic acid to sugar can be selected and used preferably in production of lactic acid. In the method of producing a chemical product according to the present invention, lactic acid bacteria having a high yield of lactic acid, particularly L-lactic acid, to sugar can be selected and used preferably in production of lactic acid. L-lactic acid is one kind of optical isomers of lactic acid and can be clearly distinguished from its enantiomer D-lactic acid. Examples of lactic acid bacteria having a high yield of L-lactic acid to sugar include *Lactobacillus yamanashiensis, Lactobacillus animalis, Lactobacillus agilis, Lactobacillus aviaries, Lactobacillus casei, Lactobacillus delbruekii, Lactobacillus paracasei, Lactobacillus rhamnosus, Lactobacillus ruminis, Lactobacillus salivarius, Lactobacillus sharpeae, Pediococcus dextrinicus*, and *Lactococcus lactis*, and these can be selected to produce L-lactic acid.

When L-lactic acid is produced by the method of producing a chemical product according to the present invention, the microorganisms or cultured cells that were artificially endowed with, or allowed to enhance, the ability to produce lactic acid can be used. For example, the microorganisms or cultured cells into which an L-lactate dehydrogenase gene (hereinafter referred to sometimes as L-LDH) was introduced to confer or enhance the ability to produce L-lactic acid can be used. The method of conferring or enhancing the ability to produce L-lactic acid may also be a chemical mutagenesis method known in the art. The microorganism is preferably a recombinant microorganism whose ability to produce L-lactic acid was enhanced by integration of L-LDH. When L-lactic acid is produced by the method of producing a chemical product according to the present invention, a host of the recombinant microorganism is preferably *Escherichia coli* or a lactic acid bacterium that is a prokaryotic cell or yeast that is an eukaryotic cell, particularly preferably a yeast. The yeast is preferably a yeast belonging to the genus *Saccharomyces*, more preferably *Saccharomyces cerevisiae*.

The L-LDH used in the present invention is not limited as long as it encodes a protein having an activity of converting reduced nicotinamide adenine dinucleotide (NADH) and pyruvic acid into oxidized nicotinamide adenine dinucleotide (NAD$^+$) and L-lactic acid. For example, L-LDH derived from lactic acid bacteria having a high yield of L-lactic acid to sugar can be used. Preferably mammal-derived L-LDH can be used. Particularly *Homo sapiens*- or frog-derived L-LDH can be used. The frog-derived L-LDH that can be used in the invention is particularly preferably L-LDH derived from a frog belonging to *Pipidae*, more preferably L-LDH derived from *Xenopus laevis* that is a frog belonging to *Pipidae*.

The human or frog-derived L-LDH used in the present invention includes mutant-type genes resulting from genetic polymorphism, mutagenesis or the like. Genetic polymorphism refers to a partial change in a nucleotide sequence of a gene by spontaneous mutation on the gene. Mutagenesis refers to artificial introduction of a mutation into a gene. Mutagenesis can be achieved for example by a method of using a kit for site-directed mutagenesis (Mutan-K manufactured by Takara Bio) or a method of using a kit for random mutagenesis (BD Diversify PCR Random Mutagenesis manufactured by CLONTECH). The human- or frog-derived L-LDH used in the present invention may have a deletion or insertion in a part of the nucleotide sequence thereof as long as it encodes a protein having an activity of converting NADH and pyruvic acid into $NAD^+$ and L-lactic acid.

When L-lactic acid is produced by the method of producing a chemical product according to the present invention, the separation and purification of L-lactic acid contained in the produced filtered/separated fermentation liquor can be conducted by a combination of conventionally known methods such as concentration, distillation and crystallization. Examples thereof include a method that involves lowering the pH of the filtered/separated fermentation liquor to 1 or less and then extracting L-lactic acid with diethyl ether, ethyl acetate or the like, a method that involves adsorbing the fermentation liquor onto anion-exchange resin, washing the resin, and eluting L-lactic acid, a method that involves reacting L-lactic acid in the fermentation liquor with an alcohol in the presence of an acid catalyst to convert it into the corresponding ester followed by distillation thereof, and a method that involves crystallizing L-lactic acid as a calcium salt or a lithium salt. Preferably, a concentrated L-lactic acid solution obtained by evaporating water from the filtered/separated fermentation liquor can be subjected to distillation. In distillation, the original solution to be distilled is subjected to distillation preferably while water is fed to it such that the water concentration of the solution is kept constant. An aqueous solution of L-lactic acid obtained by distillation can be concentrated by evaporating water therefrom under heating to give an object concentration of purified L-lactic acid. When an aqueous solution of L-lactic acid containing low-boiling-point components such as ethanol and acetic acid is obtained as a distillate, the low-boiling-point components are preferably removed in a step of concentrating L-lactic acid. After the distillation operation, the distillate can also be purified with an ion-exchange resin or activated charcoal, by chromatographic separation or the like as necessary to remove impurities, to give L-lactic acid of higher purity.

When D-lactic acid is produced by the method of producing a chemical product according to the present invention, the microorganisms or cultured cells that can be used in production of D-lactic acid are not limited as long as they can produce D-lactic acid. The microorganisms or cultured cells that can be used in production of D-lactic acid include, for example, microorganisms belonging to the wild-type strain of the genera *Lactobacillus, Bacillus* and *Pediococcus* having an ability to synthesize D-lactic acid.

When D-lactic acid is produced by the method of producing a chemical product according to the present invention, the microorganisms or cultured cells used are preferably those in which the enzyme activity of D-lactate dehydrogenase (hereinafter referred to sometimes as D-LDH) of the wild-type strain has been enhanced. The method of enhancing the enzyme activity may also be a chemical mutagenesis method known in the art. More preferably, the microorganism is a recombinant microorganism in which the enzyme activity of D-lactate dehydrogenase has been enhanced by integration of a gene encoding D-lactate dehydrogenase. When D-lactic acid is produced by the method of producing a chemical product according to the present invention, a host of the recombinant microorganism is preferably *Escherichia coli* or a lactic acid bacterium that is Et prokaryotic cell or yeast that is an eukaryotic cell, particularly preferably yeast.

When D-lactic acid is produced by the method of producing a chemical product according to the present invention, the gene encoding D-lactate dehydrogenase is preferably a gene derived from *Lactobacillus plantarum, Pediococcus acidilactici,* or *Bacillus laevolacticus,* more preferably a gene derived from *Bacillus laevolacticus*.

When D-lactic acid is produced by the method of producing a chemical product according to the present invention, the separation and purification of D-lactic acid contained in the filtered/separated fermentation liquor can be conducted by a combination of conventionally known methods such as concentration, distillation and crystallization. Examples thereof include a method that involves lowering the pH of the filtered/separated fermentation liquor to 1 or less and then extracting D-lactic acid with diethyl ether, ethyl acetate or the like, a method that involves adsorbing the fermentation liquor onto an ion-exchange resin, washing the resin, and eluting D-lactic acid, a method that involves reacting D-lactic acid in the fermentation liquor with an alcohol in the presence of an acid catalyst to convert it into the corresponding ester followed by distillation thereof, and a method that involves crystallizing D-lactic acid as a calcium salt or a lithium salt. Preferably, a concentrated D-lactic acid solution obtained by evaporating water from the filtered/separated fermentation liquor can be subjected to distillation when D-lactic acid is produced by the method of producing a chemical product according to the present invention. In distillation, the original solution to be distilled is subjected to distillation preferably while water is fed to it such that the water concentration of the solution is kept constant. An aqueous solution of D-lactic acid obtained by distillation can concentrated by evaporating water therefrom under heating to give an object concentration of purified D-lactic acid. When an aqueous solution of D-lactic acid containing low-boiling-point components (ethanol, acetic acid etc.) is obtained as a distillate, the low-boiling-point components are preferably removed in a step of concentrating D-lactic acid. After the distillation operation, the distillate can also be purified with an ion-exchange resin or activated charcoal, by chromatographic separation or the like as necessary to remove impurities, to give D-lactic acid of higher purity.

When ethanol is produced by the method of producing a chemical product according to the present invention, the microorganisms or cultured cells that can be used in production of ethanol are not limited as long as they are the microorganism or cultured cells that can produce pyruvic acid. The microorganisms or cultured cells that can be used in production of ethanol include, for example, microorganisms belonging to the genus *Saccharomyces*, genus *Kluyveromyces* and genus *Schizosaccharomyces*. Among them, *Saccharomyces cerevisiae, Kluyveromyces lactis* and *Schizosaccharomyces pombe* can be preferably used. Microorganisms belonging to the genus *Lactobacillus* and genus *Zymomonas* can also be preferably used. Among them, *Lactobacillus brevis* and *Zymomonas mobilis* can be preferably used.

The microorganisms or cultured cells that can be used in production of ethanol in the present invention may be microorganisms or cultured cells having an artificially increased ability to produce ethanol. Specifically, the microorganisms or cultured cells that can be used in production of ethanol in the present invention may be those having properties modified partially by mutation or genetic recombination. Examples of the microorganisms or cultured cells having partially modified properties include yeasts endowed with an ability to assimilate raw starch by integration of a glucoamylase gene derived from a mold belonging to the genus *Rhizopus* ("Biseibutsu (Microorganism)", 3:555-564 (1987)). A purification method using distillation or a concentration/purification method using NF, RO membrane, or zeolite separation membrane can be preferably used in separation and purification of ethanol contained in the filtered/separated fermentation liquor produced by the production method of the present invention.

When pyruvic acid is produced by the method of producing a chemical product according to the present invention, the microorganisms or cultured cells that can be used in production of pyruvic acid are not limited as long as they are microorganisms or cultured cells that can produce pyruvic acid. The microorganisms or cultured cells that can be preferably used in production of pyruvic acid include, for example, microorganisms belonging to the genus *Pseudomonas*, genus *Corynebacterium*, genus *Escherichia*, and genus *Acinetobacter*. More preferably, microorganisms such as *Pseudomonas fuluorescens, Pseudomonas aeruginosa* and *Escherichia coli* can be used. Recombinant microorganisms created by subjecting these microorganisms to mutation or genetic recombination to partially modify their properties may also be used. For example, those microorganisms in which an ATPase gene involved directly in production of ATP by oxidative phosphorylation was mutated or deleted are also preferably used. Molds and yeasts can also be preferably used. For example, molds and yeasts belonging to the genus *Saccharomyces*, genus *Toluropusis*, genus *Candida*, and genus *Schizophyllum* can be used. More preferably, molds and yeasts such as *Saccharomyces cerevisiae, Saccharomyces copsis, Candida glabrata, Candida lipolytica, Toluropusis glabrata,* and *Schizophyllum commune* can be used to produce pyruvic acid.

When pyruvic acid is produced by the method of producing a chemical product according to the present invention, the separation and purification of pyruvic acid contained in the filtered/separated fermentation liquor can be conducted by a method using an anion-exchange column. For example, a purification method using a weakly halophytic ion exchanger shown in JP-A No. 6-345683 can be preferably used.

When succinic acid is produced by the method of producing a chemical product according to the present invention, the microorganisms or cultured cells that can be used in production of succinic acid are not limited as long as they are microorganisms or cultured cells that can produce succinic acid. The microorganisms or cultured cells that can be preferably used in production of succinic acid include, for example, microorganisms belonging to the genera *Anaerobiospirillum* and *Actinobacillus*. Specific examples of such microorganisms include *Anaerobiospirillum succiniciproducens* described in U.S. Pat. No. 5,143,833 and *Actinobacillus succinogenes* disclosed by James B. Mckinlay, et al. (Appl. Microbiol. Biotechnol., 71, 6651-6656 (2005). *Coryneform* bacteria of the genera *Corynebacterium* and *Brevibacterium*, and *Escherichia*, can also be used. *Coryneform* bacteria are preferably *Corynebacterium glutamicum, Brevibacterium flavum,* and *Brevibacterium lactofermentum*.

The microorganisms may be those having a succinic acid production ability improved by genetic recombination, by which the productivity of succinic acid can be improved. Examples of the microorganisms that can be used herein include lactate dehydrogenase-deficient *Brevibacterium fla-* *vum* MJ233AB-41 (FERM BP-1498) described in JP-A No. 2005-27533, *Corynebacterium glutamicum* described in Non-Patent Document 1, and pyruvate formate lyase- and lactate dehydrogenase-deficient *Escherichia coli* AFP111 strains described in U.S. Pat. No. 5,770,435.

When succinic acid is produced by the method of producing a chemical product according to the present invention, a usual method of purifying succinic acid can be applied to separation and purification of succinic acid. For example, a purification method of combining hydrolysis electrodialysis treatment and vacuum concentration/crystallization shown in JP-A No. 2005-333886 can be preferably used.

When itaconic acid is produced by the method of producing a chemical product according to the present invention, the microorganisms or cultured cells that can be used in production of itaconic acid are not limited as long as they are microorganisms or cultured cells that can produce itaconic acid. The microorganisms or cultured cells that can be preferably used in production of itaconic acid include molds and yeasts. More preferably, molds belonging to the genus *Aspergillus* or genus *Ustilago*, or yeasts belonging to the genus *Candida* or genus *Rhodotorula*, are used in production of itaconic acid In particular, molds such as *Aspergillus terreus, Aspergillus itaconicus, Ustilago maydis, Ustilago cynodontis,* and *Ustilago rabenhorstina,* or *Candia Antarctica* can be preferably used in production of itaconic acid.

When itaconic acid is produced by the method of producing a chemical product according to the present invention, the separation and purification of itaconic acid can be conducted by using ultrafiltration and electrodialysis. For example, a method of purification by ultrafiltration and electrodialysis with a salt-type cation-exchange resin membrane shown—Japanese Patent Publication No. 50958 can be preferably used.

When 1,3-propanediol is produced by the method of producing a chemical product according to the present invention, the microorganisms or cultured cells that can be used in production of 1,3-propanediol are not limited as long as they are microorganisms or cultured cells that can produce 1,3-propanediol. The microorganisms or cultured cells that can be preferably used in production of 1,3-propanediol include, for example, wild-type strains such as microorganisms belonging to the genera *Klebsiella, Clostridium* and *Lactobacillus* having an ability to produce 1,3-propanediol from glycerol.

When 1,3-propanediol is produced by the method of producing a chemical product according to the present invention, the microorganism preferably contains (a) at least one gene encoding a polypeptide having a glycerol dehydratase activity; (b) at least one gene encoding a glycerol dehydratase reactivation factor; and (c) at least one gene encoding a nonspecific catalyst activity of converting 3-hydroxypropionaldehyde into 1,3-propanediol. In the present invention, the microorganism is particularly preferably a recombinant microorganism enabling production of 1,3-propanediol.

When 1,3-propanediol is produced by the method of producing a chemical product according to the present invention, the microorganism that has an ability to produce 1,3-propanediol from glycerol is preferably a recombinant microorganism selected from the group consisting of *Klebsiella, Clostridium, Lactobacillus, Cytrobacter, Enterobacter, Aerobacter, Aspergillus, Saccharomyces, Schizosaccharomyces, Zygosaccharomyces, Pichia, Kluyveromyces, Candida, Hansenula, Debaryomyces, Mucor, Torulopsis,*

*Methylobacter, Salmonella, Bacillus, Aerobacter, Streptomyces, Eschericia* and *Pseudomonas*, and is more preferably *Escherichia coli*.

When 1,3-propanediol is produced by the method of producing a chemical product according to the present invention, the recombinant microorganism is preferably modified to enable production of 1,3-propanediol efficiently from glucose. For example, the recombinant microorganism is preferably a recombinant microorganism that contains (a) at least one gene encoding a polypeptide having a glycerol-3-phosphate dehydrogenase-activity and (b) at least one gene encoding a polypeptide having a glycerol-3-phosphatase activity, and is more preferably a recombinant microorganism containing a gene in which a glycerol dehydratase reactivation factor is encoded by orfX and orfZ isolated from a dha regulon. The recombinant microorganism is still more preferably a recombinant microorganism deficient in glycerol kinase activity and/or glycerol dehydrogenase activity and/or triose phosphate isomerase activity.

When 1,3-propanediol is produced by the method of producing a chemical product according to the present invention, the separation and purification of 1,3-propanediol contained in the filtered/separated fermentation liquor can be conducted by concentration and crystallization. For example, a purification method using concentration under reduced pressure and recrystallization shown in JP-A No. 35785 can be preferably used.

When cadaverine is produced by the method of producing a chemical product according to the present invention, the microorganisms or cultured cells that can be used in production of cadaverine are not limited as long as they are microorganisms or cultured cells that can produce cadaverine. The microorganisms or cultured cells that can be preferably used in production of cadaverine include, for example, microorganisms having an enhanced enzyme activity of a lysine decarboxylase and/or a lysine cadaverine antiporter. The microorganisms are more preferably recombinant microorganisms in which genes encoding a lysine decarboxylase and/or a lysine cadaverine antiporter have been integrated. The recombinant microorganisms are still more preferably those in which one or more kinds of genes encoding a lysine decarboxylase have been integrated.

When cadaverine is produced by the method of producing a chemical product according to the present invention, the recombinant microorganisms are preferably *Escherichia coli* and *coryneform* bacteria, more preferably *coryneform* bacteria having a lysine decarboxylase activity and having at least one property selected from homoserine auxotrophy and S-(2-aminoethyl)-L-cysteine resistance. The microorganisms are more preferably those deficient in homoserine dehydrogenase activity, even preferably those made deficient in homoserine dehydrogenase activity by mutation with an inserted gene. In the present invention, the genus of *coryneform* bacteria is preferably at least one genus selected from the group consisting of the genera *Corynebacuterium* and *Brevibacterium*. The microorganism is more preferably *Corynebacuterium gulutamicum*.

When cadaverine is produced by the method of producing a chemical product according to the present invention, the separation and purification of cadaverine contained in the filtrated/separated fermentation liquor can be conducted by a combination of methods known in the art, such as concentration, distillation and crystallization. For example, a purification method using crystallization shown in JP-A No. 2004-222569 can be preferably used. Depending on the acid used in continuous culture, the product in the present invention can be used as a material of various polymers, and when the product is used as a polymer material requiring high purity, a purification method using crystallization is preferably used. When the pH of the culture is maintained with hydrochloric acid, cadaverine dihydrochloride can be recovered from the filtrate by a crystallization step. It is more preferable that the pH of the culture is maintained with a dicarboxylic acid during continuous culture, and from the filtrate, cadaverine dicarboxylate can be recovered by a crystallization step. The dicarboxylic acid is more preferably an aliphatic and/or aromatic dicarboxylic acid having two carboxyl groups only as its functional groups. The dicarboxylic acid is still more preferably adipic acid, sebacic acid, 1,12-dodecanedicarboxylic acid, succinic acid, isophthalic acid or terephthalic acid.

When a nucleic acid is produced by the method of producing a chemical product according to the present invention, microorganisms or cultured cells that can be used in production of a nucleic acid are not limited insofar as they are microorganisms capable of producing a nucleic acid. The microorganisms or cultured cells that can be used in production of a nucleic acid may be those inherently having a high nucleic acid producing ability separated from the natural world, or may be prokaryotic microorganisms having an artificially increased producing ability. Specifically, the microorganisms may be those having properties modified partially by mutation or genetic recombination.

Now, the modification to a part of properties is described. For efficient production of a nucleic acid, the nucleic acid should be biosynthesized, accumulated and released outside the microorganism. Accordingly, microorganisms or cultured cells efficiently producing a nucleic acid can be created by enhancement of an enzyme involved in a nucleic acid biosynthesis pathway, reduction in the activity of an enzyme involved in a nucleic acid decomposition pathway, and modifications to a protein involved in release of a nucleic acid from the microorganism or to a composition of a biological membrane.

Specifically, when inosine is produced, the modification to a part of properties is made such that an adenylosuccinate synthase activity is desirably made free or weak; an inosinate dehydrogenase activity is desirably free or weak; and a nuclosidase activity is desirably free or weak. When guanosine is produced, an adenylosuccinate synthase activity is desirably free or weak; a guanylate reductase activity is desirably free or weak; a nucleosidase activity is desirably free or weak; and a nucleotidase activity is desirably free or weak. When uridine is produced, an uridine phosphorylase activity is desirably free or weak. When cytidine is produced, a cytidine deaminase activity is desirably free or weak, and a homoserine dehydrogenase is desirably free or weak.

When a nucleic acid is produced by the method of producing a chemical product according to the present invention, the microorganisms or cultured cells that can be used therein are preferably *coryneform* bacteria and *Bacillus subtilis*. The *coryneform* bacteria include bacteria belonging to the genus *Corynebacterium*. The bacteria of the genus *Corynebacterium* that can be preferably used include *Corynebacterium glutamicum, Corynebacterium ammoniagenes, Corynebacterium guanofaciens*, and *Corynebacterium petrophilium*. *Bacillus subtilis* includes bacteria belonging to the genus *Bacillus*. Among those of the genus *Bacillus, Bacillus subtilis, Bacillus liqueniformis*, and *Bacillus pumilus* are preferably used. When guanosine is produced, the *coryneform* bacteria used herein include bacteria belonging to the genus *Corynebacterium*. Among those of the genus *Corynebacterium*, *Corynebacterium glutamicum* is preferable, and *Bacillus subtilis* includes bacteria belonging to the genus *Bacillus*]. Among those of the genus *Bacillus*, *Bacillus subtilis*, *Bacillus liqueniformis* and *Bacillus pumilus* are preferably used. When uridine is produced, *Bacillus subtilis* can be used, and among *Bacillus subtilis* bacteria, bacteria belonging to the genus *Bacillus* are preferably used. Among those of the genus *Bacillus*, *Bacillus subtilis* is preferably used. When cytidine is produced, *Bacillus subtilis* can be used, and among *Bacillus subtilis* bacteria, bacteria belonging to the genus *Bacillus* are preferably used. Among those of the genus *Bacillus*, *Bacillus subtilis* is preferably used.

When a nucleic acid is produced by the method of producing a chemical product according to the present invention, the separation and purification of a nucleic acid contained in the filtered/separated fermentation liquor can be conducted preferably by a combination of ion-exchange resin treatment, concentrating/cooling recrystallization, membrane separation and other methods. For removing impurities, conventional activated carbon adsorption and recrystallization may be used in purification.

When an amino acid is produced by the method of producing a chemical product according to the present invention, the microorganisms or cultured cells that can be used in production of an amino acid are not limited as long as they are microorganisms that can produce an amino acid. The microorganisms or cultured cells that can be used in production of an amino acid may be those originally having a high amino acid producing ability separated from the natural world or may be microorganisms or cultured cells having an artificially enhanced production ability. When an amino acid is produced by the method of producing a chemical product according to the present invention, the amino acid is preferably L-threonine, L-lysine, L-glutamic acid, L-tryptophan, L-isoleucine, L-glutamine; L-arginine, L-alanine, L-histidine, L-proline, L-phenylalanine, L-aspartic acid, L-tyrosine, methionine, serine, valine or leucine.

Now, the microorganisms or cultured cells that can be used in production of an amino acid are described about specific amino acids. When L-threonine is produced by the method of producing a chemical product according to the present invention, the microorganisms or cultured cells that can be used in production of L-threonine may be a microorganism belonging to a genus selected from the genus *Escherichia*, genus *Providencia*, genus *Corynebacterium*, genus *Brevibacterium* and genus *Serratia*. Among them, particularly preferable bacteria are *Escherichia coli*, *Providencia rettgeri*, *Corynebacterium glutamicum*, *Brevibacterium flavum*, *Brevibacterium lactofermentum*, and *Serratia marcescens*.

When L-lysine is produced by the method of producing a chemical product according to the present invention, the microorganisms or cultured cells that can be used in production of L-lysine are preferably *Corynebacterium glutamicum*, *Brevibacterium flavum*, and *Brevibacterium lactofermentum*. When L-glutamic acid is produced by the method of producing a chemical product according to the present invention, the microorganisms or cultured cells that can be used in production of L-glutamic acid are preferably *Corynebacterium glutamicum*, *Brevibacterium flavum*, and *Brevibacterium lactofermentum*.

When L-tryptophan is produced by the method of producing a chemical product according to the present invention, the microorganisms or cultured cells that can be used in production of L-tryptophan are preferably *Corynebacterium glutamicum*, *Brevibacterium flavum*, *Brevibacterium lactofermentum*, *Bacillus subtilis*, *Bacillus amyloliquefaciens*, and *Escherichia coli*.

When L-isoleucine is produced by the method of producing a chemical product according to the present invention, the microorganisms or cultured cells that can be used in production of L-isoleucine are preferably *Corynebacterium glutamicum*, *Brevibacterium flavum*, *Brevibacterium lactofermentum*, and *Serratia marcescens*.

When L-glutamine is produced by the method of producing a chemical product according to the present invention, the microorganisms or cultured cells that can be used in production of L-glutamine are preferably *Corynebacterium glutamicum*, *Brevibacterium flavum*, *Brevibacterium lactofermentum*, and *Flavobacterium rigense*.

When L-arginine is produced by the method of producing a chemical product according to the present invention, the microorganisms or cultured cells that can be used in production of L-arginine are preferably *Corynebacterium glutamicum*, *Brevibacterium flavum*, *Serratia marcescens*, *Escherichia coli* and *Bacillus subtilis*.

When L-alanine is produced by the method of producing a chemical product according to the present invention, the microorganisms or cultured cells that can be used in production of L-alanine are preferably *Brevibacterium flavum* and *Arthrobacter oxydans*.

When L-histidine is produced by the method of producing a chemical product according to the present invention, the microorganisms or cultured cells that can be used in production of L-histidine are preferably *Corynebacterium glutamicum*, *Brevibacterium flavum*, *Brevibacterium ammoniagenes*, *Serratia marcescens*, *Escherichia coli*, *Bacillus subtilis*, and *Streptomyces coelicolor*.

When L-proline is produced by the method of producing a chemical product according to the present invention, the microorganisms or cultured cells that can be used in production of L-proline are preferably *Corynebacterium glutamicum*, *Kurthia catenaforma*, *Serratia marcescens*, and *Escherichia coli*.

When L-phenylalanine is produced by the method of producing a chemical product according to the present invention, the microorganisms or cultured cells that can be used in production of L-phenylalanine are preferably *Corynebacterium glutamicum*, *Brevibacterium flavum*, *Brevibacterium lactofermentum*, and *Escherichia coli*.

When L-aspartic acid is produced by the method of producing a chemical product according to the present invention, the microorganisms or cultured cells that can be used in production of L-aspartic acid are preferably *Brevibacterium flavum*, *Bacillus megatherium*, *Escherichia coli*, and *Pseudomonas fluorescens*.

When L-tyrosine is produced by the method of producing a chemical product according to the present invention, the microorganisms or cultured cells that can be used in production of L-tyrosine are preferably *Corynebacterium glutamicum*, *Brevibacterium flavum*, *Brevibacterium lactofermentum*, and *Escherichia coli*.

When methionine is produced by the method of producing a chemical product according to the present invention, the microorganisms or cultured cells that can be used in production of methionine are preferably *Corynebacterium glutamicum*.

When serine is produced by the method of producing a chemical product according to the present invention, the microorganisms or cultured cells that can be used in production of serine are preferably *Corynebacterium glutami-* cum, *Brevibacterium flavum, Brevibacterium lactofermentum*, and *Arthrobacter oxydans*.

When valine is produced by the method of producing a chemical product according to the present invention, the microorganisms or cultured cells that can be used in production of valine are preferably *Brevibacterium lactofermentum, Serratia marcescens*, and *Klebsiella pneumoniae*.

When leucine is produced by the method of producing a chemical product according to the present invention, the microorganisms or cultured cells that can be used in production of leucine are preferably *Corynebacterium glutamicum, Brevibacterium lactofermentum*, and *Serratia marcescens*.

When an amino acid is produced by the method of producing a chemical product according to the present invention, the microorganisms or cultured cells that can be used in production of an amino acid may be microorganisms or cultured cells derived from the exemplary microorganisms or cultured cells by artificially increasing their ability to produce an amino acid. The microorganisms or cultured cells that can be used in production of an amino acid may be those having properties partially modified by mutation or genetic recombination. Examples of the microorganisms or cultured cells having partially modified properties which can be used in production of an amino acid include *Providencia rettgeri* with improvement in L-threonine productivity described in JP-A No. 2-219582 and *Corynebacterium glutamicum* with improvement in L-alanine productivity described in Japanese Patent Application National Publication No. 3-500486.

When continuous fermentation is conducted by the method of producing a chemical product according to the present invention, a higher volume production rate than that in conventional batch fermentation can be attained to enable extremely efficient fermentation production. The production rate in continuous fermentation is calculated using the following equation (3):

[Equation 3]

Fermentation production rate(g/$L$/hr)=concentration of a product in withdrawn liquor(g/$L$)×rate of withdrawal of fermentation liquor($L$/hr)+amount of running liquor of the apparatus($L$)     (3)

The fermentation production rate in batch culture is determined by dividing the amount (g) of a product upon consumption of all the starting carbon source by the time (h) required for consumption of the carbon source and the amount (L) of a culture liquid at that time.

Now, the continuous fermentation apparatus of the present invention is described. The continuous fermentation apparatus of the present invention can be used in production of alcohols such as ethanol, 1,3-propanediol, 1,4-butanediol and glycerol, organic acids such as acetic acid, lactic acid, pyruvic acid, succinic acid, malic acid, itaconic acid and citric acid, amino acids such as L-threonine, L-lysine, L-glutamic acid, L-tryptophan, L-isoleucine, L-glutamine, L-arginine, L-alanine, L-histidine, L-proline, L-phenylalanine, L-aspartic acid, L-tyrosine, methionine, serine, valine and leucine, nucleic acids such as inosine and guanosine, diamine compounds such as cadaverine, enzymes, antibiotics, and recombinant proteins.

The continuous fermentation apparatus of the present invention is an apparatus for producing a chemical product through continuous fermentation which includes filtering a fermentation culture of a microorganism or cultured cells with a separation membrane to recover a product from a filtrate and simultaneously retaining a nonfiltered fluid in, or refluxing it to, the fermentation culture, and adding fermentation materials to the fermentation culture.

The continuous fermentation apparatus of the present invention has a fermentation reaction tank for fermentation culture of a microorganism or cultured cells.

In one form, the continuous fermentation apparatus of the present invention includes a membrane separation tank for filtration of the fermentation culture, which is connected via fermentation culture circulating means to the fermentation reaction tank and provided therein with a separation membrane; and leans for regulating the transmembrane pressure difference of the separation membrane in the range of 0.1 to 20 kPa, wherein the separation membrane is a porous membrane having an average pore size of 0.01 µm or more to less than 1 µm.

In another form, the continuous fermentation apparatus of the present invention includes a separation membrane element for filtration of the fermentation culture, which is arranged in the inside of the fermentation reaction tank and provided therein with a separation membrane; means for discharging a filtered fermentation product, which is connected to the separation membrane element; and means for regulating the transmembrane pressure difference of the separation membrane in the range of 0.1 to 20 kPa, wherein the separation membrane is a porous membrane having an average pore size of 0.01 µm or more to less than 1 µm.

In the continuous fermentation apparatus of the present invention, the purified-water permeability coefficient of the porous membrane is preferably $2\times10^{-9}$ m$^3$/m$^2$/s/Pa or more to $6\times10^{-7}$ m$^3$/m$^2$/s/Pa or less.

In the continuous fermentation apparatus of the present invention, it preferable that the average pore size of the porous membrane is 0.01 µm or more to less than 0.2 µm, and the standard deviation of the pore size of the porous membrane is 0.1 µm or less.

In the continuous fermentation apparatus of the present invention, the porous membrane is preferably a porous membrane having a surface roughness of 0.1 µm or less.

In the continuous fermentation apparatus of the present invention, the porous membrane is preferably a porous membrane containing a porous resin layer. In the continuous fermentation apparatus of the present invention, the porous resin layer is preferably a porous resin layer made of an organic polymer. In the continuous fermentation apparatus of the present invention, the material of the organic polymer membrane is more preferably polyvinylidene fluoride.

Now, the continuous fermentation apparatus used in the method of producing a chemical product according to the present invention is described by reference to the drawings.

FIG. 1 is a schematic side view for showing one example of the membrane separation-type continuous fermentation apparatus used in the method of producing a chemical product according to the present invention. FIG. 1 is a typical example of the apparatus wherein a separation membrane element is arranged outside a fermentation reaction tank.

In FIG. 1, the membrane separation-type continuous fermentation apparatus is composed essentially of a fermentation reaction tank 1, a membrane separation layer 12, and a water head difference regulating apparatus 3. The separation membrane element 2 includes a porous membrane integrated therein. This separation membrane element preferably use, for example, a separation membrane and a separation membrane element disclosed in International Publication No. 2002/064240. The membrane separation tank 12 is connected via a fermentation liquor circulating pump 11 to the fermentation reaction tank 1.

In FIG. 1, a medium is introduced by a medium feeding pump 7 into the fermentation reaction tank 1, and if necessary, the fermentation liquor in the fermentation reaction tank 1 is stirred with an agitator 5, and if necessary, a necessary gas can be fed via a gas feeding apparatus 4. At this time, a fed gas may be recovered, recycled and fed again via the gas feeding apparatus 4. If necessary, the pH of the fermentation liquor is regulated with a pH sensor/regulating apparatus 9 and a pH regulating solution feeding pump 8, and if necessary, the temperature of the fermentation liquor is regulated by a temperature regulator 10, whereby highly productive fermentation production can be conducted. The fermentation liquor in the apparatus circulates between the fermentation reaction tank 1 and the membrane separation tank 12 by the fermentation liquor circulating pump 11. The fermentation liquor containing a fermentation product is filtered and separated by the separation membrane element 2 into microorganisms and a fermentation product which can then be taken out from the apparatus system. The filtered/separated microorganisms can remain in the apparatus system thereby attaining a high density of microorganisms in the apparatus to achieve highly productive fermentation production. Filtration/separation by the separation membrane element 2 is achieved by a water head pressure difference from the water surface of the membrane separation tank 12, thus requiring no special power. As necessary, the filtration/separation rate with the separation membrane element 2 and the amount of the fermentation liquor in the apparatus can be appropriately controlled with the level sensor 6 and the water head pressure difference regulating apparatus 3. As necessary, a necessary gas can be fed via the gas feeding apparatus 4 into the membrane separation tank 12. The fed air can be recovered, recycled and fed again via the gas feeding apparatus 4. Filtration/separation by the separation membrane element 2 can also be achieved by suction filtration with a pump or the like or b pressurization in the apparatus system. Microorganisms or cultured cells may be cultured continuously in a culture tank and fed as necessary to the fermenter. By culturing the microorganisms or cultured cells in a culture tank and feeding them as necessary to the fermenter, continuous fermentation with always fresh microorganisms or cultured cells having a high ability to produce a chemical product is made feasible to enable continuous fermentation with high productive performance kept for a long time.

Figure 2:
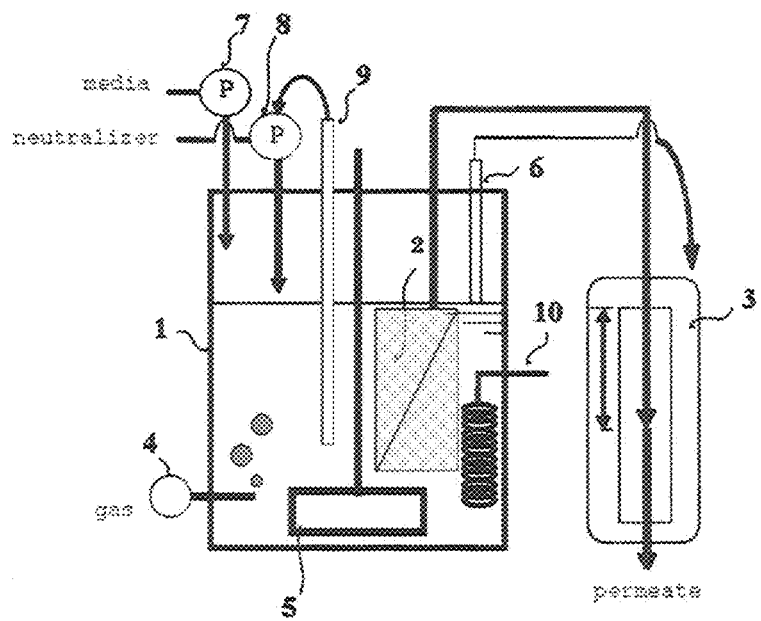
FIG. 2 is a schematic side view for showing another example of the membrane separation-type continuous fermentation apparatus used in the present invention.

FIG. 2 is a schematic side view for explaining another example of the membrane separation-type continuous fermentation apparatus used in the present invention. A typical example of the continuous fermentation apparatus wherein a separation membrane element is arranged inside the fermentation reaction tank, used in the method of producing a chemical product according to the present invention, is shown in the schematic view in FIG. 2.

In FIG. 2, the membrane separation-type continuous fermentation apparatus is composed essentially of a fermentation reaction tank 1 and a water head difference regulating apparatus 3. A porous membrane is integrated in a separation membrane element 2 in the fermentation reaction tank 1. This porous membrane can use, for example, a separation membrane and a separation membrane element disclosed in International Publication No. 2002/064240. The separation membrane element will be described later in more detail.

Then, continuous fermentation in the membrane separation-type continuous apparatus in FIG. 2 is described in detail.

A medium is introduced continuously or intermittently via a medium feeding pump 7 into the fermentation reaction tank 1. If necessary, the medium may have been sterilized by heating or subjected to sterilization with a filter before introduction into the fermentation reaction tank. During fermentation production, the fermentation liquor in the fermentation reaction tank 1 is stirred if necessary with an agitator 5 in the fermentation reaction tank 1. At the time of fermentation production, a necessary gas can be fed if necessary via a gas feeding apparatus 4 to the fermentation reaction tank 1. At the time of fermentation production, the pH of the fermentation liquor in the fermentation reaction tank 1 is regulated if necessary with a pH sensor/regulating apparatus 9 and a pH regulating solution feeding pump 8, and the temperature of the fermentation liquor in the fermentation reaction tank 1 is regulated if necessary by a temperature regulator 10, whereby highly productive fermentation production can be conducted. In this example, pH and temperature are illustrated as physicochemical conditions of the fermentation liquor to be regulated with measuring apparatuses and control apparatuses, but if necessary, dissolved oxygen or ORP can be regulated, or the concentration of a chemical product in the fermentation liquor is measured with an analyzer such as an on-line chemical sensor, and physicochemical conditions can be regulated by using, as an indicator, the concentration of a chemical product in the fermentation liquor. In continuous or intermittent introduction of the medium, it is preferable that the amount and rate of the medium introduced are regulated appropriately by using, as an indicator, a certain measurement value in the physicochemical environment of the fermentation liquor with the measurement apparatus.

In FIG. 2, the fermentation liquor is filtered and separated into microorganisms and a fermentation product by a separation membrane element 2 installed in the fermentation reaction tank 1, and the fermentation product can be taken out from the apparatus system. The filtered/separated microorganisms remain in the apparatus system thereby attaining a high density of the microorganisms in the apparatus system to achieve highly productive fermentation production. Filtration/separation with the separation membrane element 2 can be achieved by a water head pressure difference from the water surface of the fermentation reaction tank 1, thus requiring no special power. As necessary, the filtration/separation rate with the separation membrane element 2 and the amount of the fermentation liquor in the fermentation reaction tank 1 can be appropriately controlled with a level sensor 6 and a water head pressure difference regulating apparatus 3. Filtration/separation by the separation membrane element can also be attained by suction filtration with a pump or the like or by pressurization in the apparatus system, if necessary. Microorganisms or cultured cells may be cultured in a culture tank and fed as necessary to the fermenter. By culturing microorganisms or cultured cells in a culture tank and feeding them as necessary to the fermenter, continuous fermentation with always fresh microorganisms or cultured cells having a high ability to produce a chemical product is made feasible to enable continuous fermentation with high productive performance kept for a long time.

Now, the separation membrane element used preferably in the continuous fermentation apparatus used in the method of producing a chemical product according to the present invention is described.

Figure 3:
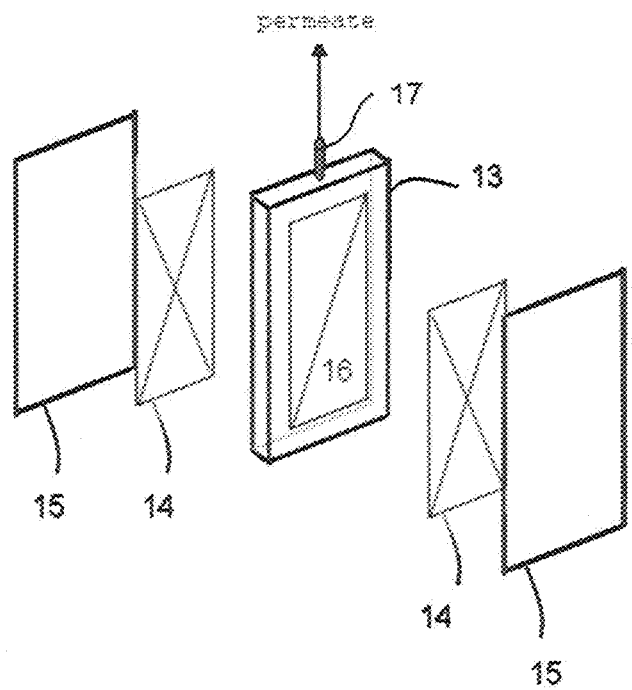
FIG. 3 is a schematic perspective view for showing one example of the separation membrane element used in the present invention.

The separation membrane element shown in FIG. 3 is described. A separation membrane and a separation membrane element disclosed in International Publication No. 2002/064240 can be preferably used in the continuous fermentation apparatus used in the method of producing a chemical product according to the present invention. As shown in FIG. 3, the separation membrane element is constituted by arranging a passage material 14 and the separation membrane 15 in this order on both sides of a support plate 13 having rigidity. The support plate 13 has a concave part 16 on both sides thereof. The separation membrane 15 filters the fermentation liquor. By the passage material 14, permeated water filtered through the separation membrane 15 is flowed efficiently to the support plate 13. The permeated water flowed to the support plate 13 passes through the concave part 16 of the support plate 13 and discharged via a water collecting pipe 17 to the outside of the fermentation culture tank. The power for discharging the permeated water can be generated by a method using a water head pressure difference, suction filtration with a pump, a liquid, a gas or the like, or pressurization in the apparatus.

Figure 4:
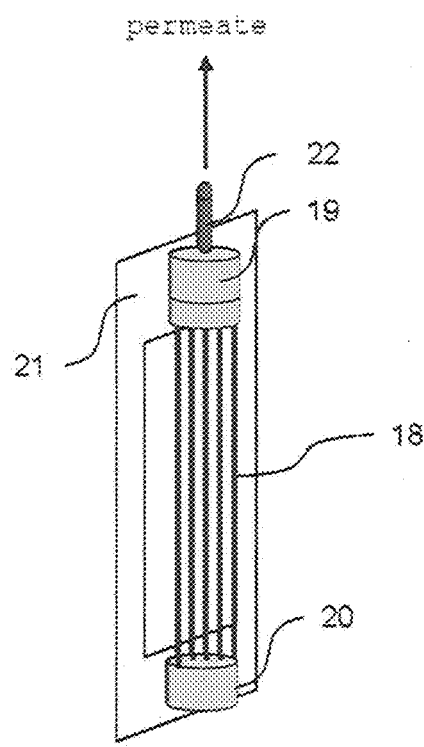
FIG. 4 is a cross-sectional view for showing another example of the separation membrane element used in the present invention.

Now, the separation membrane element shown in FIG. 4 is described. As shown in FIG. 4, the separation membrane element is composed essentially of separation membrane bundles 18 composed of hollow fiber membranes, an upper resin sealing layer 19, and a lower resin sealing layer 20. The separation membrane bundle is bonded and fixed in the form of a bundle by the upper resin sealing layer 19 and the lower resin sealing layer 20. By bonding/fixation with the lower resin sealing layer, the hollow of the hollow fiber membrane is sealed to prevent leakage of the fermentation culture. On the other hand, the upper resin sealing layer 19 does not seal the inner hole of the hollow fiber membrane, to allow permeated water to flow to the water collecting pipe 22. This separation membrane element can be arranged via a support frame 21 in the continuous fermentation apparatus. The permeated water filtered through the separation membrane bundle 18 passes through the hollow of the hollow fiber membrane and discharged via the water collecting pipe 22 to the outside of the fermentation culture tank. The power for discharging the permeated water can be generated by a method using a water head pressure difference, suction filtration with a pump, a liquid, a gas or the like, or pressurization in the apparatus.

The material constituting the separation membrane element of the continuous fermentation apparatus used in the method of producing a chemical product according to the present invention is preferably a member resistant to high-pressure steam sterilization. If the inside of the fermentation apparatus can be sterilized, contamination with unfavorable microorganisms can be prevented during continuous fermentation, to enable more stable continuous fermentation. The member constituting the separation membrane element is preferably resistant to the conditions (121° C., 15 minutes) of high-pressure steam sterilization. The material of the separation membrane element member can be appropriately selected from, for example, metals such as stainless steel and aluminium and resins such as polyamide resin, fluorine resin, polycarbonate resin, polyacetal resin, polybutylene terephthalate resin, PVDF, modified polyphenylene ether resin and polysulfone resin.

In the continuous fermentation apparatus used in the method of producing a chemical product according to the present invention, the separation membrane element may be installed outside the fermentation tank or may be installed inside the fermentation tank. In the case of installation outside the fermentation tank, the separation membrane element may be installed in a separately arranged membrane separation tank to circulate the fermentation liquor between the fermentation tank and the membrane separation tank, during which the fermentation liquid can be continuously filtered through the separation membrane element.

In the continuous fermentation apparatus used in the method of producing a chemical product according to the present invention, the membrane separation tank is desirably capable of high-pressure steam sterilization. If the membrane separation tank is capable of high-pressure steam sterilization, contamination due to saprophytic bacteria can be easily prevented.

EXAMPLES

Hereinafter, in order to explain the present invention in more detail, specific embodiments in which D-lactic acid, ethanol, pyruvic acid, succinic acid, 1,3-propanediol, itaconic acid, cadaverine, a nucleic acid, and an amino acid were selected as the chemical product, and a microorganism or cultured cells having an ability to product each chemical product were used in continuous fermentation using the apparatuses shown in the schematic views in FIGS. 1 and 2, are described by reference to the Examples.

Reference Example 1

Preparation of a Yeast Strain Having an Ability to Produce L-Lactic Acid

A yeast strain having an ability to produce L-lactic acid was created in the following manner. A human-derived LDH gene was ligated downstream from a PDC1 promoter on yeast genome thereby creating a yeast strain having an ability to produce L-lactic acid. Polymerase chain reaction (PCR) was carried out using La-Taq (Takara Shuzo Co., Ltd.) or KOD-Plus-polymerase (TOYOBO CO., LTD.) according to its attached instructions.

After an established cell line of human breast cancer (MCF-7) was cultured and recovered, the total RNA was extracted using TRIZOL Reagent (Invirogen). Using the resulting total RNA as a template, reverse transcription reaction was carried out using SuperScript Choice System (Invitrogen), to synthesize cDNA. Details of the operation were in accordance with protocols attached thereto. The cDNA thus obtained was used as an amplification template for subsequent PCR.

Figure 5:
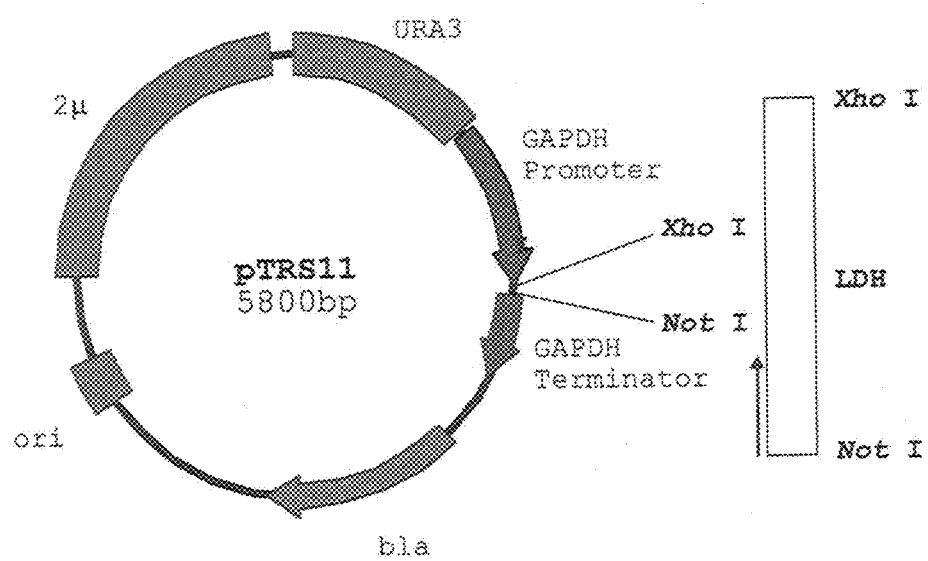
FIG. 5 shows a physical map of yeast expression vector pTRS11.

An L-ldh gene was cloned by PCR with KOD-Plus-polymerase and a primer set of oligonucleotides set forth in SEQ ID NOS: 1 and 2 wherein the cDNA obtained by the above operation was used as an amplification template. Each PCR amplification fragment was purified, then phosphorylated at its terminus with a T4 polynucleotide kinase (manufactured by TAKARA) and ligated to pUC118 vector (which had been treated by cleavage with a restriction enzyme HincII and then subjecting the cleavage surface to dephosphorylation). This ligation was conducted with DNA Ligation Kit Ver. 2 (manufactured by TAKARA). The ligation plasmid product was used to transform Escherichia coli DH5α from which plasmid DNA was then recovered to give plasmids wherein various L-ldh genes (SEQ ID NO: 3) had been subcloned. The resulting pUC118 plasmids into which the L-ldh gene had been inserted were digested with restriction enzymes XhoI and NotI, and each of the resulting DNA fragments was inserted into an XhoI/NotI cleavage site of yeast expression vector pTRS11 (FIG. 5). Human-derived L-ldh gene expression plasmid pL-ldh5 (L-ldh gene) was obtained in this manner. The above-mentioned pL-ldh5 that is a human-derived L-ldh gene expression vector was deposited as a plasmid alone under FERM AP-20421 on Feb. 21, 2005 with International Patent Organism Depositary (IPOD), National Institute of Advanced Industrial Science and technology (AIST) (Central 6, 1-1-1 Higashi, Tsukuba City, Ibaraki Pref., Japan).

A 1.3-kb DNA fragment containing the human-derived LDH gene and a terminator sequence of TDH3 gene derived from *Saccharomyces cerevisiae* was amplified by PCR with a primer set of oligonucleotides set forth in SEQ ID NOS: 4 and 5 wherein the plasmid pL-ldh5 containing the human-derived LDH gene was used as an amplification template. A 1.2-kb DNA fragment containing a TRP1 gene derived from *Saccharomyces cerevisiae* was amplified by PCR with a primer set of oligonucleotides set forth in SEQ ID NOS: 6 and 7 and plasmid pRS424 as an amplification template. The respective DNA fragments were separated by 1.5% agarose gel electrophoresis and purified in a usual manner. A mixture of the 1.3-kb and 1.2-kb fragments thus obtained was used as an amplification template in PCR with a primer set of oligonucleotides set forth in SEQ ID NOS: 4 and 7 to give products which were then subjected to 1.5% agarose gel electrophoresis to prepare a 2.5-kb DNA fragment consisting of the human-derived LDH gene and the TRP1 gene ligated therein in a usual manner. This 2.5-kb DNA fragment was transformed in a usual manner into a budding yeast NBRC10505 strain thereby rendering it tryptophan non-auxotrophic.

The fact that the resulting transformed cells were those cells that have the human-derived LDH gene ligated downstream of a PDC1 promoter on yeast genome was confirmed by first preparing the genome DNA of the transformed cell in a usual manner and using it as an amplification template in PCR with a primer set of oligonucleotides set forth in SEQ ID NOS: 8 and 9 to give a 0.7-kb amplification DNA fragment. Whether the transformed cells have an ability to produce lactic acid was confirmed by determining, in HPLC under the following conditions, as amount of lactic acid contained in a culture supernatant of the transformed cells cultured in an SC medium (METHODS IN YEAST GENETICS 2000 EDITION, CSHL PRESS).

Column: Shim-Pack SPR-H (manufactured by Shimadzu Corporation)
Mobile phase: 5 mM p-toluenesulfonic acid (flow rate 0.8 mL/min)
Reaction solution: 5 mM p-toluenesulfonic acid, 20 mM Bis-Tris, 0.1 mM EDTA•2 Na (flow rate 0.8 mL/min)
Detection method: electric conductivity
Temperature: 45° C.

The optical purity of L-lactic acid was measured by HPLC under the following conditions.
Column: TSK-gel Enantio L1 (manufactured by Tosoh Corporation)
Mobile phase: 1 mM aqueous copper sulfate solution
Flow rate: 1.0 ml/min
Detection method: UV 254 nm
Temperature: 30° C.

The optical purity of L-lactic acid is calculated using the following equation:

Optical purity (%)=100×(L−D)/(L+D)

wherein L represents the concentration of L-lactic acid, and D represents the concentration of D-lactic acid.

As a result of HPLC analysis, 4 g/L L-lactic acid was detected, and D-lactic acid was below the limit of detection. From the above study, this transformant was confirmed to have an ability to produce L-lactic acid. The resulting transformed cells were used as yeast SW-1 strain in the Examples below.

Reference Example 2

Preparation of a Porous Membrane (No. 1)

A polyvinylidene fluoride (PVDF) resin and N,N-dimethylacetamide were used as a resin and solvent respectively and stirred sufficiently at a temperature of 90° C. to give a stock solution having the following composition:
Polyvinylidene fluoride: 13.0% by weight, and
N,N-Dimethylacetamide: 87.0% by weight Then, the stock solution was cooled to a temperature of 25° C., then applied onto a polyester fiber nonwoven fabric having a density of 0.48 g/cm$^3$ and a thickness of 220 μm attached previously to a glass plate, and was immediately dipped for 5 minutes in a coagulation bath at a temperature of 25° C. having the following composition, to give a porous base material having a porous resin layer formed thereon.
Water: 30.0% by weight
N,N-Dimethylacetamide: 70.0% by weight This porous base material was detached from the glass plate, dipped 3 times in hot water at a temperature of 80° C., thereby being washed to remove N,N-dimethylacetamide, to give a separation membrane.

The surface of the porous resin layer, in an area of 9.2 μm×10.4 μm, was observed at 10,000-fold magnification under a scanning electron microscope. The average diameter of all observable pores was 0.1 μm.

Then, the separation membrane was evaluated for its purified-water permeability coefficient. Measurement of the purified-water permeability coefficient was conducted with reverse osmosis membrane-treated purified water at 25° C. with a head height of 1 m.

The standard deviation of the average pore size was 0.035 μm and the surface roughness of the membrane was, 0.06 μm. The porous membrane thus prepared could be preferably used in the present invention.

Reference Example 3

Preparation of a Porous Membrane (No. 2)

A polyvinylidene fluoride (PVDF) resin was used as resin, polyethylene glycol (PEG) having a molecular weight of about 20,000 as a pore-forming agent, N,N-dimethylacetamide as solvent, and purified water as non-solvent, and these materials were stirred sufficiently at a temperature of 90° C. to give a stock solution having the following composition:
Polyvinylidene fluoride: 13.0% by weight
Polyethylene glycol: 5.5% by weight
N,N-Dimethylacetamide: 78.0% by weight, and
Purified water: 3.5% by weight.

Then, the stock solution was cooled to a temperature of 25° C., then applied onto a polyester fiber nonwoven fabric having a density of 0.48 g/cm$^3$ and a thickness of 220 μm, immediately dipped for 5 minutes in purified water at 25° C., dipped 3 times in hot water at 80° C., thereby being washed to remove N,N-dimethylacetamide and polyethylene glycol to give a separation membrane.

The surface of the porous resin layer in an area of 9.2 μm×10.4 μm at the side of the separation membrane to which the stock solution had been applied was observed at 10,000-fold magnification under a scanning electron microscope. The average diameter of all observable pores was 0.02 μm.

The separation membrane was evaluated for its purified-water permeability coefficient. The purified-water permeability coefficient was 2×10⁻⁹ m³/m²·s·Pa. Measurement of the purified-water permeability coefficient was conducted with reverse osmosis membrane-treated purified water at 25° C. with a head height of 1 m.

The standard deviation of the average pore size was 0.0055 μm and the surface roughness of the membrane was 0.1 μm. The porous membrane thus prepared could be preferably used in the present invention.

Reference Example 4

Preparation of a Porous Membrane (No. 3)

A separation membrane was obtained in the same manner as in Reference Example 3 except that a stock solution having the following composition was used.
Polyvinylidene fluoride: 13.0% by weight
Polyethylene glycol: 5.5% by weight
N,N-Dimethylacetamide: 81.5% by weight.

The surface of the porous resin layer in an area of 9.2 μm×10.4 μm at the side of the separation membrane to which the stock solution had been applied was observed at 10,000-fold magnification under a scanning electronmicroscope. The average diameter of all observable pores was 0.19 μm.

The evaluated purified-water permeability coefficient of this separation membrane was 100×10⁻⁹ m³/m²·s·Pa. Measurement of the purified-water permeability coefficient was conducted with reverse osmosis membrane-treated purified water at 25° C. with a head height of 1 m.

The standard deviation of the average pore size was 0.060 μm and the surface roughness of the membrane was 0.08 μm. The porous membrane thus prepared could be preferably used in the present invention.

Reference Example 5

Preparation of a Porous Membrane (No. 4)

A polyvinylidene fluoride (PVDF) resin and N,N-dimethylacetamide were used as resin and solvent respectively and stirred sufficiently at a temperature of 90° C. to give a stock solution having the following composition:
Polyvinylidene fluoride: 15.0% by weight, and
N,N-Dimethylacetamide: 85.0% by weight Then, the stock solution was cooled to a temperature of 25° C., then applied onto a polyester fiber nonwoven fabric having a density of 0.48 g/cm³ and a thickness of 220 μm attached previously to a glass plate, and was immediately dipped for 5 minutes in a coagulation bath at a temperature of 25° C. having the following composition, to give a porous base material having a porous resin layer formed thereon.
Water: 100.0% by weight This porous base material was detached from the glass plate, dipped 3 times in hot water at a temperature of 80° C., thereby being washed to remove N,N-dimethylacetamide, to give a separation membrane. The surface of the porous resin layer, in an area of 9.2 μm×10.4 μm, was observed at 10,000-fold magnification under a scanning electron microscope. The average diameter of all observable pores was 0.008 μm. The evaluated purified-water permeability coefficient of this separation membrane was 0.3×10⁻⁹ m³/m²·s·Pa. Measurement of the purified-water permeability coefficient was conducted with reverse osmosis membrane-treated purified water at 25° C. with a head height of 1 m.

The standard deviation of the average pore size was 0.002 μm and the surface roughness of the membrane was 0.06 μm.

Example 1

Production of L-Lactic Acid by Continuous Fermentation Using Yeast (No. 1)

Production of L-lactic acid was conducted by using the membrane separation-type continuous fermentation apparatus in FIG. 1 and a yeast lactic acid fermentation medium having the composition shown in Table 1. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in Example 1 are as follows:
Reaction tank capacity: 2 (L)
Membrane separation tank capacity: 0.5 (L)
Used separation membrane: polyvinylidene fluoride filtration membrane
Membrane separation element effective filtration area: 60 cm²
Temperature control: 30 (° C.)
Reaction tank aeration: 0.05 (L/min)
Membrane separation tank aeration: 0.3 (L/min)
Reaction tank agitation rate: 100 (rpm)
pH adjustment: adjusted to pH 5 with 1N NaOH
Lactic acid fermentation medium feed rate: variable control in the range of 50 to 300 ml/hr.
Amount of circulating liquid with a fermentation liquor circulating apparatus: 0.1 (L/min)
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and
200 hours to 300 hours: regulated at 0.1 kPa or more to 20 kPa or less)

Yeast SW-1 created in Reference Example 1 was used as the microorganism, a lactic acid fermentation medium having the composition shown in Table 1 was used as the medium, the concentration of lactic acid as a product was evaluated by HPLC shown in Reference Example 1, and the concentration of glucose was measured with Glucose Test Wako C (Wako Pure Chemical Industries, Ltd.).

TABLE 1

| Yeast lactic acid fermentation medium | |
|---|---|
| Glucose | 100 g |
| Yeast Nitrogen base w/o amino acid (Difco) | 6.7 g |
| Standard 19 amino acids excluding leucine | 152 mg |
| Leucine | 760 mg |
| Inositol | 152 mg |
| p-Aminobenzoic acid | 16 mg |
| Adenine | 40 mg |
| Uracil | 152 mg |

Unit (1/Liter)

First, the SW-1 strain was shake-cultured overnight in 5 ml of a lactic acid fermentation medium in a test tube (prior preliminary preculture). The resulting culture was inoculated into 100 ml of a fresh lactic acid fermentation medium and shake-cultured for 24 hours at 30° C. in a 500-ml Sakaguchi flask (preliminary preculture). The preliminary preculture was inoculated into 1.5 L of a lactic acid fermentation medium in the membrane separation-type continuous fermentation apparatus shown in FIG. 1, a reaction tank 1 was stirred with an agitator 5 attached thereto, followed by the aeration regulation, temperature control, and pH adjustment of the reaction tank 1, and without operating a fermentation liquor circulating pump 10, the microorganism was cultured for 24 hours (preculture). Immediately after preculture was finished, the fermentation liquor circulating pump 10 was operated, and the microorganism was continuously cultured under the conditions where in addition to the operation conditions at the time of preculture, a membrane separation tank 2 was aerated, a lactic acid fermentation medium was continuously fed, and the amount of membrane permeation water was regulated such that the amount of the fermentation liquor in the membrane separation-type continuous fermentation apparatus became 2 L, whereby L-lactic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of L-lactic acid produced in the membrane permeation fermentation liquor and the residual glucose concentration were measured at an appropriate time.

The results in the continuous fermentation test for 300 hours are shown in Table 2. Production of L-lactic acid by stable continuous fermentation was feasible by the method of producing a chemical product according to the present invention by using the membrane separation-type continuous fermentation apparatus in FIG. 1. The transmembrane pressure difference fluctuated within 2 kPa in the whole period of continuous fermentation.

Example 2

Production of L-Lactic Acid by Continuous Fermentation Using Yeast (No. 2)

The same L-lactic acid continuous fermentation test as in Example 1 was conducted by using the porous membrane in Reference Example 3 as a separation membrane. The results are shown in Table 2. As a result, stable production of L-lactic acid by continuous fermentation was feasible. The transmembrane pressure difference fluctuated within 2 kPa in the whole period of continuous fermentation.

Example 3

Production of L-Lactic Acid by Continuous Fermentation Using Yeast (No. 3)

The same L-lactic acid continuous fermentation test as in Example 1 was conducted by using the porous membrane in Reference Example 4 as a separation membrane. The results are shown in Table 2. As a result, stable production of L-lactic acid by continuous fermentation was feasible. The transmembrane pressure difference fluctuated within 2 kPa in the whole period of continuous fermentation.

Example 4

Production of L-Lactic Acid by Continuous Fermentation Using Yeast (No. 4)

Production of L-lactic acid was conducted by using the continuous fermentation apparatus in FIG. 2 and a yeast fermentation medium having the composition shown in Table 1. The medium was used after high-pressure steam sterilization (121° C., 15 minutes). As the separation membrane element material, a molding of stainless steel and polysulfone resin was used. As the separation membrane, the porous membrane prepared in Reference Example 1 was used. Unless otherwise noted, the operation conditions in this example are as follows:
Reaction tank capacity: 0.2 (L)
Used separation membrane: polyvinylidene fluoride filtration membrane
Membrane separation element effective filtration area: 120 $cm^2$
Temperature control: 30 (° C.)
Fermentation reaction tank aeration: 0.05 (L/min)
Lactic acid fermentation medium feed rate: variable control in the range of 50 to 300 ml/hr.
Fermentation reaction tank agitation rate: 800 (rpm)
pH adjustment: adjusted to pH 5 with 1 N NaOH
Regulation of the amount of membrane permeation water: flow rate regulation by transmembrane pressure difference (From start of continuous fermentation to 80 hours: regulated at 0.1 kPa or more to 5 kPa or less,
80 hours to 160 hours: regulated at 0.1 kPa or more to 2 kPa or less, and
160 hours to 240 hours: regulated at 0.1 kPa or more to 20 kPa or less)
Sterilization: The culture tank including the separation membrane element, and the used medium, were sterilized with high-pressure steam in an autoclave at 121° C. for 20 minutes.

The yeast SW-1 strain created in Reference Example 1 was used as the microorganism, a lactic acid fermentation medium having the composition shown in Table 1 was used as the medium, the concentration of L-lactic acid as a product was evaluated by HPLC shown in Reference Example 1, and the concentration of glucose was measured with Glucose Test Wako C (Wako Pure Chemical Industries, Ltd.).

First, the SW-1 strain was shake-cultured overnight in 5 ml of a lactic acid fermentation medium in a test tube (prior preliminary preculture). The resulting culture was inoculated into 100 ml of a fresh lactic acid fermentation medium and shake-cultured for 24 hours at 30° C. in a 500-ml Sakaguchi flask (preliminary preculture). The preliminary preculture was inoculated into 1.5 L of a lactic acid fermentation medium in the membrane separation-type continuous fermentation apparatus shown in FIG. 2, a reaction tank 1 was stirred at 400 rpm with an agitator 5 attached thereto, followed by the aeration regulation, temperature control, and pH adjustment of the reaction tank 1, and the microorganism was cultured for 24 hours (preculture). Immediately after preculture was finished, the microorganism was continuously cultured with a continuously fed lactic acid fermentation medium and with the amount of membrane permeation water regulated such that the amount of the fermentation liquor in the membrane separation-type continuous fermentation apparatus became 1.5 L, whereby L-lactic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of L-lactic acid produced in the membrane permeation fermentation liquor and the residual glucose concentration were measured at an appropriate time. The yield of L-lactic acid to sugar and the rate of production of L-lactic acid calculated from the L-lactic acid and introduced glucose calculated from the glucose concentration are shown in Table 2.

As a result of the fermentation test for 240 hours, stable production of L-lactic acid by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Example 5

Production of L-Lactic Acid by Continuous Fermentation Using Yeast (No. 5)

The same L-lactic acid continuous fermentation test as in Example 4 was conducted by using the porous membrane prepared in Reference Example 3 as a separation membrane. The results are shown in Table 2. As a result, stable production of L-lactic acid was feasible by continuous fermentation. The transmembrane pressure difference fluctuated within 2 kPa in the whole period of continuous fermentation.

Example 6

Production of L-Lactic Acid by Continuous Fermentation Using Yeast (No. 6)

The same L-lactic acid continuous fermentation test as in Example 5 was conducted by using the porous membrane prepared in Reference Example 4 as a separation membrane. The results are shown in Table 2. As a result, stable production of L-lactic acid was feasible by continuous fermentation. The transmembrane pressure difference fluctuated within 2 kPa in the whole period of continuous fermentation.

Comparative Example 1

Production of L-Lactic Acid by Batch Fermentation

As a fermentation form using a microorganism, most typical batch fermentation was conducted to evaluate its L-lactic acid productivity. A batch fermentation test was conducted wherein the lactic acid fermentation-medium shown in Table 1 was used and the reaction tank 1 only of the membrane separation-type continuous fermentation apparatus in FIG. 1 was used. The medium was used after high-pressure steam sterilization (121° C., 15 minutes). The yeast SW-1 strain created in Reference Example 1 was also used as the microorganism in this comparative example, the concentration of L-lactic acid as a product was evaluated by HPLC shown in Reference Example 1, and the concentration of glucose was measured with Glucose Test Wako C (Wako Pure Chemical Industries., Ltd.). The operation conditions in Comparative Example 2 are as follows:

Reaction tank capacity (amount of the lactic acid fermentation medium): 1 (L)
Temperature control: 30 (° C.)
Reaction tank aeration: 0.05 (L/min)
Reaction tank agitation rate: 100 (rpm)
pH adjustment: adjusted to pH 5 with 1 N NaOH First, the SW-1 strain was shake-cultured overnight in 5 ml of a lactic acid fermentation medium in a test tube (preliminary preculture). The preliminary preculture was inoculated into 100 ml of a fresh lactic acid fermentation medium and shake-cultured for 24 hours in a 500-ml Sakaguchi flask (preculture). The preculture was inoculated into 1.5 L of a lactic acid fermentation medium in the membrane separation-type continuous fermentation apparatus, a reaction tank 1 was stirred at 100 rpm with an agitator 5 attached thereto, and the reaction tank 1 was aerated. Temperature adjustment and pH adjustment were carried out, and without operating a fermentation liquor circulating pump 10, batch fermentation culture was conducted. The amount of the microorganisms grown in this culture was 14 in terms of absorbance at 600 nm. The results of batch fermentation are shown in Table 2.

TABLE 2

|  | Comparative Example 1 | Example 1 | Example 2 | Example 3 | Example 4 | Example 5 | Example 6 |
|---|---|---|---|---|---|---|---|
| Fermentation time (hr) | 72 | 300 | 300 | 300 | 300 | 300 | 300 |
| Total introduced glucose (g) | 100 | 2620 | 2720 | 2750 | 2120 | 2070 | 2110 |
| Total produced L-lactic acid (g) | 26 | 1580 | 1525 | 1540 | 1350 | 1305 | 1350 |
| Unused glucose (g) | 0 | 60 | 75 | 90 | 40 | 30 | 35 |
| L-lactic acid yield relative to sugar (g/g) | 0.26 | 0.62 | 0.58 | 0.58 | 0.65 | 0.64 | 0.65 |
| L-lactic acid production rate (g/L/hr) | 0.36 | 2.6 | 2.5 | 2.5 | 3.0 | 2.9 | 3.0 |

The rate of production of L-lactic acid was significantly improved by the method of producing a chemical product according to the present invention using the fermentation apparatus shown in FIGS. 1 and 2.

Comparative Example 2

Production of L-Lactic Acid by Continuous Fermentation Using Yeast

Continuous fermentation was conducted in the same manner as in Example 1 except that the porous membrane having a small pore diameter and a low purified-water permeability coefficient, prepared in Reference Example 5, was used as the separation membrane, and the amount of water penetrated through the membrane was regulated by regulating the flow rate with transmembrane pressure difference (regulated in the range of 0.1 or more to 20 kPa or less in the whole period of continuous fermentation).

As a result, the transmembrane pressure difference exceeded 20 kPa in 96 hours after culture was initiated, to cause clogging the membrane, and thus continuous fermentation was stopped. Accordingly, it was revealed that the porous membrane prepared in Reference Example 5 is not suitable for production of L-lactic acid.

Comparative Example 3

Production of L-Lactic Acid by Continuous Fermentation Using Yeast

Continuous fermentation was conducted in the same manner as in Example 4 except that the porous membrane having a small pore diameter and a low purified-water permeability coefficient, prepared in Reference Example 5, was used as the separation membrane, and the amount of water penetrated through the membrane was regulated by regulating the flow rate with transmembrane pressure difference (regulated in the range of 0.1 or more to 20 kPa or less in the whole period of continuous fermentation).

As a result, the transmembrane pressure difference exceeded 20 kPa in 80 hours after culture was initiated, to cause clogging the membrane, and thus continuous fermentation was stopped. Accordingly, it was revealed that the porous membrane prepared in Reference Example 5 is not suitable for production of L-lactic acid.

Example 7

Production of Ethanol by Continuous Fermentation (No. 1)

Production of ethanol was conducted by using the membrane separation-type continuous fermentation apparatus in FIG. 1 and an ethanol fermentation medium having the composition shown in Table 3. The medium was used after high-pressure steam sterilization (121° C., 15 minutes). As the separation membrane, the porous membrane prepared in Reference Example 2 was used. Unless otherwise noted, the operation conditions in this example are as follows:
Reaction tank capacity: 2 (L)
Membrane separation tank capacity: 0.5 (L)
Used separation membrane: polyvinylidene fluoride filtration membrane
Membrane separation element effective filtration area: 120 cm$^2$
Temperature control: 30 (° C.)
Reaction tank aeration: 0.05 (L/min)
Membrane separation tank aeration: 0.3 (L/min)
Reaction tank agitation rate: 100 (rpm)
pH adjustment: adjusted to pH 5 with 1 N NaOH
Ethanol fermentation medium feed rate: variable control in the range of 50 to 300 ml/hr.
Amount of circulating liquid with a fermentation liquor circulating apparatus: 0.1 (L/min)
Regulation of the amount of membrane permeation water: flow rate regulation by transmembrane pressure difference (From start of continuous fermentation to 100 hours: regulated at 0.1 kPa or more to 5 kPa or less, 100 hours to 200 hours: regulated at 0.1 kPa or more to 2 kPa or less, and 200 hours to 300 hours: regulated at 0.1 kPa or more to 20 kPa or less)

NBRC10505 strain was used as the microorganism, an ethanol fermentation medium having the composition shown in Table 1 was used as the medium, the concentration of ethanol as a product was quantified by gas chromatography for evaluation. In gas chromatography, Shimadzu GC-2010 capillary GC TC-1 (GL Science) 15 meter L×0.53 mm I.D., df 1.5 μm was used, and hydrogen flame ionization detector (FID) was used in detection and calculation. The concentration of glucose was measured with Glucose Test Wako C (Wako Pure Chemical Industries, Ltd.).

TABLE 3

| Ethanol fermentation medium | |
|---|---|
| Glucose | 100 g |
| Yeast Nitrogen base w/o amino acid (Difco) | 6.7 g |
| Standard 19 amino acids excluding leucine | 78 mg |
| Leucine | 380 mg |
| Inositol | 76 mg |
| p-Aminobenzoic acid | 8 mg |
| Adenine | 40 mg |
| Uracil | 76 mg |

Unit (1/Liter)

First, the NBRC10505 strain was shake-cultured overnight in 5 ml of an ethanol fermentation medium in a test tube (prior preliminary preculture). The resulting culture was inoculated into 100 ml of a fresh ethanol fermentation medium and shake-cultured for 24 hours at 30° C. in a 500-ml Sakaguchi flask (preliminary preculture). The preliminary preculture was inoculated into 1.5 L of an ethanol fermentation medium in the membrane separation-type continuous fermentation apparatus shown in FIG. 1, a reaction tank 1 was stirred at 100 rpm with an agitator 5 attached thereto, followed by the aeration regulation, temperature control, and pH adjustment of the reaction tank 1, and without operating a fermentation liquor circulating pump 10, the microorganism was cultured for 24 hours (preculture). Immediately after preculture was finished, the fermentation liquor circulating pump 10 was operated, and the microorganism was continuously cultured under the conditions where in addition to the operation conditions at the time of preculture, a membrane separation tank 2 was aerated, an ethanol fermentation medium was continuously fed, and the amount of membrane permeation water was regulated such that the amount of the fermentation liquor in the membrane separation-type continuous fermentation apparatus became 2 L, whereby ethanol was produced by continuous fermentation. In this continuous fermentation test, the amount of membrane permeation water was regulated and changed under the membrane permeate water control conditions described above, during which the water head difference was measured as transmembrane pressure difference with a water head difference regulating apparatus 3. The concentration of ethanol produced in the membrane permeation fermentation liquor and the residual glucose concentration were measured at an appropriate time. The results are shown in Table 4.

Stable production of ethanol by membrane separation-type continuous fermentation was feasible by the method of producing a chemical product according to the present invention by using the continuous fermentation apparatus in FIG. 1. The transmembrane pressure difference fluctuated within 2 kPa in the whole period of continuous fermentation.

Example 8

Production of Ethanol by Continuous Fermentation (No. 2)

Production of ethanol was conducted by using the continuous fermentation apparatus in FIG. 2 and an ethanol fermentation medium having the composition shown in Table 3. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Reaction tank capacity: 2 (L)
Used separation membrane: polyvinylidene fluoride filtration membrane
Membrane separation element effective filtration area: 120 $cm^2$
Temperature control: 30 (° C.)
Fermentation reaction tank aeration: 0.05 (L/min)
Lactic acid fermentation medium feed rate: variable control in the range of 50 to 300 ml/hr.
Fermentation reaction tank agitation rate: 800 (rpm)
pH adjustment: adjusted to pH 5 with 1 N NaOH
Regulation of the amount of membrane permeation water: flow rate regulation by transmembrane pressure difference
(From start of continuous fermentation to 80 hours: regulated at 0.1 kPa or more to 5 kPa or less,
80 hours to 160 hours: regulated at 0.1 kPa or more to 2 kPa or less, and
160 hours to 240 hours: regulated at 0.1 kPa or more to 20 kPa or less)
Sterilization: The culture tank including the separation membrane element, and the used medium, were sterilized with high-pressure steam in an autoclave at 121° C. for 20 minutes.

Yeast NBRC10505 strain was used as the microorganism, an ethanol fermentation medium having the composition shown in Table 2 was used as the medium, the concentration of ethanol as a product was evaluated by gas chromatography shown in Example 7, and the concentration of glucose was measured with Glucose Test Wako C (Wako Pure Chemical Industries; Ltd.).

First, the NBRC10505 strain was shake-cultured overnight in 5 ml of an ethanol fermentation medium in a test tube (prior preliminary preculture). The resulting culture was inoculated into 100 ml of a fresh ethanol fermentation medium and shake-cultured for 24 hours at 30° C. in a 500-ml Sakaguchi flask (preliminary preculture). The preliminary preculture was inoculated into 1.5 L of a ethanol fermentation medium in the membrane separation-type continuous fermentation apparatus shown in FIG. 2, a reaction tank 1 was stirred at 400 rpm with an agitator 5 attached thereto, followed by the aeration regulation, temperature control, and pH adjustment of the reaction tank 1, and the microorganism was cultured for 24 hours (preculture). Immediately after preculture was finished, the microorganism was continuously cultured in a continuously fed ethanol fermentation medium with the amount of membrane permeation water regulated such that the amount of the fermentation liquor in the membrane separation-type continuous fermentation apparatus became 1.5 L, whereby ethanol was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of ethanol produced in the membrane permeation fermentation liquor and the residual glucose concentration were measured at an appropriate time. The yield of ethanol relative to sugar and the rate of production of ethanol calculated from the ethanol and introduced glucose calculated from the glucose concentration are shown in Table 4.

Stable production of ethanol by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 4

Production of Ethanol by Batch Fermentation

As a fermentation form using a microorganism, most typical batch fermentation was conducted to evaluate its ethanol productivity. A batch fermentation test was conducted wherein the ethanol fermentation medium shown in Table 3 was used and the reaction tank 1 only of the membrane separation-type continuous fermentation apparatus in FIG. 1 was used. The medium was used after high-pressure steam sterilization (121° C., 15 minutes). NBRC10505 strain was also used as the microorganism in this comparative example, the concentration of ethanol as a product was evaluated by gas chromatography shown in Example 6, and the concentration of glucose was measured with Glucose Test Wako C (Wako Pure Chemical Industries, Ltd.). The operation conditions in this comparative example are as follows:
Reaction tank capacity (amount of the ethanol fermentation medium): 1 (L)
Temperature control: 30 (° C.)
Reaction tank aeration: 0.05 (L/min)
Reaction tank agitation rate: 100 (rpm)
pH adjustment: adjusted to pH 5 with 1 N NaOH First, the NBRC10505 strain was shake-cultured overnight in 5 ml of an ethanol fermentation medium in a test tube (preliminary preculture). The preliminary preculture was inoculated into 100 ml of a fresh ethanol fermentation medium and shake-cultured for 24 hours in a 500-ml Sakaguchi flask (preculture). The preculture was inoculated into 1.5 L of an ethanol fermentation medium in the membrane separation-type continuous fermentation apparatus, a reaction tank 1 was stirred at 100 rpm with an agitator 5 attached thereto, and the reaction tank 1 was aerated. Temperature adjustment and pH adjustment were carried out, and without operating a fermentation liquor circulating pump 10, batch fermentation culture was conducted. The amount of the microorganisms grown in this culture was 18 in terms of absorbance at 600 nm. The results of batch fermentation are shown in Table 4.

TABLE 4

|  | Comparative Example 4 | Example 7 | Example 8 |
|---|---|---|---|
| Fermentation time (hr) | 28 | 300 | 300 |
| Total introduced glucose (g) | 100 | 6320 | 4750 |
| Total produced ethanol (g) | 47 | 2900 | 2120 |
| Unused glucose (g) | 0 | 50 | 35 |
| Ethanol yield relative to sugar (g/g) | 0.47 | 0.46 | 0.45 |
| Ethanol production rate (g/L/hr) | 1.7 | 4.8 | 4.7 |

The rate of production of ethanol was significantly improved by the method of producing a chemical product according to the present invention using the fermentation apparatus shown in FIGS. 1 and 2.

Example 9

Production of Pyruvic acid by Continuous Fermentation (No. 1)

Production of pyruvic acid was conducted by using the membrane separation-type continuous fermentation apparatus in FIG. 1 and a pyruvic acid fermentation medium having the composition shown in Table 0.5. The medium was used after high-pressure steam sterilization (121° C., 15 minutes). As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 cm$^2$
Temperature control: 30 (° C.)
Fermentation reaction tank aeration: 1.5 (L/min)
Fermentation reaction tank agitation rate: 800 (rpm)
pH adjustment: adjusted to pH 5.5 with 4 N NaOH
Sterilization: The culture tank including the separation membrane element, and every medium used, were sterilized at high pressure in an autoclave at 121° C. for 20 minutes.
Regulation of the amount of membrane permeation water: flow rate regulation by transmembrane pressure difference (From start of continuous fermentation to 100 hours: regulated at 0.1 kPa or more to 5 kPa or less,
100 hours to 180 hours: regulated at 0.1 kPa or more to 2 kPa or less, and
180 hours to 264 hours: regulated at 0.1 kPa or more to 20 kPa or less)
*Torulopsis glabrata* P120-5a strain (FERM P-16745) was used as the microorganism, a pyruvic acid fermentation medium having the composition shown in Table 5 was used as the medium, and the concentration of pyruvic acid as a product was evaluated by HPLC under the following conditions:
Column: Shim-Pack SPR-H (manufactured by Shimadzu Corporation)
Mobile phase: 5 mM p-toluenesulfonic acid (flow rate 0.8 mL/min)
Reaction solution: 5 mM p-toluenesulfonic acid, 20 mM Bis-Tris,
0.1 mM EDTA•2 Na (flow rate 0.8 mL/min)
Detection method: electric conductivity
Temperature: 45° C.

The concentration of glucose was measured with Glucose Test Wako C (Wako Pure Chemical Industries, Ltd.).

TABLE 5

| Pyruvic acid fermentation medium | |
|---|---|
| Glucose | 100 g/L |
| Ammonium sulfate | 5 g/L |
| Potassium dihydrogen phosphate | 1 g/L |
| Magnesium sulfate 7H$_2$O | 0.5 g/L |
| Soybean hydrolysates | 2 g/L |
| Nicotinic acid | 8 mg/L |
| Pyridoxine hydrochloride | 1 mg/L |
| Biotin | 0.05 mg/L |
| Thiamine hydrochloride | 0.05 mg/L |
|  | pH 5.5 |

First, the P120-5a strain was shake-cultured overnight in 5 ml of a pyruvic acid fermentation medium in a test tube (prior preliminary preculture). The resulting culture was inoculated into 100 ml of a fresh pyruvic acid fermentation medium and shake-cultured for 24 hours at 30° C. in a 500-ml Sakaguchi flask (preliminary preculture). The preliminary preculture was inoculated into 1.5 L of a pyruvic acid fermentation medium in the membrane separation-type continuous fermentation apparatus shown in FIG. 1, a fermentation reaction tank 1 was stirred at 800 rpm with an agitator 5 attached thereto, followed by the aeration regulation, temperature control, and pH adjustment of the fermentation reaction tank 1, and the microorganism was cultured for 24 hours (preculture). Immediately after preculture was finished, the fermentation liquor circulating pump 10 was operated, and the microorganism was continuously cultured under the conditions where in addition to the operation conditions at the time of preculture, a membrane separation tank 2 was aerated, a pyruvic acid fermentation medium was continuously fed, and the amount of membrane permeation water was regulated such that the amount of the fermentation liquor in the membrane separation-type continuous fermentation apparatus became 2 L, whereby pyruvic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of pyruvic acid produced in the membrane permeation fermentation liquor and the residual glucose concentration were measured at an appropriate time. The results in the continuous fermentation test for 300 hours are shown in Table 6.

Stable production of pyruvic acid by continuous fermentation was feasible by the method of producing a chemical product according to the present invention by using the membrane separation-type continuous fermentation apparatus in FIG. 1. The transmembrane pressure difference fluctuated within 2 kPa in the whole period of continuous fermentation.

Example 10

Production of Pyruvic Acid by Continuous Fermentation (No. 2)

Production of pyruvic acid was conducted by using the continuous fermentation apparatus in FIG. 2 and a pyruvic acid fermentation medium having the composition shown in Table 5. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Reaction tank capacity: 2 (L)
Used separation membrane: polyvinylidene fluoride filtration membrane
Membrane separation element effective filtration area: 120 $cm^2$
Temperature control: 30 (° C.)
Fermentation reaction tank aeration: 1 (L/min)
Lactic acid fermentation medium feed rate: variable control in the range of 50 to 300 ml/hr.
Fermentation reaction tank agitation rate: 800 (rpm)
pH adjustment: adjusted to pH 5.5 with 4 N NaOH
Regulation of the amount of membrane permeation-water: flow rate regulation by transmembrane pressure difference (From start of continuous fermentation to 100 hours: regulated at 0.1 kPa or more to 5 kPa or less,
100 hours to 180 hours: regulated at 0.1 kPa or more to 2 kPa or less, and
180 hours to 264 hours: regulated at 0.1 kPa or more to 20 kPa or less)
Sterilization: The culture tank including the separation membrane element, and the used medium, were sterilized with high-pressure steam in an autoclave at 121° C. for 20 minutes.

*Torulopsis* glabrata P120-5a strain (FERM P-16745) was used as the microorganism, a pyruvic acid fermentation medium having the composition shown in Table 5 was used as the medium, and the concentration of pyruvic acid as a product was evaluated by HPLC under the following conditions.

First, the P120-5a strain was shake-cultured overnight in 5 ml of a pyruvic acid fermentation medium in a test tube (prior preliminary preculture). The resulting culture was inoculated into 100 ml of a fresh pyruvic acid fermentation medium and shake-cultured for 24 hours at 30° C. in a 500-ml Sakaguchi flask (preliminary preculture). The preliminary preculture was inoculated into 1.5 L of a lactic acid fermentation medium in the membrane separation-type continuous fermentation apparatus shown in FIG. 2, a reaction tank 1 was stirred at 800 rpm with an agitator 5 attached thereto, followed by the aeration regulation, temperature control, and pH adjustment of the reaction tank 1, and the microorganism was cultured for 24 hours (preculture). Immediately after preculture was finished, a pyruvic acid fermentation medium was continuously fed, and the microorganism was continuously cultured with the amount of membrane permeation water regulated such that the amount of the fermentation liquor in the membrane separation-type continuous fermentation apparatus became 1.5 L, whereby pyruvic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of pyruvic acid produced in the Membrane permeation fermentation liquor and the residual glucose concentration were measured at an appropriate time. The yield of lactic acid relative to sugar and the rate of production of lactic acid calculated from the pyruvic acid and introduced glucose calculated from the glucose concentration are shown in Table 6.

As a result of the fermentation test for 300 hours, stable production of pyruvic acid by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Example 11

Production of Pyruvic Acid by Continuous Fermentation (No. 3)

The membrane separation-type continuous fermentation apparatus in FIG. 1 was used, NBRC0005 strain was used as the microorganism, and all other conditions were the same as in Example 9. The results of continuous fermentation are shown in Table 6. As a result of the fermentation test for 300 hours, stable production of pyruvic acid by continuous fermentation was feasible by the method of producing a chemical product according to the present invention by using the membrane separation-type continuous fermentation apparatus in FIG. 1. The transmembrane pressure difference fluctuated within 2 kPa in the whole period of continuous fermentation.

Example 12

Production of Pyruvic Acid by Continuous Fermentation (No. 4)

The continuous fermentation apparatus in FIG. 2 was used, NBRC0005 strain was used as the microorganism, and all other conditions were the same as in Example 10. The results of continuous fermentation are shown in Table 6. As a result of the fermentation test for 300 hours, stable production of pyruvic acid by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 5

Production of Pyruvic Acid by Batch Fermentation (No. 1)

As a fermentation form using a microorganism, most typical batch fermentation was conducted in a 2-L jar fermenter to evaluate its pyruvic acid productivity. As the medium, the medium shown in Table 5 was used after high-pressure steam sterilization (121° C., 15 minutes). P120-5a strain was used as the microorganism in this comparative example, the concentration of pyruvic acid as a product was evaluated by HPLC shown in Example 9, and the concentration of glucose was measured with Glucose Test Wako C (Wako Pure Chemical Industries, Ltd.). The operation conditions in this comparative example are as follows:
Fermentation reaction tank capacity (amount of the pyruvic acid fermentation medium): 1 (L)
Temperature control: 30 (° C.)
Fermentation reaction tank aeration: 1 (L/min)
Fermentation reaction tank agitation rate: 600 (rpm)
pH adjustment: adjusted to pH 5.5 with 4 N NaOH First, the P120-5a strain was shake-cultured overnight in 5 ml of a pyruvic acid fermentation medium in a test tube (preliminary preculture). The preliminary preculture was inoculated into 50 ml of a fresh pyruvic acid fermentation are medium and shake-cultured for 24 hours in a 500-ml Sakaguchi flask (preculture). The preculture was inoculated into 1 L of a pyruvic acid fermentation medium in a jar fermenter and subjected to batch fermentation. The results of batch fermentation are shown in Table 6.

Comparative Example 6

Production of Pyruvic Acid by Batch Fermentation (No. 2)

As a fermentation form using a microorganism, most typical batch fermentation was conducted in a 2-L jar fermenter to evaluate its pyruvic acid productivity. In this comparative example, NBRC0005 strain was used as the microorganism, and all other conditions were the same as in Comparative Example 3. The results of batch fermentation are shown in Table 6.

umn temperature was 50° C., and the column was equilibrated with 0.01 N $H_2SO_4$, and then a sample was injected into the column and analyzed by elution with 0.01 $H_2SO_4$. Glucose was measured by a glucose sensor (BF-4, Oji Scientific Instruments).

The medium was used after high-pressure steam sterilization (121° C., 15 minutes). As the separation membrane, the porous membrane prepared in Reference Example 2 was used. Unless otherwise noted, the operation conditions in this example are as follows:
Reaction tank capacity: 2 (L)
Membrane separation tank capacity: 0.5 (L)
Used separation membrane: polyvinylidene fluoride filtration membrane
Membrane separation element effective filtration area: 60 $cm^2$
Temperature control: 39 (° C.)
Reaction tank $CO_2$ aeration: 10 (mL/min)
Membrane separation tank $CO_2$ aeration: 100 (mL/min)
Reaction tank agitation rate: 100 (rpm)
pH adjustment: adjusted to pH 6.4 with 2 M $Na_2CO_3$
Lactic acid fermentation medium feed rate: variable control in the range of 50 to 300 ml/hr.
Amount of circulating liquid with a fermentation liquor circulating apparatus: 0.1 (L/min)
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and

TABLE 6

|  | Comparative Example 3 | Example 9 | Example 10 | Comparative Example 4 | Example 11 | Example 12 |
|---|---|---|---|---|---|---|
| Fermentation time (hr) | 72 | 264 | 264 | 45 | 264 | 264 |
| Total introduced glucose (g) | 100 | 3410 | 2806 | 100 | 3440 | 2660 |
| Total produced sodium pyruvate (g) | 70 | 1790 | 1237 | 58 | 1580 | 1110 |
| Unused glucose (g) | 0 | 320 | 419 | 0 |  | 190 |
| Sodium pyruvate yield relative to sugar (g/g) | 0.70 | 0.58 | 0.52 | 0.58 | 0.49 | 0.45 |
| Sodium pyruvate production rate (g/L/hr) | 1.0 | 3.4 | 3.1 | 1.28 | 3.0 | 2.8 |

The rate of production of pyruvic acid was significantly improved by the method of producing a chemical product according to the present invention using the fermentation apparatus shown in FIGS. 1 and 2.

Example 13

Production of Succinic Acid by Continuous Fermentation (No. 1)

Production of succinic acid was conducted by using the membrane separation-type continuous fermentation apparatus in FIG. 1.

Unless otherwise noted, succinic acid and glucose in production of succinic acid were measured by the following method. Succinic acid in a centrifuged supernatant of a culture was analyzed by HPLC (Shimadzu LC10A, RI monitor: RID-10A, column: Aminex HPX-87H). The col- 200 hours to 264 hours: regulated at 0.1 kPa or more to 20 kPa or less)

In this example, continuous production of succinic acid by *Anaerobiospirillum succiniciproducens* ATCC53488 as a microorganism having an ability to produce succinic acid was conducted. 100 mL of a seed culture medium consisting of 20 g/L glucose, 10 g/L polypeptone, 5 g/L yeast extract, 3 g/L $K_2HPO_4$, 1 g/L NaCl, 1 g/L $(NH_4)_2SO_4$, 0.2 g/L $MgCl_2$, and 0.2 g/L $CaCl_2.2H_2O$ was introduced into a 125-mL Erlenmeyer flask and sterilized by heating. In an anaerobic glove box, 1 mL of 30 mM $Na_2CO_3$ and 0.15 mL of 180 mM $H_2SO_4$ were added, and 0.5 mL of a reduced solution consisting of 0.25 g/L cysteine.HCl and 0.25 g/L $Na_2S$ was further added, then ATCC53488 strain was inoculated into the medium and stationary-cultured at 39° C. overnight (preliminary preculture). 5 mL of a reduced solution consisting of 0.25 g/L cysteine.HCl and 0.25 g/L $Na_2S.9H_2O$ was added to 1.5 L of a succinic acid fermentation medium (Table 7) in the membrane separation-type continuous fermentation apparatus shown in FIG. 1, and 50 mL of the preliminary preculture was inoculated into it, a fermentation reaction tank 1 was stirred at 200 rpm with an agitator 5 attached thereto, followed by the $CO_2$ aeration regulation, temperature control, and pH adjustment of the fermentation reaction tank 1, and the microorganism was cultured for 24 hours (preculture).

TABLE 7

Succinic acid fermentation medium

| | Medium for Actinobacillus succinogenes |
|---|---|
| Glucose | 100.0 g/L |
| NaCl | 1.0 g/L |
| $CaCl_2 \cdot 2H_2O$ | 0.2 g/L |
| $NaH_2PO_4 \cdot H_2O$ | 1.2 g/L |
| $Na_2HPO_4$ | 0.3 g/L |
| $K_2HPO_2$ | — g/L |
| $MgCl_2 \cdot 6H_2O$ | 0.2 g/L |
| Vitamin $B_{12}$ | 10 μg/L |
| Biotin | 200 μg/L |
| Folic acid | 200 μg/L |
| Thiamine•HCl | 500 μg/L |
| Riboflavin | 500 μg/L |
| Niacin | 500 μg/L |
| Pantothenic acid | 500 μg/L |
| p-Aminobenzoic acid | 500 μg/L |
| Vitamin $B_6$ | 1 μg/L |
| Yeast extract | 5.0 g/L |
| Corn steep liquor | 10.0 g/L |
| Polypeptone | — g/L |
| $NH_4Cl$ | — g/L |
| $FeSO_4 \cdot 7H_2O$ | — g/L |

Immediately after preculture was finished, a succinic acid fermentation medium was continuously fed, and the microorganism was continuously cultured while the amount of membrane permeation water was regulated such that the amount of the fermentation liquor in the membrane separation-type continuous fermentation apparatus became 2 L, whereby succinic acid was produced by continuous fermentation. The amount of membrane permeation water in the continuous fermentation test was regulated by appropriately changing the water head difference such that the water head difference of the fermentation reaction tank was within 2 m, that is, the transmembrane pressure difference was 0.1 or more to 20 kPa or less. The concentration of succinic acid produced in the membrane permeation fermentation liquor and the residual glucose concentration were measured at an appropriate time. The rate of production of succinic acid and the yield of succinic acid, calculated from the succinic acid and the glucose concentration are shown in Table 8. The transmembrane pressure difference fluctuated within 2 kPa in the whole period of continuous fermentation.

Example 14

Production of Succinic Acid by Continuous Fermentation (No. 2)

Production of succinic acid was conducted by using the continuous fermentation apparatus in FIG. 2. The medium was used after high-pressure steam sterilization (121° C., 15 minutes). The concentrations of succinic acid and glucose were measured in the same manner as in Example 13. As the separation membrane, the porous membrane prepared in Reference Example 2 was used. Unless otherwise noted, the operation conditions in this example are as follows:
Reaction tank capacity: 2 (L)
Used separation membrane: polyvinylidene fluoride filtration membrane
Membrane separation element effective filtration area: 120 $cm^2$
Temperature control: 39 (° C.)
Fermentation reaction tank $CO_2$ aeration: 10 (mL/min)
Lactic acid fermentation medium feed rate: variable control in the range of 50 to 300 ml/hr.
Fermentation reaction tank agitation rate: 600 (rpm)
pH adjustment: adjusted to pH 6.4 with 2 M $Na_2CO_3$
Regulation of the amount of membrane permeation water: flow rate regulation by transmembrane pressure difference (From start of continuous fermentation to 80 hours: regulated at 0.1 kPa or more to 5 kPa or less,
80 hours to 160 hours: regulated at 0.1 kPa or more to 2 kPa or less, and
160 hours to 280 hours: regulated at 0.1 kPa or more to 20 kPa or less)
Sterilization: The culture tank including the separation membrane element, and the used medium, were sterilized with high-pressure steam in an autoclave at 121° C. for 20 minutes.

In this example, continuous production of succinic acid by *Anaerobiospirilum succiniciproducens* ATCC53488 strain as a microorganism having an ability to produce succinic acid was conducted. 100 mL of a seed culture medium consisting of 20 g/L glucose, 10 g/L polypeptone, 5 g/L yeast extract, 3 g/L $K_2HPO_4$, 1 g/L NaCl, 1 g/L $(NH_4)_2SO_4$, 0.2 g/L $MgCl_2$, and 0.2 g/L $CaCl_2 \cdot 2H_2O$ was introduced into a 125-mL Erlenmeyer flask and sterilized by heating. In an anaerobic glove box, 1 mL of 30 mM $Na_2CO_3$ and 0.15 mL of 180 mM $H_2SO_4$ were added, and 0.5 mL of a reduced solution consisting of 0.25 g/L cysteine.HCl and 0.25 g/L $Na_2S$ was further added, then ATCC53488 strain was inoculated into the medium and stationary-cultured overnight at 39° C. (preliminary preculture). 5 mL of a reduced solution consisting of 0.25 g/L cysteine.HCl and 0.25 g/L $Na_2S \cdot 9H_2O$ was added to 1.5 L of a succinic acid fermentation medium (Table 7) in the continuous fermentation apparatus shown in FIG. 2, and 50 mL of the preliminary preculture was inoculated into it, a fermentation reaction tank 1 was stirred at 600 rpm with an agitator 5 attached thereto, followed by the $CO_2$ aeration regulation, temperature control, and pH adjustment of the fermentation reaction tank 1, and the microorganism was cultured for 24 hours (preculture).

Immediately after preculture was finished, a succinic acid fermentation medium was continuously fed, and the microorganism was continuously cultured while the amount of membrane permeation water was regulated such that the amount of the fermentation liquor in the membrane separation-type continuous fermentation apparatus became 1.5 L, whereby succinic acid was produced by continuous fermentation. The amount of membrane permeation water in the continuous fermentation test was conducted by appropriately changing the water head difference with a water head difference regulating apparatus 3 such that the water head of the fermentation reaction tank was within 2 m at maximum, that is, the transmembrane pressure difference was 0.1 to 20 kPa. The concentration of succinic acid produced in the membrane permeation fermentation liquor and the residual glucose concentration were measured at an appropriate time. The rate of production of succinic acid aid the yield of succinic acid, calculated from the succinic acid and glucose concentration are shown in Table 8. The transmembrane pressure difference fluctuated within 2 kPa in the whole period of continuous fermentation.

Comparative Example 7

Production of Succinic Acid by Batch Fermentation

Production of succinic acid by batch fermentation of *Anaerobiospirillum succiniciproducens* was carried out in the following manner.

100 mL of a seed culture medium consisting of 20 g/L glucose, 10 g/L polypeptone, 5 g/L yeast extract, 3 g/L $K_2HPO_4$, 1 g/L NaCl, 1 g/L $(NH_4)_2SO_4$, 0.2 g/L $MgCl_2$, and 0.2 g/L $CaCl_2 \cdot 2H_2O$ was introduced into a 125-mL Erlenmeyer flask and sterilized by heating. In an anaerobic glove box, 1 mL of 30 mM $Na_2CO_3$ and 0.15 mL of 180 mM $H_2SO_4$ were added, and 0.5 mL of a reduced solution consisting of 0.25 g/L cysteine-HCl and 0.25 g/L $Na_2S$ was further added, then *Anaerobiospirillum succiniciproducens* ATCC53488 strain was inoculated into the medium and stationary-cultured overnight at 39° C. 1 L of a fermentation medium shown in Table 7 was added to a mini-jar fermenter (2 L, BMJ type, manufactured by ABLE) and sterilized by heating (120° C., 20 min)

A $CO_2$ gas was introduced at a rate of 10 mL/min. with a sparger, and 10 mL of 3 M $Na_2CO_3$ solution was added, and the pH was adjusted to 6.8 with a sulfuric acid solution. 5 mL of a reduced solution consisting of 0.25 g/L cysteine.HCl and 0.25 g/L $Na_2S \cdot 9H_2O$ was added, and the 50 mL of the seed culture was inoculated into the medium and cultured at stirring rate of 200 rpm at a temperature of 39° C. while the pH was adjusted to 6.4 with 2 M $Na_2CO_3$ solution. The results are shown in Table 8.

TABLE 8

|  |  | Comparative Example 7 | Example 13 | Example 14 |
|---|---|---|---|---|
| Fermentation time | (hr) | 39 | 264 | 280 |
| Introduced glucose | (g) | 49 | 1090 | 1689 |
| Formed succinic acid | (g) | 38 | 871 | 1394 |
| Unused glucose | (g) | 1 | 15 | 29 |
| Yield | (g/g) | 0.775 | 0.81 | 0.84 |
| Production rate | (g/L/hr) | 0.97 | 2.2 | 3.3 |

The rate of production of succinic acid was significantly improved by the method of producing a chemical product according to the present invention using the fermentation apparatus shown in FIGS. 1 and 2.

Example 15

Production of Succinic Acid by Continuous Fermentation (No. 3)

Production of succinic acid was conducted by using the membrane separation-type continuous fermentation apparatus in FIG. 1. The concentrations of succinic acid and glucose were measured in the same manner as in Example 13. The medium was used after high-pressure steam sterilization (121° C., 15 minutes). As the separation membrane, the porous membrane prepared in Reference Example 2 was used. The operation conditions in this example are the same as in Example 13 except for the following regulation of the amount of membrane permeation water.

Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and
200 hours to 254 hours: regulated at 0.1 kPa or more to 20 kPa or less)

In this example, continuous production of succinic acid by *Actinobacillus succinogenes* ATCC55618 strain as a microorganism having an ability to produce succinic acid was conducted. 75 mL of a succinic acid fermentation medium for *Actinobacillus* shown in Table 9 and 4.0 g of $MgCO_3$ were added to a 100-mL serum test tube, followed by replacing the gas in the tube by $CO_2$ and sterilization under heating. 7.5 mL of a bacterial suspension of the ATCC55618 strain was inoculated and cultured at 37° C. for 24 hours to prepare a seed culture (preliminary preculture).

TABLE 9

| Succinic acid fermentation medium | |
|---|---|
|  | Medium for *Anaerobiospirillum succiniciproducens* |
| Glucose | 50.0 g/L |
| NaCl | — g/L |
| $CaCl_2 \cdot 2H_2O$ | 0.2 g/L |
| $NaH_2PO_4 \cdot H_2O$ | — g/L |
| $Na_2HPO_4$ | — g/L |
| $K_2HPO_2$ | 1.0 g/L |
| $MgCl_2 \cdot 6H_2O$ | 0.2 g/L |
| Vitamin $B_{12}$ | — µg/L |
| Biotin | — µg/L |
| Folic acid | — µg/L |
| Thiamine•HCl | — µg/L |
| Riboflavin | — µg/L |
| Niacin | — µg/L |
| Pantothenic acid | — µg/L |
| p-Aminobenzoic acid | — µg/L |
| Vitamin $B_6$ | — µg/L |
| Yeast extract | 5.0 g/L |
| Corn steep liquor | — g/L |
| Polypeptone | 10.0 g/L |
| $NH_4Cl$ | 0.4 g/L |
| $FeSO_4 \cdot 7H_2O$ | 0.001 g/L |

The membrane separation-type continuous fermentation apparatus shown in FIG. 1 was charged with 1.5 L of a succinic acid fermentation medium (Table 9), and 75 mL or the preliminary preculture was inoculated into it. The microorganism was continuously cultured in the same manner as in Example 13 except that the $CO_2$ aeration in the fermentation reaction bath 1 was 75 mL/min., the $CO_2$ aeration in the separation membrane tank was 150 mL/min., the temperature was 39° C., and the pH was adjusted to 6.8 with 5.5 M $NaCO_3$. The concentration of succinic acid produced in the membrane permeation fermentation liquor and the residual glucose concentration were measured at an appropriate time. The rate of production of succinic acid and the yield of succinic acid, calculated from the succinic acid and the glucose concentration are shown in Table 10. The transmembrane pressure difference fluctuated within 2 kPa in the whole period of continuous fermentation.

Example 16

Production of Succinic Acid by Continuous Fermentation (No. 4)

Production of succinic acid was conducted by using the continuous fermentation apparatus in FIG. 2. The medium was used after high-pressure steam sterilization (121° C., 15 minutes). The concentrations of succinic acid and glucose were measured in the same manner as in Example 13. As the separation membrane, the porous membrane prepared in Reference Example 2 was used. The operation conditions in this example are the same as in Example 14 except for the following regulation of the amount of membrane permeation water.

Regulation of the amount of membrane permeation water: flow rate regulation by transmembrane pressure difference (From start of continuous fermentation to 100 hours: regulated at 0.1 kPa or more to 5 kPa or less, 100 hours to 200 hours: regulated at 0.1 kPa or more to 2 kPa or less, and 200 hours to 280 hours: regulated at 0.1 kPa or more to 20 kPa or less)

In this example, continuous production of succinic acid by *Actinobacillus succinogenes* ATCC55618 strain as a microorganism having an ability to produce succinic acid was conducted. Continuous culture was conducted in the same manner as in Example 14 except that in continuous production of succinic acid by *Actinobacillus succinogenes*, the $CO_2$ aeration in the fermentation reaction bath was 75 mL/min., and the pH was adjusted to 6.8 with 5.5 M $NaCO_3$.

First, 75 mL of a succinic acid fermentation medium for *Actinobacillus* shown in Table 9 and 4.0 g of $MgCO_3$ were added to a 100-mL serum test tube, followed by replacing the gas in the tube by $CO_2$ and sterilization under heating. 7.5 mL of a bacterial suspension of the ATCC55618 strain previously stored in a frozen state was inoculated into the medium and cultured at 37° C. for 24 hours to prepare a seed culture (preliminary preculture). The continuous fermentation apparatus shown in FIG. 2 was charged with 1.5 L of a succinic acid fermentation medium (Table 7), and 75 mL of the preliminary preculture was inoculated into the medium and cultured for 24 hours with pH kept at 6.8 (preculture). After preculture was finished, the succinic acid fermentation medium in Table 9 was continuously fed, and the amount of membrane permeation water was regulated such that the amount of the fermentation liquor in the membrane separation-type continuous fermentation apparatus in FIG. 2 became 1.5 L, whereby pyruvic acid was produced by continuous fermentation. The concentration of pyruvic acid produced in the membrane permeation fermentation liquor and the residual glucose concentration were measured at an appropriate time. The rate of production of succinic acid and the yield of succinic acid, calculated from the succinic acid and the glucose concentration are shown in Table 10. The transmembrane pressure difference fluctuated within 2 kPa in the whole period of continuous fermentation.

Comparative Example 8

Production of Succinic Acid by Continuous Fermentation (No. 2)

Production of succinic acid by *Actinobacillus succinogenes* was conducted was carried out in the following manner.

50 mL of a succinic acid fermentation medium for *Actinobacillus* shown in Table 9 and 4.0 g of $MgCO_3$ were added to a 100-mL serum test tube, followed by replacing the gas in the tube by $CO_2$ and sterilization under heating. 5 mL of a bacterial suspension of previously cryopreserved *Actinobacillus succinofenes* ATCC55618 was inoculated into the medium and cultured at 37° C. for 24 hours to prepare a seed culture. 1 L of the fermentation medium shown in Table 9 was adjusted to pH 6.8 and added to a mini-jar fermenter (2 L, BMJ type, manufactured by ABLE) and sterilized by heating (120° C., 20 min). A $CO_2$ gas was introduced at a rate of 50 mL/min. with a sparger, and the temperature was regulated at 39° C. 50 mL of the above seed culture was inoculated into the medium and cultured under stirring at 600 rpm with an agitating blade attached thereto while the pH was adjusted to 6.8 with 5.5 M $NaCO_3$. The results are shown in Table 10.

TABLE 10

|  |  | Comparative Example 8 | Example 15 | Example 16 |
|---|---|---|---|---|
| Fermentation time | (hr) | 49 | 254 | 280 |
| Introduced glucose | (g) | 100 | 1637 | 2182 |
| Formed succinic acid | (g) | 72 | 1193 | 1520 |
| Unused glucose | (g) | 4 | 25 | 11 |
| Yield | (g/g) | 0.75 | 0.74 | 0.70 |
| Production rate | (g/L/hr) | 1.12 | 3.13 | 3.62 |

The rate of production of succinic acid was significantly improved by the method of producing a chemical product according to the present invention using the fermentation apparatuses shown in FIGS. 1 and 2.

Example 17

Continuous Production of Succinic Acid by Continuous Fermentation (No. 5)

Production of succinic acid was conducted by using the membrane separation-type continuous fermentation apparatus in FIG. 1. The concentrations of succinic acid and glucose were measured in the same manner as in Example 13. The medium was used after high-pressure steam sterilization (121° C., 15 minutes). As the separation membrane, the porous membrane prepared in Reference Example 2 was used. The operation conditions in this example are the same as in Example 13 except fort the following regulation of the amount of membrane permeation water.

Regulation of the amount of membrane permeation water: flow rate regulation by transmembrane pressure difference (From start of continuous fermentation to 80 hours: regulated at 0.1 kPa or more to 5 kPa or less, 80 hours to 140 hours: regulated at 0.1 kPa or more to 2 kPa or less, and 140 hours to 200 hours: regulated at 0.1 kPa or more to 20 kPa or less)

In this example, continuous production of succinic acid by *Escherichia coli* B ATCC11303 strain as a microorganism having an ability to produce succinic acid was conducted. 150 mL of a seed culture medium consisting of 12 g/L glucose, 10 g/L polypeptone, 5 g/L yeast extract, 1 g/L $K_2HPO_4$, 1 g/L NaCl, and 0.2 g/L $MgCl_2$ was introduced into a 200-mL Erlenmeyer flask and adjusted to pH 6.8. After 7.5 g of $MgCO_3$ was added, the medium was sterilized by heating and cooled to room temperature, and in an anaerobic glove box, ATCC11303 strain was inoculated into the medium and stationary-cultured overnight at 37° C. (preliminary preculture). The continuous fermentation apparatus shown in FIG. 1 was charged with 1.5 L of a succinic acid fermentation medium consisting of 12 g/L glucose, 10 g/L polypeptone, 5 g/L yeast extract, 1 g/L $K_2HPO_4$, 1 g/L NaCl, and 0.2 g/L $MgCl_2$, and 150 mL of the preliminary preculture was inoculated into the medium. Continuous fermentation of succinic acid was conducted under the same conditions as in Example 13 except that the fermentation temperature was 37° C.

After preculture for 24 hours, the microorganism was continuously cultured while the succinic acid fermentation medium shown in Table 11 was continuously fed and the amount of membrane permeation water was regulated such that the amount of the fermentation liquor in the continuous fermentation apparatus became 2 L.

TABLE 11

| Succinic acid fermentation medium | |
|---|---|
| Glucose | 50 g/L |
| Polypeptone | 10 g/L |
| Yeast extract | 5 g/L |
| Potassium dihydrogen phosphate | 1 g/L |
| Sodium chloride | 1 g/L |
| Magnesium chloride | 0.2 g/L |

The concentration of succinic acid produced in the membrane permeation fermentation liquor and the residual glucose concentration were measured at an appropriate time. The rate of production of succinic acid and the yield of succinic acid, calculated from the succinic acid and glucose concentration are shown in Table 12. The transmembrane pressure difference fluctuated within 2 kPa in the whole period of continuous fermentation.

Example 18

Continuous Production of Succinic Acid by Continuous Fermentation (No. 6)

Production of succinic acid was conducted by using the continuous fermentation apparatus in FIG. 2. The medium was used after high-pressure steam sterilization (121° C., 15 minutes). The concentrations of succinic acid and glucose were measured in the same manner as in Example 13. As the separation membrane, the porous membrane prepared in Reference Example 2 was used. The operation conditions in this example are the same as in Example 14 except for the following regulation of the amount of membrane permeation water.

Regulation of the amount of membrane permeation water: flow rate regulation by transmembrane pressure difference (From start of continuous fermentation to 80 hours: regulated at 0.1 kPa or more to 5 kPa or less,
80 hours to 120 hours: regulated at 0.1 kPa or more to 2 kPa or less, and
120 hours to 180 hours: regulated at 0.1 kPa or more to 20 kPa or less)

In this example, continuous production of succinic acid by *Escherichia coli* B ATCC11303 strain as a microorganism having an ability to produce succinic acid was conducted. 150 mL of a seed culture medium consisting of 12 g/L glucose, 10 g/L polypeptone, 5 g/L yeast extract, 1 g/L $K_2HPO_4$, 1 g/L NaCl, and 0.2 g/L $MgCl_2$ was introduced into a 200-mL Erlenmeyer flask and adjusted to pH 6.8. After 7.5 g of $MgCO_3$ was added, the medium was sterilized by heating and cooled to room temperature, and ATCC11303 strain was inoculated into the medium and stationary-cultured overnight at 37° C. (preliminary preculture) The continuous fermentation apparatus shown in FIG. 2 was charged with 1.5 L of a succinic acid fermentation medium consisting of 12 g/L glucose, 10 g/L polypeptone, 5 g/L yeast extract, 1 g/L $K_2HPO_4$, 1 g/L NaCl, and 0.2 g/L $MgCl_2$, and 150 mL of the preliminary preculture was inoculated into the medium. The microorganism was cultured for 24 hours at a temperature of 37° C. while the pH was adjusted to 6.8 with 5.5M $NaCO_3$ (preculture). After preculture was finished, the microorganism was cultured while the succinic acid fermentation medium shown in Table 11 was continuously fed and the amount of membrane permeation water was regulated such that the amount of the fermentation liquor in the continuous fermentation apparatus became 1.5 L. The rate of production of succinic acid and the yield of succinic acid, calculated from the succinic acid and the glucose concentration are shown in Table 12. The transmembrane pressure difference fluctuated within 2 kPa in the whole period of continuous fermentation.

Comparative Example 9

Production of Succinic Acid by Batch Fermentation (No. 3)

Production of succinic acid by batch fermentation with *Escherichia coli* was conducted in the following manner.

100 mL of a seed culture medium consisting of 12 g/L glucose, 10 g/L polypeptone, 5 g/L yeast extract, 1 g/L $K_2HPO_4$, 1 g/L NaCl, and 0.2 g/L $MgCl_2$ was introduced into a 1250-mL Erlenmeyer flask and adjusted to pH 6.8. After 5 g of $MgCO_3$ was added, the medium was sterilized by heating and cooled to room temperature, and in an anaerobic glove box, *Escherichia coli* B ATCC11303 strain was inoculated into the medium and stationary-cultured overnight at 37° C. 1 L of a fermentation medium consisting of 12 g/L glucose, 10 g/L polypeptone, 5 g/L yeast extract, 1 g/L $K_2HPO_4$, 1 g/L NaCl, and 0.2 g/L $MgCl_2$ was adjusted to pH 6.8, added to a mini-jar fermenter (2 L, BMJ type, manufactured by ABLE) and sterilized by heating (120° C., 20 min). A $CO_2$ gas was introduced at a rate of 50 mL/min. with a sparger, and the temperature was regulated at 37° C. 100 mL of the above seed culture was inoculated into the medium and cultured under stirring at 600 rpm with an agitating blade attached thereto while the pH was adjusted to 6.8 with 5.5 M $NaCO_3$. Culture was conducted while 200 mL of 100 g/L glucose solution was added little by little such that the concentration of glucose in the culture did not exceed 20 g/L. The results are shown in Table 12.

TABLE 12

|  |  | Comparative Example 9 | Example 17 | Example 18 |
|---|---|---|---|---|
| Fermentation time | (hr) | 36 | 200 | 180 |
| Introduced glucose | (g) | 32 | 732 | 850 |
| Formed succinic acid | (g) | 3 | 72 | 81 |
| Unused glucose | (g) | 0 | 12 | 40 |
| Yield | (g/g) | 0.1 | 0.1 | 0.1 |
| Production rate | (g/L/hr) | 0.09 | 0.24 | 0.30 |

The rate of production of succinic acid was significantly improved by the method of producing a chemical product according to the present invention using the fermentation apparatuses shown in FIGS. 1 and 2.

Example 19

Production of 1,3-propanediol by Continuous Fermentation (No. 1)

Production of 1,3-propanediol was conducted by using the membrane separation-type continuous fermentation apparatus in FIG. 1 and a 1,3-propanediol production medium with the composition shown in Table 13.

First, the isolation, identification and measurement method of 1,3-propanediol as a product are described.

Conversion of glycerol into 1,3-propanediol was confirmed by HPLC. This analysis was conducted by using standard methods and materials available to those skilled in the technical field of chromatography. In one suitable method, a Waters Maxima 820 HPLC system using UV (210 nm) and RI detection was used. A sample was injected at a flow rate of 0.5 mL/min. into a Shodex SH-1011 column (8 mm×300 mm, purchased from Waters, Milford, Mass.) regulated at a temperature of 50° C. and equipped with a Shodex SH-1011P pre-column (6 mm×50 mm), with 0.01 N $H_2SO_4$ as a mobile phase. When quantitative analysis was to be conducted, trimethylacetic acid of known amount was used as an external standard to prepare the sample. Retention times of glucose (RI detection), glycerol, 1,3-propanediol (RI detection) and trimethylacetic acid (UV and RI detection) were about 15 minutes, 20 minutes, 26 minutes and 35 minutes, respectively.

Production of 1,3-propanediol was confirmed by GC/MS. This analysis was conducted by using standard methods and materials available to those skilled in the technical field of GC/MS. For example, a Hewlett Packard 5890 Series II gas chromatographic system connected to a Hewlett Packard 5971 Series mass selective detector (EI) and HP-INNOWax column (length 30 m, inner diameter 0.25 mm, film thickness 0.25 μm) was used. The retention time and mass spectrum of formed 1,3-propanediol were compared with those of standard 1,3-propanediol (m/e: 57, 58).

Derivatization of a sample was also conducted. 30 μL of conc. (70% v/v) perchloric acid was added to 1.0 mL of sample (for example, a culture supernatant). After mixing, the sample was lyophilized. A 1:1 mixture (300 μL) of bis(trimethylsilyl) trifluoroacetamide: pyridine was added to the lyophilized material, then vigorously mixed and left at 65° C. for 1 hour. The sample was made transparent by removing insoluble materials by centrifugation. The resulting liquid was separated into 2 phases, and its upper phase was used in analysis. The sample was subjected to chromatography on a DB-5 column (48 m, inner diameter 0.25 mm, film thickness 0.25 μm, from J&W Scientific), and the retention time and mass spectrum of the 1,3-propanediol derivative obtained from the culture supernatant were compared with those obtained from the standard sample. The mass spectrum TMS-derivatized 1,3-propanediol contains 205, 177, 130 and 115 atomic mass units (AMU) of characteristic ions.

The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Reaction tank capacity: 2 (L)
Used separation membrane: polyvinylidene fluoride filtration membrane
Membrane separation element effective filtration area: 120 $cm^2$
Temperature control: 37 (° C.)
Fermentation reaction tank aeration: 0.6 (L/min) nitrogen gas
Fermentation reaction tank agitation rate: 800 (rpm)
pH adjustment: adjusted to pH 7.0 with 5 N NaOH Sterilization: The culture tank including the separation membrane element, and the used medium, were sterilized with high-pressure steam in an autoclave at 121° C. for 20 minutes.

Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and
200 hours to 320 hours: regulated at 0.1 kPa or more to 20 kPa or less)

*Klebsiella pneumoniae* ATCC 25955 strain was used as the microorganism, a 1,3-propanediol fermentation medium having the composition shown in Table 13 was used as the medium, and the concentration of 1,3-propanediol as a product was evaluated by the HPLC method described above.

The concentration of glucose was measured with Glucose Test Wako C (Wako Pure Chemical Industries, Ltd.).

TABLE 13

| 1,3-Propanediol fermentation medium | |
|---|---|
| Glucose | 10 g/L |
| Glycerol | 40 g/L |
| Ammonium sulfate | 5.35 g/L |
| Potassium chloride | 0.75 g/L |
| Sodium dihydrogen phosphate | 1.38 g/L |
| Magnesium sulfate•7H$_2$O | 0.26 g/L |
| Sodium sulfate | 0.28 g/L |
| Citric acid | 0.42 g/L |
| Yeast extract | 1 g/L |
| Calcium chloride•2H$_2$O | 0.29 mg/L |
| Iron chloride•6H$_2$O | 0.025 g/L |
| Manganese chloride•6H$_2$O | 0.01 g/L |
| Zinc chloride | 0.003 g/L |
| Cobalt chloride•6H$_2$O | 0.002 g/L |
| Copper chloride•6H$_2$O | 0.85 mg/L |
| | pH 7.0 |

First, *Klebsiella pneumoniae* ATCC25955 strain was shake-cultured overnight in 5 ml of a 1,3-propanediol production medium in a test tube (prior preliminary preculture). The resulting culture was inoculated into 50 ml of a fresh. 1,3-propanediol production medium and shake-cultured for 24 hours at 30° C. in a 500-ml Sakaguchi flask (preliminary preculture). The preliminary preculture was inoculated into 1.5 L of a 1,3-propanediol production medium in the membrane separation-type continuous fermentation apparatus shown in FIG. 1, a fermentation reaction tank 1 was stirred at 800 rpm with an agitator 5 attached thereto, followed by the aeration regulation, temperature control, and pH adjustment of the reaction tank 1, and the microorganism was cultured for 24 hours (preculture). Immediately after preculture was finished, the fermentation liquor circulating pump was operated, and the microorganism was continuously cultured under the conditions where in addition to the operation conditions at the time of preculture, a membrane separation tank 2 was aerated, a 1,3-propanediol production medium (glycerol concentration: 100 g/L) was continuously fed, and the amount of membrane permeation water was regulated such that the amount of the fermentation liquor in the continuous fermentation apparatus became 1.5 L, whereby 1,3-propanediol was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of 1,3-propanediol produced in the membrane permeation fermentation liquor and the residual glucose concentration were measured at an appropriate time. The rate of production of 1,3-propanediol calculated from the 1,3-propanediol and introduced glycerol are shown in Table 14.

As a result of the fermentation test for 320 hours, stable production of 1,3-propanediol by continuous fermentation was feasible by the method of producing a chemical product according to the present invention by using the membrane separation-type continuous fermentation apparatus shown in FIG. 1. The transmembrane pressure difference fluctuated within 2 kPa in the whole period of continuous fermentation.

Example 20

Production of 1,3-propanediol by Continuous Fermentation (No. 2)

Production of 1,3-propanediol was conducted by using the continuous fermentation apparatus in FIG. 2 and a 1,3-propanediol production medium with the composition shown in Table 13.

The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation Reaction tank capacity: 2 (L)
Used separation membrane: polyvinylidene fluoride filtration membrane
Membrane separation element effective filtration area: 120 cm$^2$
Temperature control: 37 (° C.)
Fermentation reaction tank aeration: 0.6 (L/min) nitrogen gas
Fermentation reaction tank agitation rate: 800 (rpm)
pH adjustment: adjusted to pH 7.0 with 5 N NaOH
Sterilization: The culture tank including the separation membrane element, and the used medium, were sterilized with high-pressure steam in an autoclave at 121° C. for 20 minutes.
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and
200 hours to 264 hours: regulated at 0.1 kPa or more to 20 kPa or less)
*Klebsiella pneumoniae* ATCC 25955 strain was used as the microorganism, a 1,3-propanediol production medium having the composition shown in Table 9 was used as the medium, and the concentration of 1,3-propanediol as a product was measured by the HPLC method described above. The concentration of glucose was measured with Glucose Test Wako C (Wako Pure Chemical Industries, Ltd.).

First, *Klebsiella pneumoniae* ATCC25955 strain was shake-cultured overnight in 5 ml of a 1,3-propanediol production medium in a test tube (prior preliminary preculture). The resulting culture was inoculated into 50 ml of a fresh 1,3-propanediol production medium and shake-cultured for 24 hours at 30° C. in a 500-ml Sakaguchi flask (preliminary preculture). The preliminary preculture was inoculated into 1.5 L of a 1,3-propanediol production medium in the membrane separation-type continuous fermentation apparatus shown in FIG. 2, a fermentation reaction tank 1 was stirred at 800 rpm with an agitator 5 attached thereto, followed by the aeration regulation, temperature control, and pH adjustment of the fermentation reaction tank 1, and the microorganism was cultured for 24 hours (preculture). Immediately after preculture was finished, the microorganism was continuously cultured while a 1,3-propanediol production medium (glycerol concentration: 100 g/L) was continuously fed, and the amount of membrane permeation water was regulated such that the amount of the fermentation liquor in the membrane-integrated continuous fermentation apparatus became 1.5 L, whereby 1,3-propanediol was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of 1,3-propanediol produced in the membrane permeation fermentation liquor and the residual glucose concentration were measured at an appropriate time. The rate of production of 1,3-propanediol calculated from the measured 1,3-propanediol and introduced glycerol are shown in Table 14. As a result of the fermentation test for 264 hours, stable production of 1,3-propanediol by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 10

Production of 1,3-propanediol by Fed-Batch Fermentation

As a fermentation form using a microorganism, most typical fed-batch fermentation was conducted in a 2-L jar fermenter to evaluate its 1,3-propanediol productivity. The medium was used after high-pressure steam sterilization (121° C., 15 minutes). *Klebsiella pneumoniae* ATCC 25955 strain was used as the microorganism in this comparative example, the concentration of 1,3-propanediol as a product was evaluated by HPLC, and the concentration of glucose was measured with Glucose Test Wako C (Wako Pure Chemical Industries, Ltd.). The operation conditions in Comparative Example 10 are as follows:
Fermentation reaction tank capacity (amount of the 1,3-propanediol production medium): 1.0 (L)
Temperature control: 37 (° C.)
Fermentation reaction tank aeration: 0.4 (L/min) nitrogen gas
Fermentation reaction tank agitation rate: 300 (rpm)
pH adjustment: adjusted to pH 7.0 with 5 N NaOH First, *Klebsiella pneumoniae* ATCC 25955 strain was shake-cultured overnight in 5 ml of a 1,3-propanediol production medium in a test tube (preliminary preculture). The preliminary preculture was inoculated into 50 ml of a fresh 1,3-propanediol production medium and shake-cultured for 24 hours in a 500-ml Sakaguchi flask (preculture). The preculture was inoculated into 1.5 L of a 1,3-propanediol production medium in a jar fermenter. The microorganism was subjected to fed-batch fermentation by continuously feeding a 1,3-propanediol production medium (glycerol concentration: 500 g/L) such that the glycerol concentration was increased from 0 g/L to 10 g/L. The results are shown in Table 14.

TABLE 14

|  |  | Comparative Example 10 | Example 19 | Example 20 |
|---|---|---|---|---|
| Fermentation time | (hr.) | 42 | 320 | 264 |
| Introduced glycerol | (g) | 200 | 1620 | 1320 |
| Produced 1,3-propanediol | (g) | 53 | 391 | 313 |
| Unused glycerol | (g) | 5 | 55 | 50 |
| 1,3-Propanediol yield | (g/g) | 0.27 | 0.25 | 0.25 |
| 1,3-Propanediol production rate | (g/liter/hr) | 1.26 | 2.50 | 3.33 |

The rate of production of 1,3-propanediol was significantly improved by the method of producing a chemical product according to the present invention using the fermentation apparatuses shown in FIGS. 1 and 2.

Example 21

Production of Itaconic Acid by Continuous Fermentation (No. 1)

Production of itaconic acid was conducted by using the membrane separation-type continuous fermentation apparatus in FIG. 1. The medium having the composition shown in Table 15 was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 $cm^2$
Temperature control: 35 (° C.)
Fermentation reaction tank aeration: 1.5 (L/min)
Fermentation reaction tank agitation rate: 200 (rpm)
Sterilization: The culture tank including the separation membrane element, and the used medium, were sterilized with high-pressure steam in an autoclave at 121° C. for 20 minutes.
pH adjustment: adjusted to pH 5 with 4 N NaOH
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and
200 hours to 300 hours: regulated at 0.1 kPa or more to 20 kPa or less)
*Aspergillus terreus* ATCC10020 strain was used as the microorganism, an itaconic acid fermentation medium having the composition shown in Table 11 was used as the medium, the concentration of itaconic acid as a product was measured by a method of Koppeshaar ("Biseibutsu Kogaku Kouza (Bacterial Optics Course)", Vol. 5, "Kabino Riyou Kogyo (Use and Industry of Mold)" pp. 72-73, published by Kyoritsu Shuppan Co., Ltd. (1955)). The concentration of glucose was measured with Glucose Test Wako C (Wako Pure Chemical Industries, Ltd.).

TABLE 15

| Itaconic acid fermentation medium | | |
|---|---|---|
|  | Preculture | Continuous/batch fermentation |
| Glucose | 55 | 70 g/L |
| Corn steep liquor | 3 | 2.0 g/L |
| Ammonium nitrate | 5 | 3.0 g/L |
| Magnesium sulfate | 2 | 0.1 g/L |
| Adekanol LG126 (antifoaming agent) | — | 0.1 g/L |

First, *Aspergillus terreus* ATCC10020 strain was shake-cultured overnight in 5 ml of a preculture medium shown in Table 15 in a test tube (prior preliminary preculture). The resulting culture was inoculated into 100 ml of a fresh preculture medium and shake-cultured for 48 hours at 35° C. in a 500-ml Sakaguchi flask (preliminary preculture). The preliminary preculture was inoculated into 1.5 L of a continuous/batch fermentation medium in the membrane separation-type continuous fermentation apparatus shown in FIG. 1, a fermentation reaction tank 1 was stirred at 200 rpm with an agitator 5 attached thereto, followed by the aeration regulation and temperature control of the fermentation reaction tank 1, and the microorganism was cultured for 24 hours (preculture). Immediately after preculture was finished, the fermentation liquor circulating pump was operated, and the microorganism was continuously cultured under the conditions where in addition to the operation conditions at the time of preculture, a membrane separation tank 2 was aerated, anitaconic acid fermentation medium was continuously fed, and the amount of membrane permeation water was regulated such that the amount of the fermentation liquor in the membrane separation-type continuous fermentation apparatus became 2 L, whereby itaconic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of itaconic acid produced in the membrane permeation fermentation liquor and the residual glucose concentration were measured at an appropriate time. The rate of production of itaconic acid calculated from the itaconic acid and introduced glucose calculated from the glucose concentration are shown in Table 16.

Stable production of itaconic acid by continuous fermentation was feasible by the method of producing a chemical product according to the present invention by using the membrane separation-type continuous fermentation apparatus in FIG. 1. The transmembrane pressure difference fluctuated within 2 kPa in the whole period of continuous fermentation.

Example 22

Production of Itaconic Acid by Continuous Fermentation (No. 2)

Production of itaconic acid was conducted by using the continuous fermentation apparatus in FIG. 2. The medium having the composition shown in Table 15 was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2 (L)
Used separation membrane: PVDF filtration membrane
Membrane separation element effective filtration area: 120 cm$^2$
Temperature control: 35 (° C.)
Fermentation reaction tank aeration: 1.5 (L/min)
Fermentation reaction tank agitation rate: 200 (rpm)
Sterilization: The culture tank including the separation membrane element, and the used medium, were sterilized with high-pressure steam in an autoclave at 121° C. for 20 minutes.
pH adjustment: adjusted to pH 5 with 4 N NaOH
Regulation of the amount of membrane permeation water: flow rate regulation by transmembrane pressure difference
(From start of continuous fermentation to 100 hours: regulated at 0.1 kPa or more to 5 kPa or less,
100 hours to 200 hours: regulated at 0.1 kPa or more to 2 kPa or less, and
200 hours to 300 hours: regulated at 0.1 kPa or more to 20 kPa or less)

*Aspergillus terreus* ATCC10020 strain was used as the microorganism, an itaconic acid fermentation medium having the composition shown in Table 11 was used as the medium, the concentration of itaconic acid as a product was measured by the method shown in Example 17. The concentration of glucose was measured with Glucose Test Wako C (Wako Pure Chemical Industries, Ltd.)

First, *Aspergillus terreus* ATCC10020 strain was shake-cultured overnight in 5 ml of a preculture medium shown in Table 15 in a test tube (prior preliminary preculture). The resulting culture was inoculated into 100 ml of a fresh preculture medium and shake-cultured for 48 hours at 35° C. in a 500-ml Sakaguchi flask (preliminary preculture). The preliminary preculture was inoculated into 1.5 L of a continuous/batch fermentation medium in the membrane separation-type continuous fermentation apparatus shown in FIG. 2, a fermentation reaction tank 1 was stirred at 200 rpm with an agitator 5 attached thereto, followed by the aeration regulation and temperature control of the fermentation reaction tank 1, while the microorganism was cultured for 24 hours (preculture). Immediately after preculture was finished, the microorganism was continuously cultured while a continuous/batch fermentation medium was continuously fed, and the amount of membrane permeation water was regulated such that the amount of the fermentation liquor in the continuous fermentation apparatus became 1.5 L, whereby itaconic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of itaconic acid produced in the membrane permeation fermentation liquor and the residual glucose concentration were measured at an appropriate time. The rate of production of itaconic acid calculated from the itaconic acid and introduced glucose calculated from the glucose concentration is shown in Table 16.

Stable production of itaconic acid by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 11

Production of Itaconic Acid by Batch Fermentation

As a fermentation form using a microorganism, most typical batch fermentation was conducted in a 2-L jar fermenter to evaluate its itaconic acid productivity. The medium shown in Table 15 was used after high-pressure steam sterilization (121° C., 15 minutes). In Comparative Example 11, *Aspergillus terreus* ATCC10020 strain was used as the microorganism, the concentration of itaconic acid as a product was evaluated by the method shown in Example 17, and the concentration of glucose was measured with Glucose Test Wako C (Wako Pure Chemical Industries, Ltd.). The operation conditions in Comparative Example 11 are as follows Fermentation reaction tank capacity (amount of itaconic aid fermentation medium): 1.5 (L)
Temperature control: 35 (° C.)
Fermentation reaction tank aeration: 1.5 (L/min)
Fermentation reaction tank agitation rate: 200 (rpm)
pH adjustment: adjusted to pH 5 with 4 N NaOH First, ATCC10020 strain was shake-cultured overnight in 5 ml of the preculture medium shown in Table 1 in a test tube (preliminary preculture). The preliminary preculture was inoculated into 50 ml of a fresh preculture medium and shake-cultured for 48 hours in a 500-ml Sakaguchi flask (preculture). The preculture was inoculated into 1.5 L of the continuous/batch fermentation medium shown in Table 15 in a jar fermenter and subjected to batch fermentation. The results of batch fermentation are shown in Table 16.

TABLE 16

|  |  | Comparative Example 11 | Example 21 | Example 22 |
|---|---|---|---|---|
| Fermentation time | (hr) | 80 | 300 | 300 |
| Introduced glucose | (g) | 105 | 2090 | 1650 |
| Formed itaconic acid | (g) | 55 | 1020 | 790 |
| Unused glucose | (g) | 1 | 50 | 50 |
| Yield | (g/g) | 0.53 | 0.50 | 0.49 |
| Production rate | (g/L/hr) | 0.46 | 1.7 | 1.7 |

The rate of production of itaconic acid was significantly improved by the method of producing a chemical product according to the present invention using the fermentation apparatuses shown in FIGS. 1 and 2.

Example 23

Production of Cadaverine by Continuous Fermentation (No. 1)

Production of cadaverine was conducted by using the membrane separation-type continuous fermentation apparatus in FIG. 1 and a cadaverine fermentation medium with the composition shown in Table 17.

First, a method of evaluating cadaverine as a product is described. Cadaverine was evaluated by the following HPLC method.

Used column: CAPCELL PAK C18 (Shiseido Co., Ltd.)
Mobilephase: 0.1% (w/w) aqueous phosphoric acid:acetonitrile=4.5:5.5
Detection: UV 360 nm
Sample pretreatment: 25 µl of 1,4-diaminobutane (0.03 M) as an internal standard, 150 µl of sodium bicarbonate and an ethanol solution of 2,4-dinitrofluorobenzene (0.2 M) were added to, and mixed with, 25 µl analysis sample, and the mixture was kept at a temperature of 37° C. for 1 hour. 50 µl of the reaction solution was dissolved in 1 ml acetonitrile and then centrifuged at 10,000 rpm for 5 minutes, and 10 µl of the resulting supernatant was analyzed by HPLC.

The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 $cm^2$
Temperature control: 30 (° C.)
Fermentation reaction tank aeration: 1.5 (L/min) air
Fermentation reaction tank agitation rate: 860 (rpm)
pH adjustment: adjusted to pH 7.0 with 3 M HCl and 3 M ammonia water
Sterilization: The culture tank including the separation membrane element, and the used medium, were sterilized with high-pressure steam in an autoclave at 121° C. for 20 minutes.
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kpa or less, and
200 hours to 320 hours: regulated at 0.1 kPa or more to 20 kPa or less)

*Corynebacterium glutamicum* TR-CAD1 strain described in JP-A No. 2004-222569 was used as the microorganism producing cadaverine, and a cadaverine production medium having the composition shown in Table 17 was used as the medium. The concentration of cadaverine as a product was measured by the HPLC method. The concentration of glucose was measured with Glucose Test Wako C (Wako Pure Chemical Industries, Ltd.).

TABLE 17

| Cadaverine fermentation medium | |
|---|---|
| Glucose | 150 g/L |
| Citric acid | 1 g/L |
| Urea | 15 g/L |
| Potassium dihydrogen phosphate | 0.5 g/L |
| Dipotassium hydrogen phosphate | 0.5 g/L |
| Magnesium sulfate•7H$_2$O | 0.5 g/L |
| L-Threonine | 0.8 g/L |
| L-Methionine | 0.6 g/L |
| L-Leucine | 1.5 g/L |
| Iron sulfate•7H$_2$O | 6.0 mg/L |
| Manganese monohydrate | 4.2 mg/L |
| Biotin | 1.0 mg/L |
| Thiamine | 2.0 mg/L |
| Adjusted to pH 7.0 with 3 M ammonia water | |

First, *Corynebacterium glutamicum* TR-CAD1 strain was shake-cultured overnight in 5 ml of a cadaverine fermentation medium containing kanamycin (25 µg/ml) in a test tube (prior preliminary preculture). The resulting culture was inoculated into 50 ml of a fresh cadaverine production medium containing kanamycin (25 µg/ml) added and cultured for 24 hours at a temperature of 30° C. at 180 rpm with an amplitude of 30 cm in a 500-ml Sakaguchi flask (preliminary preculture). The preliminary preculture was inoculated into 2.0 L of a cadaverine fermentation medium in the membrane separation-type continuous fermentation apparatus shown in FIG. 1, a fermentation reaction tank 1 was stirred at 800 rpm with an agitator 5 attached thereto, followed by the aeration regulation, temperature control and pH adjustment of the fermentation reaction tank 1, while the microorganism was cultured for 24 hours (preculture).

Immediately after preculture was finished, the fermentation liquor circulating pump 10 was operated, and the microorganism was continuously cultured under the conditions where in addition to the operation conditions at the time of preculture, a membrane separation tank 2 was aerated, a cadaverine fermentation medium was continuously fed, and the amount of membrane permeation water was regulated such that the amount of the fermentation liquor in the continuous fermentation apparatus became 2 L, whereby cadaverine was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of lactic acid produced in the membrane permeation fermentation liquor and the residual glucose concentration were measured at an appropriate time.

The results in the continuous fermentation test for 160 hours are shown in Table 18. Stable production of cadaverine by continuous fermentation was feasible by the method of producing a chemical product according to the present invention by using the membrane separation-type continuous fermentation apparatus in FIG. 1. The transmembrane pressure difference fluctuated within 2 kPa in the whole period of continuous fermentation.

Example 24

Production of Cadaverine by Continuous Fermentation (No. 2)

Production of cadaverine was conducted by using the continuous fermentation apparatus in FIG. 2 and a cadaverine fermentation medium with the composition shown in Table 17. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 $cm^2$
Temperature control: 30 (° C.)
Fermentation reaction tank aeration: 1.5 (L/min) air
Fermentation reaction tank agitation rate: 800 (rpm)

pH adjustment: adjusted to pH 7.0 with 3 M HCl and 3 M ammonia water
Sterilization: The culture tank including the separation membrane element, and the used medium, were sterilized with high-pressure steam in an autoclave at 121° C. for 20 minutes.
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 0.1 kPa or more to 2 kPa or less, and
200 hours to 264 hours: regulated at 0.1 kPa or more to 20 kPa or less)

*Corynebacterium glutamicum* TR-CAD1 strain was used as the microorganism, a cadaverine fermentation medium having the composition shown in Table 17 was used as the medium, and the concentration of cadaverine as a product was measured by the HPLC method. The concentration of glucose was measured with Glucose Test Wako C (Wako Pure Chemical Industries, Ltd.)

First, *Corynebacterium glutamicum* TR-CAD1 strain was shake-cultured overnight in 5 ml of a cadaverine production medium containing kanamycin (25 μg/ml) added in a test tube (prior preliminary preculture). The resulting culture was inoculated into 50 ml of a fresh cadaverine production medium containing kanamycin (25 μg/ml) added and cultured for 24 hours at a temperature of 30° C. at 180 rpm with an amplitude of 30 cm in a 500-ml Sakaguchi flask (preliminary preculture).

The preliminary preculture was inoculated into 1.5 L of a cadaverine production medium in the membrane separation-type continuous fermentation apparatus shown in FIG. 2, a fermentation reaction tank 1 was stirred at 800 rpm with an agitator 5 attached thereto, followed by the aeration regulation, temperature control and pH adjustment of the fermentation reaction tank 1, while the microorganism was cultured for 24 hours (preculture). Immediately after preculture was finished, the microorganism was continuously cultured while a cadaverine fermentation medium was continuously fed, and the amount of membrane permeation water was regulated such that the amount of the fermentation liquor in the continuous fermentation apparatus became 1.5 L, whereby cadaverine was produced by continuous fermentation Regulation of the amount of membrane permeation water in the continuous fermentation test was conducted by appropriately changing the water head difference with a water head difference regulating apparatus 3 such that the water head difference of the fermentation reaction tank was within 2 m, that is, the transmembrane pressure difference was within 20 kPa. The concentration of cadaverine produced in the membrane permeation fermentation liquor and the residual glucose concentration were measured at an appropriate time. The rate of production of cadaverine calculated from the cadaverine and introduced glucose is shown in Table 18.

The results in the continuous fermentation test for 320 hours are shown in Table 18. Stable production of cadaverine by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 12

Production of Cadaverine by Batch Fermentation

As a fermentation form using a microorganism, most typical batch fermentation was conducted in a 2-L jar fermenter to evaluate its cadaverine productivity. The medium was used after high-pressure steam sterilization (121° C., 15 minutes)

In this comparative example, *Corynebacterium glutamicum* TR-CAD1 strain was used as the microorganism, the concentration of cadaverine as a product was evaluated by the HPLC method, and the concentration of glucose was measured with Glucose Test Wako C (Wako Pure Chemical Industries, Ltd.). The operation conditions in Comparative Example 8 are as follows:
Fermentation reaction tank capacity (amount of cadaverine production medium): 1.0 (L)
Temperature control: 35 (° C.)
Fermentation reaction tank aeration: 1.5 (L/min) air
Fermentation reaction tank agitation rate: 800 (rpm)
pH adjustment: adjusted to pH 7.0 with 3 M HCl and 3 M ammonia water First, *Corynebacterium glutamicum* TR-CAD1 strain was shake-cultured overnight in 5 ml of a cadaverine production medium containing kanamycin (25 μg/ml) added in a test tube (preliminary preculture). The resulting culture was inoculated into 50 ml of a fresh cadaverine production medium containing kanamycin (25 μg/ml) added and cultured for 24 hours at a temperature of 30° C. at 180 rpm with an amplitude of 30 cm in a 500-ml Sakaguchi flask (preculture).

The preculture was inoculated into 1.0 L of a cadaverine production medium (glucose concentration: 100 g/L) in a jar fermenter. The microorganism was subjected to batch fermentation with the cadaverine production medium. The results are shown in Table 18.

TABLE 18

|  |  | Comparative Example 12 | Example 23 | Example 24 |
|---|---|---|---|---|
| Fermentation time | (hr) | 30 | 160 | 144 |
| Introduced glucose | (g) | 100 | 2460 | 2210 |
| Produced cadaverine | (g) | 2.6 | 60.4 | 56.2 |
| Unused glucose | (g) | 0 | 45 | 50 |
| Cadaverine yield | (g/g) | 2.6 | 2.5 | 2.5 |
| Cadaverine production rate | (g/L/hr) | 0.087 | 0.200 | 0.260 |

It could be revealed that the rate of production of cadaverine was significantly improved by the method of producing a chemical product according to the present invention using the fermentation apparatuses shown in FIGS. 1 and 2.

Example 25

Production of Nucleic Acids by Continuous Fermentation (No. 1)

Production of nucleic acids was conducted by using the membrane separation-type continuous fermentation apparatus in FIG. 1. The medium shown in Table 19 was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane Membrane separation element effective filtration area: 120 cm$^2$
Temperature control: 30 (° C.)
Fermentation reaction tank aeration: 1000 (mL/min)
Fermentation reaction tank agitation rate: 800 (rpm)
Sterilization: The culture tank including the separation membrane element, and the used medium, were sterilized with high-pressure steam in an autoclave at 121° C. for 20 minutes.
pH adjustment: adjusted to pH 6.8 with 25% aqueous ammonia
Regulation of the amount of membrane permeation water: flow rate regulation by transmembrane pressure difference (From start of continuous fermentation to 150 hours: regulated at 0.1 kPa or more to 5 kPa or less,
150 hours to 300 hours: regulated at 0.1 kPa or more to 2 kPa or less, and
300 hours to 400 hours: regulated at 0.1 kPa or more to 20 kPa or less)

*Corynebacterium ammoniagenes* ATCC21479 was used as the prokaryotic microorganism, and a nucleic acid fermentation medium having the composition shown in Table 19 was used as the medium. The concentrations of guanosine and inosine contained in a fermentation liquor were confirmed by measuring the amounts of the respective nucleic acids by HPLC under the following conditions:
(Analysis Conditions)
Column: Asahipak GS-220 (7.6 mmID×500 mL), buffer: 0.2M NaH$_2$PO$_4$ (pH 3.98) with pH adjusted with phosphoric acid, temperature: 55° C., flow rate: 1.5 ml/min, detection: UV 254 nm, retention time (min): inosine 16.1, guanosine 20.5.

The concentration of glucose was measured with Glucose Test Wako C (registered trademark) (Wako Pure Chemical Industries, Ltd.).

TABLE 19

Nucleic acid fermentation medium

|  | Preculture | Batch fermentation | Continuous fermentation |
| --- | --- | --- | --- |
| Glucose | 20 | 150 | 150 g/L |
| Potassium dihydrogen phosphate |  | 10 | 10 g/L |
| Potassium hydrogen phosphate |  | 10 | 10 g/L |
| Magnesium sulfate |  | 10 | 10 g/L |
| Calcium chloride |  | 1 | 1 g/L |
| Iron sulfate |  | 10 | 10 mg/L |
| Zinc sulfate |  | 1 | 1 mg/L |
| Thiamine |  | 5 | 5 mg/L |
| Calcium pantothenate |  | 10 | 10 mg/L |
| Cysteine |  | 20 | 20 mg/L |
| Biotin |  | 30 | 30 ug/L |
| Urea |  | 2 | 2 g/L |
| Meat extract | 10 | 10 | 10 g/L |
| Adenine |  | 300 | 300 mg/L |
| Hypoxanthine |  | 100 | 100 mg/L |
| Peptone | 10 | 10 | 1 g/L |
| Yeast extract | 10 | 10 | 1 g/L |
| Sodium chloride | 3 | 3 | 3 g/L |

First, *Corynebacterium ammoniagenes* ATCC21479 was shake-cultured in 150 ml of the preculture medium shown in Table for 24 hours at a temperature of 30° C. in a Sakaguchi flask (preliminary preculture). The preliminary preculture was inoculated into 1 L of a preculture medium in the membrane separation-type continuous fermentation apparatus shown in FIG. 1, a fermentation reaction tank 1 was stirred at 800 rpm with an agitator 5 attached thereto, followed by the aeration regulation and temperature control at 30° C. of the reaction tank 1, while the microorganism was cultured for 24 hours (preculture). Immediately after preculture was finished, the fermentation liquid circulating pump was operated, and the microorganism was continuously cultured under the conditions where in addition to the operation conditions at the time of preculture, the membrane separation tank 2 was aerated, the continuous fermentation medium was fed continuously, and after the preculture was finished, the continuous fermentation medium was fed continuously, and the fermentation medium was circulated between the fermentation reaction tank 1 and the membrane separation tank 12 by the fermentation liquor circulating pump 11, and the amount of membrane permeation water was regulated such that the amount of the fermentation liquor in the membrane separation-type continuous fermentation apparatus became 2 L, whereby nucleic acids were produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of nucleic acids produced in the membrane permeation fermentation liquor and the residual glucose concentration were measured at an appropriate time. The rate of production of nucleic acids calculated from nucleic acid and introduced glucose calculated from the glucose concentration is shown in Table 20.

As a result of the fermentation test for 400 hours, stable production of nucleic acids by continuous fermentation was feasible by the method of producing a chemical product according to the present invention by using the continuous fermentation apparatus in FIG. 1. The transmembrane pressure difference fluctuated within 2 kPa in the whole period of continuous fermentation.

Example 26

Production of Nucleic Acids by Continuous Fermentation (No. 2)

Production of nucleic acids was conducted by using the continuous fermentation apparatus in FIG. 2. The medium shown in Table 19 was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 cm$^2$
Temperature control: 30 (° C.)
Fermentation reaction tank aeration: 1000 (mL/min)
Fermentation reaction tank agitation rate: 800 (rpm)
Sterilization: The culture tank including the separation membrane element, and the used medium, were sterilized with high-pressure steam in an autoclave at 121° C. for 20 minutes.

pH adjustment: adjusted to pH 6.8 with 25% aqueous ammonia
Regulation of the amount of membrane permeation water: flow rate regulation by transmembrane pressure difference
(From start of continuous fermentation to 150 hours: regulated at 0.1 kPa or more to 5 kPa or less,
150 hours to 300 hours: regulated at 0.1 kPa or more to 2 kPa or less, and
300 hours to 400 hours: regulated at 0.1 kPa or more to 20 kPa or less)

*Corynebacterium ammoniagenes* ATCC21479 was used as the prokaryotic microorganism, and a nucleic acid fermentation medium having the composition shown in Table 19 was used as the medium. The concentrations of guanosine, inosine and glucose contained in a fermentation liquor were confirmed by measuring the amounts of the respective nucleic acids in the same manner as in Example 1.

First, *Corynebacterium ammoniagenes* ATCC21479 was shake-cultured for 24 hours at a temperature of 30° C. in 150 ml of a preculture medium shown in Table 19 in a Sakaguchi flask (preliminary preculture). The preliminary preculture was inoculated into 1 L of a preculture medium in the membrane separation-type continuous fermentation apparatus shown in FIG. 2, a fermentation reaction tank 1 was stirred at 800 rpm with an agitator 5 attached thereto, followed by the aeration regulation and temperature control at 30° C. of the reaction tank 1, while the microorganism was cultured for 24 hours (preculture).

Immediately after preculture was finished, the continuous fermentation medium was continuously fed, and the microorganism was continuously cultured while the amount of membrane permeation water was regulated such that the amount of the fermentation liquor in the continuous fermentation apparatus be came 1.5 L, whereby nucleic acids were produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of nucleic acids produced in the membrane permeation fermentation liquor and the residual glucose concentration were measured at an appropriate time. The rate of production of nucleic acids calculated from nucleic acid and introduced glucose calculated from the glucose concentration is shown in Table 20.

As a result of the fermentation test for 400 hours, stable production of nucleic acids by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 13

Production of Nucleic Acids by Batch Fermentation

As a fermentation form using a microorganism, most typical batch fermentation was conducted in a 2-L jar fermenter to evaluate its nucleic acid productivity. The continuous fermentation medium shown in Table 19 was used after high-pressure steam sterilization (121° C., 15 minutes). In this comparative example, *Corynebacterium ammoniagenes* ATCC21479 was used as the prokaryotic microorganism, the concentrations of nucleic acids as the product was evaluated by the method shown in Example 21, and the concentration of glucose was measured with Glucose Test Wako C (registered trademark) (Wako Pure Chemical Industries, Ltd.). The operation conditions in this comparative example are as follows:
Fermentation reaction tank capacity: 2 (L)
Temperature control: 30 (° C.)
Fermentation reaction tank aeration: 1000 (mL/min)
Fermentation reaction tank agitation rate: 800 (rpm)
Sterilization: The culture tank including the separation membrane element, and the used medium, were sterilized with high-pressure steam in an autoclave at 121° C. for 20 minutes.
pH adjustment: adjusted to pH 6.8 with 25% aqueous ammonia First, *Corynebacterium ammoniagenes* ATCC21479 was shake-cultured for 24 hours at a temperature of 30° C. in 150 ml of the preculture medium shown in Table 19 in a Sakaguchi flask (preculture). The resulting preculture was inoculated into 1 L of the continuous fermentation medium shown in Table 19 in a jar fermenter and subjected to batch fermentation. After fermentation was initiated, 5% glucose was added so that fermentation was continued. The results of batch fermentation for 120 hours are shown in Table 20.

TABLE 20

|  |  | Comparative Example 13 | | Example 25 | | Example 26 | |
| --- | --- | --- | --- | --- | --- | --- | --- |
| Fermentation time | (hr) | 120 | | 400 | | 400 | |
| Introduced glucose | (g) | 200 | 4530 | 4690 | | | |
| Formed nucleic acid | | | | | | | |
| Inosine Guanosine | (g) | 50 | 2 | 906 | 23 | 878 | 23 |
| Unused glucose | (g) | 0 | | 80 | | 70 | |
| Yield | | | | | | | |
| Inosine Guanosine | (g/g) | 0.25 | 0.01 | 0.20 | 0.005 | 0.19 | 0.005 |
| Production rate (Inosine + guanosine) | (g/L/hr) | 0.47 | | 2.3 | | 2.3 | |

It could be revealed that the rate of production of nucleic acids was significantly improved by the method of producing a chemical product according to the present invention using the fermentation apparatus shown in FIGS. 1 and 2.

Example 27

Production of L-threonine by Continuous Fermentation (No. 1)

Production of L-threonine was conducted by using the membrane separation-type continuous fermentation apparatus in FIG. 1 and a fermentation medium with the composition shown in Table 21.

First, a method of evaluating L-threonine as a product is described. The amount of L-threonine contained in a culture was measured by the following method. 25 µL of a L-threonine-containing culture to be measured was removed and then added with 150 µl of NaHCO$_3$ (75 mM) and 25 µl of internal standard L-methionine (2 g/L). Further, 900 µl ethanol and 150 µl DNFB (0.2 M) were added to, and mixed with, the above solution. The resulting solution was left at 37° C. for 1 hour and analyzed by HPLC under the following conditions:
Used column: CAPCELLPAK C18 TYPE SG120 (Shiseido Co., Ltd.)
Mobile phase: 0.1% (w/v) H$_3$PO$_4$:acetonitrile=7:3 (flow rate 1.2 mL/min)
Detection: UV (360 nm)
Temperature: 23° C.

A calibration curve was prepared by analyzing L-threonine samples of known concentration as a sample and plotting their L-threonine concentrations on the abscissa and the area ratio (L-threonine area/L-methionine (internal standard) area ratio) on the ordinate. The medium was used after high-pressure steam sterilization (121° C., 15 minutes) As the separation membrane, the porous membrane prepared in Reference Example 2 was used.

Unless otherwise noted, the operation conditions in this example are as follows:
Reaction tank capacity: 2 (L)
Membrane separation tank capacity: 0.5 (L)
Used separation membrane: polyvinylidene fluoride filtration membrane
Membrane separation element effective filtration area: 60 cm$^2$
Temperature control: 37 (° C.)
Reaction tank aeration: 1.5 (L/min)
Membrane separation tank aeration: 1 (L/min)
Reaction tank agitation rate: 800 (rpm)
pH adjustment: adjusted to pH 7 with 28% aqueous ammonia
L-Threonine fermentation medium feed rate: variable control in the range of 50 to 300 ml/hr.
Regulation of the amount of membrane permeation water: flow rate regulation by transmembrane pressure difference
(From start of continuous fermentation to 100 hours: regulated at 0.1 kPa or more to 5 kPa or less and
100 hours to 200 hours: regulated at 0.1 kPa or more to 2 kPa or less)

In *Providencia rettgeri*, *Providencia rettgeri* SGR588-77 (FERM P-10528) was used as the microorganism producing L-threonine, a fermentation medium having the composition shown in Table 21 was used as the medium, the concentration of L-threonine as a product was measured by the HPLC method described above, and the concentration of glucose was measured with Glucose Test Wako C (Wako Pure Chemical Industries, Ltd.).

TABLE 21

L-Threonine fermentation medium

| Medium components | | Fermentation medium | Preculture medium | Batch medium additional medium |
|---|---|---|---|---|
| Glucose | g/L | 120 | 50 | 750 |
| Ammonium sulfate | g/L | 5 | 5 | — |
| Potassium dihydrogen phosphate | g/L | 1 | 1 | 5 |
| Magnesium sulfate•7H$_2$O | g/L | 0.4 | 0.4 | 2 |
| Iron sulfate•7H$_2$O | ppm | 2 | 2 | — |
| Magnesium sulfate•5H$_2$O | ppm | 2 | 2 | — |
| L-Isoleucine | mg/L | 10 | 50 | 200 |

First, *Providencia rettgeri* SGR588-77 scraped off from an agar medium was inoculated into 100 ml of a glucose-bouillon medium (1% glucose, 3% bouillon (manufactured by Nissui Co., Ltd.)) in a 500-ml Erlenmeyer flask and cultured at 37° C. under stirring at 140 rpm (preliminary preculture). The preliminary preculture was inoculated into 1.5 L of a preculture medium (Table 21) in the membrane separation-type continuous fermentation apparatus shown in FIG. 1, a reaction tank 1 was stirred at 800 rpm with an agitator 5 attached thereto, followed by the aeration regulation and temperature control at 37° C. of the reaction tank 1, while the microorganism was cultured for 24 hours (preculture). Immediately after preculture was finished, the fermentation liquor circulating pump was operated, and the microorganism was cultured under conditions where in addition to the operation conditions at the time of preculture, the membrane separation tank 2 was aerated, and a fermentation medium having the composition shown in Table 17 was continuously fed, and the amount of membrane permeation water was regulated such that the amount of the fermentation liquor in the continuous fermentation apparatus became 2 L, whereby L-threonine was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of L-threonine produced in the membrane permeation fermentation liquor and the residual glucose concentration were measured at an appropriate time. The water head difference was appropriately changed such that the water head of the fermentation reaction tank was 2 m or less at maximum, that is, the transmembrane pressure difference was within 20 kPa. The concentration of L-threonine produced in the membrane permeation fermentation liquor and the residual glucose concentration were measured at an appropriate time. The results of the continuous fermentation test for 200 hours are shown in Table 22.

Stable production of L-threonine by continuous fermentation was feasible by the method of producing a chemical product according to the present invention by using the membrane separation-type continuous fermentation apparatus in FIG. 1. The transmembrane pressure difference fluctuated within 2 kPa in the whole period of continuous fermentation.

Example 28

Production of L-threonine by Continuous Fermentation (No. 2)

Production of L-threonine was conducted by using the continuous fermentation apparatus in FIG. 2 and a fermentation medium with the composition shown in Table 21. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:

Reaction tank capacity: 2 (L)
Used separation membrane: PVDF filtration membrane
Membrane separation element effective filtration area: 120 cm$^2$
Temperature control: 37 (° C.)
Reaction tank aeration: 1.5 (L/min)
Reaction tank agitation rate: 800 (rpm)
pH adjustment: adjusted to pH 7 with 25% aqueous ammonia
L-Threonine fermentation medium feed rate: variable control in the range of 50 to 300 ml/hr.
Regulation of the amount of membrane permeation water: flow rate regulation by transmembrane pressure difference (From start of continuous fermentation to 100 hours: regulated at 0.1 kPa or more to 5 kPa or less and 100 hours to 200 hours: regulated at 0.1 kPa or more to 2 kPa or less)
Sterilization: The culture tank including the separation membrane element, and the used medium, were sterilized with high-pressure steam in an autoclave at 121° C. for 20 minutes.

In *Providencia rettgeri*, *Providencia rettgeri* SGR588-77 (FERM P-10528) was used as the microorganism producing L-threonine, a fermentation medium having the composition shown in Table 21 was used as the medium, the concentration of L-threonine as a product was measured by HPLC shown in Example 23, and the concentration of glucose was measured with Glucose Test Wako C (Wako Pure Chemical Industries, Ltd.).

First, *Providencia rettgeri* SGR588-77 scraped off from an agar medium was inoculated into 100 ml of a glucose-bouillon medium (1% glucose, 3% bouillon (manufactured by Nissui Co., Ltd.)) in a 500-ml Erlenmeyer flask. The microorganism was cultured at 37° C. under stirring at 140 rpm (preliminary preculture). The preliminary preculture was inoculated into 1.5 L of a preculture medium (Table 21) in the continuous fermentation apparatus shown in FIG. 1, a reaction tank 1 was stirred at 8.00 rpm with an agitator 5 attached thereto, followed by the aeration regulation, temperature control and pH adjustment of the reaction tank 1, while the microorganism was cultured for 24 hours (preculture). Immediately after preculture was finished, the microorganism was continuously cultured while a fermentation medium having the composition shown in Table 21 was continuously fed, and the amount of membrane permeation water was regulated such that the amount of the fermentation liquor in the continuous fermentation apparatus became 1.5 L, whereby L-threonine was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of L-threonine produced in the membrane permeation fermentation liquor and the residual glucose concentration were measured at an appropriate time. The yield of L-threonine relative to sugar and the rate of production of lactic acid based on the L-threonine and introduced glucose calculated from the glucose concentration are shown in Table 18.

As a result of the fermentation test for 200 hours, stable production of L-threonine by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 14

Production of L-threonine by Batch Fermentation

As a fermentation form using a microorganism, most typical batch fermentation was conducted in a 2-L jar fermenter to evaluate its L-threonine productivity. The preculture medium shown in Table 21 was used as a medium when batch culture was initiated. These mediums were used after high-pressure steam sterilization (121° C., 15 minutes). In this comparative example, *Providencia rettgeri* SGR588-77 was used as the microorganism, the concentrations of L-threonine and glucose contained in the fermentation liquor were measured by the method shown in Example 27. The operation conditions in this comparative example are as follows:

Fermentation reaction tank capacity (amount of L-threonine fermentation medium): 1 (L)
Temperature control: 37 (° C.)
Fermentation reaction tank aeration: 1 (L/min)
Fermentation reaction tank agitation rate: 800 (rpm)
pH adjustment: adjusted to pH 7 with 28% aqueous ammonia First, *Providencia rettgeri* SGR588-77 scraped off from an agar medium was inoculated into 90 ml of a glucose-bouillon medium (1% glucose, 3% bouillon (manufactured by Nissui Co., Ltd.)) in a 500-ml Erlenmeyer flask. The microorganism was cultured at 37° C. under stirring at 140 rpm (preculture). The preculture was inoculated into 810 ml of the preculture medium shown in Table 17 in a mini-jar fermenter and subjected to batch fermentation. The composition of a medium added during culture is shown in additional medium in Table 9. The medium was added 24, 32, 40 and 48 hours after initiation of culture in an amount 50 mL respectively. The results of batch fermentation are shown in Table 22.

TABLE 22

|  |  | Comparative Example 14 | Example 27 | Example 28 |
|---|---|---|---|---|
| Fermentation time | (hr) | 55 | 200 | 200 |
| Introduced glucose | (g) | 195 | 2350 | 2290 |
| Formed L-threonine | (g) | 67.3 | 766 | 727 |
| Unused glucose | (g) | 0 | 98 | 87 |
| Yield | (g/g) | 0.345 | 0.34 | 0.33 |
| Production rate | (g/L/hr) | 1.11 | 1.9 | 2.5 |

It could be revealed that the rate of production of L-threonine was significantly improved by the method of producing a chemical product according to the present invention using the fermentation apparatus shown in FIGS. 1 and 2.

Example 29

Production of L-Lactic Acid by Continuous Fermentation Using a Lactic Acid Bacterium (No. 1)

Production of L-lactic acid was conducted by using the membrane separation-type continuous fermentation apparatus in FIG. 1. The L-lactic acid bacterium lactic acid fermentation medium shown in Table 23 was used after high-pressure steam sterilization (121° C., 15 minutes). As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 cm$^2$
Temperature control: 37 (° C.)
Fermentation reaction tank aeration: 50 (mL/min) nitrogen
Fermentation reaction tank agitation rate: 600 (rpm)
Sterilization: The culture tank including the separation membrane element, and the used medium, were sterilized with high-pressure steam in an autoclave at 121° C. for 20 minutes.
pH adjustment: adjusted to pH 6.5 with 8 N aqueous ammonia
Regulation of the amount of membrane permeation water: flow rate regulation by transmembrane pressure difference
(From start of continuous fermentation to 150 hours: regulated at 0.1 kPa or more to 5 kPa or less,
150 hours to 300 hours: regulated at 0.1 kPa or more to 2 kPa or less, and
300 hours to 400 hours: regulated at 0.1 kPa or more to 20 kPa or less)
*Lactococcus lactis* JCM7638 strain was used as the prokaryotic microorganism, and a lactic acid bacterium lactic acid fermentation medium having the composition shown in Table 23 was used as the medium. The concentration of L-lactic acid contained in a fermentation liquor was evaluated by the same method as in Reference Example 1. The concentration of glucose was measured with Glucose Test Wako C (Wako Pure Chemical Industries, Ltd.).

TABLE 23

| Lactic bacterium lactic acid fermentation medium | |
|---|---|
| Glucose | 60 g/L |
| Yeast extract | 5 g/L |
| Polypeptone | 5 g/L |
| Sodium chloride | 5 g/L |

First, *Lactococcus lactis* JCM7638 strain was static-cultured in 5 ml of the nitrogen gas-purged lactic acid fermentation medium shown in Table 23 for 24 hours at a temperature of 37° C. in a test tube (prior preliminary preculture). The resulting culture was inoculated into 50 ml of fresh, nitrogen gas-purged lactic acid fermentation medium and static-cultured for 48 hours at 37° C. (preliminary preculture). The preliminary preculture was inoculated into 1.5 L of a fresh, nitrogen gas-purged lactic acid fermentation medium in the membrane separation-type continuous fermentation apparatus shown in FIG. 1, a fermentation reaction tank 1 was stirred at 600 rpm with an agitator 5 attached thereto, followed by the aeration regulation and temperature control at 37° C. of the reaction tank 1, while the microorganism was cultured for 24 hours (preculture) Immediately after preculture was finished, the microorganism was continuously cultured in a continuously fed lactic acid fermentation medium while the amount of membrane permeation water was regulated such that the amount of the fermentation liquor in the continuous fermentation apparatus became 2 L, whereby L-lactic acid was produced by continuous fermentation. At this time, a nitrogen gas was fed from a gas feeding apparatus to the fermentation reaction tank, and the discharged gas was recovered and fed again into the fermentation reaction tank. That is, the nitrogen gas-containing gas was supplied by recycling. In this continuous fermentation test, the amount of membrane permeation water was regulated and changed under the membrane permeation water control conditions described above, during which the water head difference was measured as transmembrane pressure difference with a water head difference regulating apparatus 3. The concentration of L-lactic acid produced in the membrane permeation fermentation liquor and the residual glucose concentration were measured at an appropriate time. The yield of L-lactic acid relative to sugar and the rate of production of L-lactic acid, calculated from the L-lactic acid and introduced glucose calculated from the glucose concentration are shown in Table 24.

As a result of the fermentation test for 400 hours, stable production of L-lactic acid by continuous fermentation was feasible by the method of producing a chemical product according to the present invention by using the membrane separation-type continuous fermentation apparatus. The transmembrane pressure difference fluctuated within 2 kPa in the whole period of continuous fermentation.

Example 30

Production of L-Lactic Acid by Continuous Fermentation Using a Lactic Acid Bacterium (No. 2)

Production of L-lactic acid was conducted by using the continuous fermentation apparatus in FIG. 2. As a medium, the lactic acid bacterium lactic acid fermentation medium shown in Table 23 was used after high-pressure steam sterilization (121° C., 15 minutes). The medium was used after high-pressure steam sterilization (121° C., 15 minutes). As the separation membrane, the porous membrane prepared in Reference Example 2 was used. Unless otherwise noted, the operation conditions in this example are as follows:
Fermentation reaction tank capacity: 2 (L)
Used separation membrane: polyvinylidene fluoride filtration membrane
Membrane separation element effective filtration area: 120 cm$^2$
Temperature control: 37 (° C.)
Fermentation reaction tank aeration: 50 (mL/min) nitrogen
Fermentation reaction tank agitation rate: 600 (rpm)
Sterilization: The culture tank including the separation membrane element, and the used medium, were sterilized with high-pressure steam in an autoclave at 121° C. for 20 minutes.
pH adjustment: adjusted to pH 6.5 with 8 N aqueous ammonia
Regulation of the amount of membrane permeation water: flow rate regulation by transmembrane pressure difference
(From start of continuous fermentation to 150 hours: regulated at 0.1 kPa or more to 5 kPa or less,
150 hours to 300 hours: regulated at 0.1 kPa or more to 2 kPa or less, and 300 hours to 400 hours: regulated at 0.1 kPa or more to 20 kPa or less)

*Lactococcus lactis* JCM7638 strain was used as the prokaryotic microorganism and cultured in the same manner as in Example 29 until preculture. Immediately after preculture was finished, the microorganism was continuously cultured in a continuously fed medium while the amount of membrane permeation water was regulated such that the amount of the fermentation liquor in the continuous fermentation apparatus became 1.5 L, whereby L-lactic acid was produced by continuous fermentation. At this time, a nitrogen gas was fed from a gas feeding apparatus to the fermentation reaction tank, and the discharged gas was recovered and fed again into the fermentation reaction tank. That is, the nitrogen gas-containing gas was supplied by recycling. In this continuous fermentation test, the amount of membrane permeation water was regulated and changed under the membrane permeation water control conditions described above, during which the water head difference was measured as transmembrane pressure difference with a water head difference regulating apparatus 3. The concentration of L-lactic acid produced in the membrane permeation fermentation liquor and the residual glucose concentration were measured at an appropriate time. The yield of L-lactic acid relative to sugar calculated from the L-lactic acid and introduced glucose calculated from the glucose concentration, and the rate of production of L-lactic acid are shown in Table 24.

As a result of the fermentation test for 400 hours, stable production of L-lactic acid by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 15

Production of L-lactic Acid by Batch Fermentation

As a fermentation form using a microorganism, most typical batch fermentation was conducted in a 2-L jar fermenter to evaluate its L-lactic acid productivity. The medium shown in Table 23 was used after high-pressure steam sterilization (121° C., is minutes). In this comparative example, *Lactococcus lactis* JCM7638 strain was used as the prokaryotic microorganism, the concentration of L-lactic acid as a product was evaluated by the method shown in Reference Example 1. The concentration of glucose was measured with Glucose Test Wako C (Wako Pure Chemical Industries, Ltd.). The operation conditions in this comparative example are as follows:

Fermentation reaction tank capacity: 1 (L)
Temperature control: 37 (° C.)
Fermentation reaction tank aeration: 50 (mL/min) nitrogen
Fermentation reaction tank agitation rate: 200 (rpm)
pH adjustment: adjusted to pH 6.5 with 8 N aqueous ammonia First, *Lactococcus lactis* JCM7638 strain was static-cultured in 5 ml of the nitrogen gas-purged lactic acid fermentation medium shown in Table 23 for 24 hours at 37° C. (preliminary preculture). The resulting culture was inoculated into 50 ml of a fresh, nitrogen gas-purged lactic acid fermentation medium and static-cultured for 48 hours at a temperature of 37° C. (preculture). The resulting preculture was inoculated into 1 L of the continuous/batch fermentation medium shown in Table 23 in a jar fermenter and subjected to batch fermentation. The results of batch fermentation are shown in Table 24.

TABLE 24

|  |  | Comparative Example 15 | Example 29 | Example 30 |
|---|---|---|---|---|
| Fermentation time | (hr) | 40 | 400 | 400 |
| Introduced glucose | (g) | 90 | 4460 | 3550 |
| Formed L-lactic acid | (g) | 83 | 3920 | 3060 |
| Unused glucose | (g) | 0 | 60 | 70 |
| Yield | (g/g) | 0.92 | 0.89 | 0.88 |
| Production rate | (g/L/hr) | 2.1 | 4.9 | 5.1 |

It could be revealed that the rate of production of L-lactic acid was significantly improved by the method of producing a chemical product according to the present invention using the fermentation apparatus shown in FIGS. 1 and 2.

Reference Example 6

Preparation of Chromosomal DNA of *Bacillus laevolacticus* JCM2513 Strain

*Bacillus laevolacticus* JCM2513 strain was inoculated into a 100-ml GYP medium (GYP medium described in JP-A No. 2003-088392) and cultured at a temperature of 30° C. for 24 hours to obtain a culture. The resulting culture was centrifuged at 3000 rpm for 15 minutes to obtain 0.5 g moistened microorganism, and from the moistened microorganism, chromosomal DNA was obtained by a method of Saito and Miura (Biochem. Biophys. Acta., 72, 619 (1963)). Then, 60 µg of the chromosomal DNA and 3 U of a restriction enzyme Sau3AI were mixed in 10 mM Tris-HCl buffer (50 mM NaCl, 10 mM $MgSO_4$ and 1 mM dithiothreitol (pH 7.4)) and reacted at a temperature of 37° C. for 30 minutes. The reaction solution was extracted with phenol and precipitated with ethanol in a usual manner to obtain 50 µg of Sau3AI-digested chromosomal DNA fragment of *Bacillus laevolacticus* JCM2513 strain.

Reference Example 7

Preparation of a Gene Library of *Bacillus laevolacticus* JCM2513 Strain by Utilizing a Plasmid Vector DNA 20 µg of a plasmid vector DNA (pUC19) capable of autonomously replicating in *Escherichia coli* and 200 U of a restriction enzyme BamHI were mixed in 50 mM Tris-HCl buffer (containing 100 mM NaCl, 10 mM magnesium sulfate (pH 7.4)) and reacted at a temperature of 37° C. for 2 hours to obtain a digestion solution, and the digestion solution was extracted with phenol and precipitated with ethanol in a usual manner.

Thereafter, the plasmid vector-derived DNA fragment was dephosphorylated by treatment with a bacterial alkali phosphatase for preventing re-bonding, extracted with phenol and precipitated with ethanol in a usual manner.

1 µg of this BamHI-digested pUC19, and 1 µg of the chromosomal DNA fragment of *Bacillus laevolacticus* JCM2513 strain digested with Sau3AI, obtained in Reference Example 6, and 2 U of T4 DNA ligase (manufactured by Takara Shuzo Co., Ltd.), were added to 66 mM Tris-HCl buffer (pH 7.5) containing 66 mM magnesium chloride, 10 mM dithiothreitol and 10 mM ATP and reacted at a temperature of 16° C. for 16 hours to ligate the DNAs. Then, the resulting DNA mixture was used in a usual manner to transform *Escherichia coli* JM109 which was then plated on an LB agar medium containing 50 μg/ml ampicillin sodium, to obtain about 20,000 colonies for use as a gene library. From the about 20,000 colonies, a recombinant DNA was recovered. The recovery method followed the method of Saito & Miura supra described above.

Reference Example 8

Preparation of a Host for Screening D-Lactate Dehydrogenase Gene

Screening of D-LDH gene from *Bacillus laevolacticus* JCM2513 strain was conducted by functional complementation. The principle is described in detail in "DOMINIQUE, G., Appl Environ Microbiol, United States (1995) 61 266-272)". That is, it is necessary to prepare a strain of *Escherichia coli* made deficient in D-lactate dehydrogenase activity and in pyruvate formate-lyase activity. A strain of *Escherichia coli* strain made deficient by destruction in D-lactate dehydrogenase gene (ldhA) and in pyruvate formate-lyase gene (pflB and pflD) was prepared by a method of Kirill et al. (Kirill, A., PNAS, United States (2000) 97 6640-6645). The strain thus prepared was designated TM33 strain (*E. coli*ΔldhAΔpflB::Km$^r$ΔpflD::Cm$^r$) and used as a host for screening D-lactate dehydrogenase gene.

Reference Example 9

Screening of D-lactate Dehydrogenase Gene

*Escherichia coli* TM33 strain was inoculated into 100 ml of an LB medium containing 50 μg/ml kanamycin sulfate and 15 μg/ml chloramphenicol and cultured at a temperature of 37° C. for 24 hours to obtain a culture. The culture thus obtained was centrifuged at 3,000 rpm for 15 minutes to obtain 0.8 g wet microorganism. The obtained wet microorganism was washed 3 times with 10 ml of 10% glycerol and then suspended in 0.1 ml of 10% glycerol to obtain competent cells. 1 μl of the gene library derived from *Bacillus laevolacticus* JCM2513 strain, obtained in Reference Example 8, was added to, and introduced in a usual manner by electroporation into, the competent cells, and the resulting strains were placed on an M9GP agar medium (M9 medium+0.4% glucose+0.2% peptone) containing 50 μg/ml ampicillin sodium to obtain several strains capable of growing under anaerobic conditions.

Reference Example 10

Analysis of a Nucleotide Sequence of DNA Containing the D-Lactate Dehydrogenase Gene From the *Escherichia coli* TM33/pBL2 strain containing the recombinant DNA obtained above, a plasmid was prepared in a usual manner, and the resulting recombinant DNA was used in nucleotide sequencing. Nucleotide sequencing was carried out according to the method of Sanger by using Taq DyeDeoxy Terminator Cycle Sequencing Kit (manufactured by Applied Biochemical). The resulting nucleotide sequence of the DNA containing the D-lactate dehydrogenase gene was 2,995 base pairs. Search for an open reading frame for this sequence was conducted, and a DNA sequence (SEQ ID NO: 10) of the 1,011-bp D-lactate dehydrogenase gene was temporarily determined by using Genetyx (manufactured by Software Kaihatsu Co., Ltd.).

Reference Example 11

Preparation of an Expression Vector for D-Lactate Dehydrogenase Gene

D-LDH gene was cloned from *Bacillus laevolacticus*. The D-LDH gene was cloned by PCR and introduced in the same manner into an expression vector. The cloning method is described below.

*Bacillus laevolacticus* was cultured and then recovered by centrifugation, followed by extraction of genome DNA with UltraClean Microbial DNA Isolation Kit (manufactured by MO BIO). The specific operation followed the protocol attached to the kit. The resulting genome DNA was subsequently used as a template in PCR. The DNA obtained above was used as a template in cloning of D-LDH gene by PCR. In the PCR amplification reaction, KOD-Plus-polymerase (manufactured by Toyobo) estimated to have 50-fold accuracy relative to Taq was used. The reaction buffer, dNTPmix etc. used were those attached to the kit. D-LDH gene amplification primers (SEQ ID NOS: 11 and 12) were prepared such that an XhoI recognition sequence and NotI recognition sequence were added the 5- and 3-terminal sides respectively.

Each PCR amplification fragment was purified, then phosphorylated at its terminus with a T4 polynucleotide kinase (manufactured by TAKARA) and ligated to pUC118 vector (which had been treated by cleavage with a restriction enzyme HincII and then subjecting the cleavage surface to dephosphorylation). This ligation was conducted with DNA Ligation Kit Ver. 2 (manufactured by TAKARA). The ligation product was used to transform *Escherichia coli* DH5α from which a plasmid DNA was then recovered to obtain a plasmid wherein each D-LDH gene had been subcloned. The resulting pUC118 vector into which the D-LDH gene had been inserted was cleaved with restriction enzymes XhoI and NotI, and each of the resulting DNA fragments was inserted into an XhoI/NotI cleavage site of yeast expression vector pTRS11 (FIG. 5). The D-LDH gene expression vector thus prepared was designated pTM63.

Reference Example 12

Introduction of the D-LDH Gene Expression Vector into Yeast pTM63 obtained in Reference Example 11 was transformed into yeast *Saccharomyces cerevisiae* NBRC10505 strain. This transformation was carried out by the lithium acetate method using YEASTMAKER Yeast Transformation System (manufactured by CLONTECH). The operation followed the protocol attached to the kit. The *Saccharomyces cerevisiae* NBRC10505 strain used as a host is a strain deficient in the ability to produce uracil, and its transformant into which pTM63 had been introduced can be selected on an uracil-free medium by the function of URA3 gene possessed by pTM63.

Introduction of the D-LDH gene expression vector into the transformant obtained in this manner was confirmed by extracting a plasmid DNA-containing genome DNA by a genome DNA extraction kit Gentrukun (manufactured by TAKARA) and then using the genome DNA as a template in PCR with PreMix Taq (manufactured by TAKARA). As the primer, the primer used in cloning the D-LDH gene was used. As a result, it was confirmed that all the transformants have D-LDH gene introduced into them.

*Saccharomyces cerevisiae* NBRC10055 strain into which pTM63 had been introduced is hereinafter referred to as NBRC10505/pTM63 strain.

Example 31

Production of D-lactic Acid by Continuous Fermentation (No. 1)

Production of D-lactic acid was conducted by using the membrane separation-type continuous fermentation apparatus in FIG. 1 and a D-lactic acid production medium having the composition shown in Table 25. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 2.0 (L)
Used separation membrane: PVDF filtration membrane
Membrane separation element effective filtration area: 120 $cm^2$
Temperature control: 30 (° C.)
Fermentation reaction tank aeration: 0.2 (L/min) air
Fermentation reaction tank agitation rate: 800 (rpm)
pH adjustment: adjusted to pH 5.0 with 5 N NaOH
Sterilization: The culture tank including the separation membrane element, and the used medium, were sterilized with high-pressure steam in an autoclave at 121° C. for 20 minutes.
Regulation of the amount of membrane permeation water: flow rate regulation by transmembrane pressure difference (From start of continuous fermentation to 100 hours: regulated at 0.1 kPa or more to 5 kPa or less,
100 hours to 200 hours: regulated at 2 kPa or less, and
200 hours to 320 hours: regulated at 0.1 kPa or more to 20 kPa or less)
NBRC10505/pTM63 strain was used as the microorganism, a D-lactic acid production medium having the composition shown in Table 25 was used as the medium, and the concentration of D-lactic acid as a product was measured by the same HPLC method as in Reference Example 1. The concentration of glucose was measured with Glucose Test Wako C (Wako Pure Chemical Industries, Ltd.).

TABLE 25

| Yeast lactic acid fermentation medium | |
|---|---|
| Glucose | 100 g |
| Yeast Nitrogen base w/o amino acid (Difco) | 6.7 g |
| Standard 19 amino acids excluding leucine | 152 mg |
| Leucine | 760 mg |
| Inositol | 152 mg |
| p-Aminobenzoic acid | 16 mg |
| Adenine | 40 mg |
| | Unit (1/Liter) |

First, NBRC10505/pTM63 strain was shake-cultured overnight in 5 ml of a D-lactic acid production medium in a test tube (prior preliminary preculture). The resulting culture was inoculated into 50 ml of a fresh D-lactic acid production medium and shake-cultured for 24 hours at a temperature of 30° C. in a 500-ml Sakaguchi flask (preliminary preculture). The preliminary preculture was inoculated into 2.0 L of a D-lactic acid production medium in the membrane separation-type continuous fermentation apparatus shown in FIG. 1, a fermentation reaction tank 1 was stirred at 800 rpm with an agitator 5 attached thereto, followed by the aeration regulation, temperature control, and pH adjustment of the reaction tank 1, and the microorganism was cultured for 24 hours (preculture).

Immediately after preculture was finished, the fermentation liquor circulating pump 10 was operated, and the microorganism was continuously cultured under the conditions where in addition to the operation conditions at the time of preculture, a membrane separation tank 2 was aerated, a D-lactic acid fermentation medium was continuously fed, and the amount of membrane permeation water was regulated such that the amount of the fermentation liquor in the membrane separation-type continuous fermentation apparatus became 2 L, whereby cadaverine was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of lactic acid produced in the membrane permeation fermentation liquor and the residual glucose concentration were measured at an appropriate time. The results in the continuous fermentation test for 320 hours are shown in Table 26.

Stable production of D-lactic acid by continuous fermentation was feasible by the method of producing a chemical product according to the present invention by using the membrane separation-type continuous fermentation apparatus. The transmembrane pressure difference fluctuated within 2 kPa in the whole period of continuous fermentation.

Example 32

Production of D-lactic Acid by Continuous Fermentation (No. 2)

Production of D-lactic acid was conducted by using the continuous fermentation apparatus in FIG. 2 and a D-lactic acid production medium having the composition shown in Table 25. The medium was used after high-pressure steam sterilization (121° C., 15 minutes). As the separation membrane element material, a molding of stainless steel and polysulfone resin was used. As the separation membrane, the porous membrane prepared in Reference Example 2 was used. Unless otherwise noted, the operation conditions in this example are as follows:
Fermentation reaction tank capacity: 1.5 (L)
Used separation membrane: polyvinylidene fluoride filtration membrane
Membrane separation element effective filtration area: 120 $cm^2$
Temperature control: 30 (° C.)
Fermentation reaction tank aeration: 0.2 (L/min) air
Fermentation reaction tank agitation rate: 800 (rpm)
pH adjustment: adjusted to pH 5.0 with 5 N NaOH
Sterilization: The culture tank including the separation membrane element, and the used medium, were sterilized with high-pressure steam in an autoclave at 121° C. for 20 minutes.
Regulation of the amount of membrane permeation water: flow rate regulation by transmembrane pressure difference (From start of continuous fermentation to 90 hours: regulated at 0.1 kPa or more to 5 kPa or less,
90 hours to 180 hours: regulated at 0.1 kPa or more to 2 kPa or less, and
180 hours to 264 hours: regulated at 0.1 kPa or more to 20 kPa or less)

NBRC10505/pTM63 strain was used as the microorganism, a D-lactic acid production medium having the composition shown in Table 25 was used as the medium, the concentration of D-lactic acid as a product was measured by the same HPLC method as in Reference Example 1. The concentration of glucose was measured with Glucose Test Wako C (Wako Pure Chemical Industries, Ltd.).

First, NBRC10505/pTM63 strain was shake-cultured overnight in 5 ml of a D-lactic acid production medium in a test tube (prior preliminary preculture). The resulting culture was inoculated into 50 ml of a fresh D-lactic acid production medium and shake-cultured for 24 hours at a temperature of 30° C. in a 500-ml Sakaguchi flask (preliminary preculture).

The preliminary preculture was inoculated into 1.5 L of a D-lactic acid production medium in the continuous fermentation apparatus shown in FIG. 2, a fermentation reaction tank 1 was stirred at 800 rpm with an agitator 5 attached thereto, followed by the aeration regulation, temperature control and pH adjustment of the fermentation reaction tank 1, while the microorganism was cultured for 24 hours (preculture). Immediately after preculture was finished, the microorganism was continuously cultured while a D-lactic acid production medium was continuously fed, and the amount of membrane permeation water was regulated such that the amount of the fermentation liquor in the continuous fermentation apparatus became 1.5 L, whereby D-lactic acid was produced by continuous fermentation. In this continuous fermentation test, the amount of membrane permeation water was regulated and changed under the membrane permeation water control conditions described above, during which the water head difference was measured as transmembrane pressure difference with a water head difference regulating apparatus 3. The concentration of D-lactic acid produced in the membrane permeation fermentation liquor and the residual glucose concentration were measured at an appropriate time. The rate of production of D-lactic acid calculated from the D-lactic acid and introduced glucose are shown in Table 26.

As a result of the fermentation test for 264 hours, stable production of D-lactic acid by continuous fermentation was feasible by the method of producing a chemical product according to the present invention by using the continuous fermentation apparatus in FIG. 2. The transmembrane pressure difference fluctuated within 2 kPa in the whole period of continuous fermentation.

Comparative Example 16

Production of D-lactic Acid by Batch Fermentation

As a fermentation form using a microorganism, most typical batch fermentation was conducted in a 2-L jar fermenter to evaluate its D-lactic acid productivity. The medium was used after high-pressure steam sterilization (121° C., 15 minutes). In this comparative example, NBRC10505/pTM63 strain was used as the microorganism, the concentration of D-lactic acid as a product was evaluated by HPLC, and the concentration of glucose was measured with Glucose Test Wako C (Wako Pure Chemical Industries, Ltd.). The operation conditions in this comparative example are as follows:
Fermentation reaction tank capacity (amount of D-lactic acid production medium): 1.0 (L)
Temperature control: 30 (° C.).
Fermentation reaction tank aeration: 0.2 (L/min) air
Fermentation reaction tank agitation rate: 300 (rpm)
pH adjustment: adjusted to pH 5.0 with 5 N NaOH First, NBRC10505/pTM63 strain was shake-cultured overnight in 5 ml D-lactic acid production in a test tube (preliminary preculture). The resulting culture was inoculated into 50 ml fresh D-lactic acid production medium and shake-cultured for 24 hours at a temperature of 30° C. in a 500-ml Sakaguchi flask (preculture). The resulting preculture was inoculated into 1.5 L D-lactic acid production medium in a jar fermenter. The microorganism was subjected to batch fermentation in the D-lactic acid production medium. The results are shown in Table 26.

TABLE 26

|  |  | Comparative Example 16 | Example 31 | Example 32 |
|---|---|---|---|---|
| Fermentation time | (hr) | 75 | 320 | 268 |
| Introduced glucose | (g) | 100 | 2790 | 2340 |
| Produced D-lactic acid | (g) | 18.8 | 533 | 442 |
| Unused glucose | (g) | 0 | 55 | 50 |
| D-Lactic acid yield | (g/g) | 18.8 | 19.5 | 19.3 |
| D-lactic acid production rate | (g/L/hr) | 0.25 | 0.93 | 1.10 |

It could be revealed that the rate of production of D-lactic acid was significantly improved by the method of producing a chemical product according to the present invention using the fermentation apparatus shown in FIGS. 1 and 2.

Reference Example 13

Preparation of a Porous Membrane (No. 5)

A vinylidene fluoride homopolymer having a weight-average molecular weight of 417,000 and γ-butyrolactone were melted at a temperature of 170° C. in amounts of 38% by weight and 62% by weight respectively to prepare a stock solution. This stock solution, accompanied by γ-butyrolactone as a hollow-forming liquid, was discharged from a base and cooled in a cooling bath consisting of 80% aqueous γ-butyrolactone solution at a temperature of 20° C. to prepare a hollow fiber membrane.

Then, 14% by weight of vinylidene fluoride homopolymer having a weight-average molecular weight of 284,000, 1% by weight of cellulose acetate propionate (CAP482-0.5 manufactured by Eastman Chemical), 77% by weight of N-methyl-2-pyrrolidone, 5% by weight of polyoxyethylene coconut oil fatty acid sorbitan (trade name: Ionet T-20C, manufactured by Sanyo Chemical Industries, Ltd.) and 3% by weight of water were mixed and melted at a temperature of 95° C. to prepare a stock solution. This stock solution was applied uniformly onto the surface of the hollow fiber membrane and immediately coagulated in a water bath to prepare a hollow fiber membrane. The resulting hollow fiber membrane had an average pore size of 0.05 μm on the surface of the water-treated side. When the separation membrane was evaluated for its purified-water permeability coefficient, the purified-water permeability coefficient was $5.5 \times 10^{-9}$ m$^3$/m$^2$·s·Pa. Measurement of the purified-water permeability coefficient was conducted with reverse osmosis membrane-treated purified water at 25° C. with a head height of 1 m. The standard deviation of the average pore size was 0.006 μm.

Example 33

Preparation of L-lactic Acid with Hollow Fiber Membrane (No. 1)

The separation membrane element shown in FIG. 4 having an effective filtration area of 120 cm² prepared using a porous membrane prepared in Reference Example 13 was used as a separation membrane in the same L-lactic acid continuous fermentation test as in Example 1. The results together with the results of Comparative Example 1 are shown in Table 27. Stable production of L-lactic acid by continuous fermentation was feasible. The transmembrane pressure difference fluctuated within 2 kPa in the whole period of continuous fermentation.

Example 34

Preparation of L-Lactic Acid with Hollow Fiber Membrane (No. 2)

The separation membrane element shown in FIG. 4 having an effective filtration area of 120 cm² prepared using a porous membrane prepared in Reference Example 13 was used as a separation membrane in the same L-lactic acid continuous fermentation test as in Example 4. The results together with the results of Comparative Example 1 are shown in Table 27. It could be confirmed that stable production of L-lactic acid by continuous fermentation was feasible. The transmembrane pressure difference fluctuated within 2 kPa in the whole period of continuous fermentation.

TABLE 27

| | | Comparative Example 1 | Example 33 | Example 34 |
|---|---|---|---|---|
| Fermentation time | (hr) | 72 | 300 | 300 |
| Introduced glucose | (g) | 100 | 3210 | 2600 |
| Total produced L-lactic acid | (g) | 26 | 1980 | 1570 |
| Unused glucose | (g) | 0 | 70 | 60 |
| L-lactic acid yield relative to sugar | (g/g) | 0.26 | 0.63 | 0.62 |
| L-Lactic acid production rate | (g/L/hr) | 0.36 | 3.3 | 3.5 |

INDUSTRIAL APPLICABILITY

The present invention provides a method of producing a chemical product by continuous fermentation maintaining high productivity stably for a long time by a simple operation method. According to the present invention, continuous fermentation maintaining high productivity stably for a long time under simple operation conditions is made feasible, and a chemical product that is a fermentation product can be stably produced at low cost widely in fermentation industry.

The invention claimed is:

1. A method of producing a chemical product through continuous fermentation which includes filtering a culture of a yeast or bacteria with a separation membrane to recover a product from a filtrate and simultaneously retaining a non-filtered fluid in, or refluxing it to, the culture, and adding fermentation materials to the culture, wherein a porous membrane having an average pore size of 0.01 µm or more to less than 1 µm is a polyvinylidene fluoride hollow fiber membrane used as the separation membrane and the filtration is conducted with a transmembrane pressure difference in the range of 0.1 to 20 kPa.

2. The method of producing a chemical product according to claim 1, wherein the purified-water permeability coefficient of the porous membrane is $2\times10^{-9}$ m$^3$/m$^2$/s/pa or more to $6\times10^{-7}$ m$^3$/m$^2$/s/pa or less.

3. The method of producing a chemical product according to claim 1, wherein the average pore size of the porous membrane is 0.01 µm or more to less than 0.2 µm, and the standard deviation of the pore size of the porous membrane is 0.1 µm or less.

4. The method of producing a chemical product according to claim 1, wherein the culture of the microorganism or cultured cells and the fermentation materials contain sugars.

5. The method of producing a chemical product according to claim 1, wherein the chemical product is an organic acid.

6. The method of producing a chemical product according to claim 1, wherein the chemical product is L-lactic acid.

7. The method of producing a chemical product according to claim 1, wherein the chemical product is D-lactic acid.

8. The method of producing a chemical product according to claim 1, wherein the chemical product is pyruvic acid.

9. The method of producing a chemical product according to claim 1, wherein the chemical product is succinic acid.

10. The method of producing a chemical product according to claim 1, wherein the chemical product is itaconic acid.

11. The method of producing a chemical product according to claim 1, wherein the chemical product is cadaverine.

12. The method of producing a chemical product according to claim 1, wherein the chemical product is an alcohol.

13. The method of producing a chemical product according to claim 1, wherein the chemical product is ethanol.

14. The method of producing a chemical product according to claim 1, wherein the chemical product is 1,3-propanediol.

15. The method of producing a chemical product according to claim 1, wherein the chemical product is a nucleic acid.

16. The method of producing a chemical product according to claim 1, wherein the chemical product is inosine.

17. The method of producing a chemical product according to claim 1, wherein the chemical product is an amino acid.

18. The method of producing a chemical product according to claim 1, wherein the chemical product is L-threonine.

* * * * *

UNITED STATES PATENT AND TRADEMARK OFFICE
CERTIFICATE OF CORRECTION

| | | |
|---|---|---|
| PATENT NO. | : 9,587,253 B2 | Page 1 of 1 |
| APPLICATION NO. | : 12/280197 | |
| DATED | : March 7, 2017 | |
| INVENTOR(S) | : Sawai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 338 days.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*